(12) United States Patent
Villenave et al.

(10) Patent No.: US 11,542,476 B2
(45) Date of Patent: Jan. 3, 2023

(54) ADVANCED PULMONARY MODELS

(71) Applicant: EMULATE, INC., Boston, MA (US)

(72) Inventors: Remi Villenave, Boston, MA (US); Carolina Lucchesi, Westwood, MA (US); Justin Nguyen, Medford, MA (US); Catherine Karalis, Brookline, MA (US); Geraldine Hamilton, Boston, MA (US); Buket Baddal, Brookline, MA (US); Michael Salmon, Boston, MA (US)

(73) Assignee: EMULATE, INC., Boston, MA (US)

( * ) Notice: Subject to any disclaimer, the term of this patent is extended or adjusted under 35 U.S.C. 154(b) by 438 days.

(21) Appl. No.: 16/692,383

(22) Filed: Nov. 22, 2019

(65) Prior Publication Data

US 2020/0087628 A1    Mar. 19, 2020

Related U.S. Application Data

(63) Continuation of application No. PCT/US2018/034116, filed on May 23, 2018.

(60) Provisional application No. 62/669,110, filed on May 9, 2018, provisional application No. 62/632,519, filed on Feb. 20, 2018, provisional application No. 62/556,196, filed on Sep. 8, 2017, provisional application No. 62/509,967, filed on May 23, 2017.

(51) Int. Cl.
*C12N 5/071* (2010.01)
*B01L 3/00* (2006.01)
*C12N 1/20* (2006.01)

(52) U.S. Cl.
CPC ...... *C12N 5/0688* (2013.01); *B01L 3/502769* (2013.01); *C12N 1/20* (2013.01); *C12N 2502/00* (2013.01)

(58) Field of Classification Search
CPC .............. B81C 1/00119; C12N 2502/27
See application file for complete search history.

(56) References Cited

U.S. PATENT DOCUMENTS

| | | | |
|---|---|---|---|
| 5,642,730 A | 7/1997 | Baran | 128/207.14 |
| 8,647,861 B2 | 2/2014 | Ingber et al. | 435/289.1 |
| 2006/0093596 A1* | 5/2006 | Douglas | C07K 14/461 |
| | | | 435/325 |
| 2010/0150943 A1* | 6/2010 | Grandi | A61P 31/04 |
| | | | 435/69.3 |
| 2014/0072622 A1* | 3/2014 | Denoel | A61K 47/06 |
| | | | 424/244.1 |
| 2014/0342445 A1 | 11/2014 | Ingber et al. | 435/294.1 |
| 2016/0311911 A1 | 10/2016 | Sur et al. | 424/143.1 |
| 2017/0312322 A1* | 11/2017 | Rohwer | A61K 45/06 |
| 2019/0307873 A1* | 10/2019 | Pfeifer | A61P 31/04 |

FOREIGN PATENT DOCUMENTS

| WO | WO/2015/027039 | 2/2015 |
|---|---|---|
| WO | WO/2015/138034 | 9/2015 |
| WO | WO/2017/019778 | 2/2017 |
| WO | WO/2017/066507 | 4/2017 |

OTHER PUBLICATIONS

Benam et al. (2016) Small airway-on-a-chip enables analysis of human lung inflammation and drug responses in vitro, Nature Methods, vol. 13, No. 2 pp. 151-157 (this ref contains "Oneline Methods" section ousside page range of 151-157).*
Rajas et al. (May 2, 2017) Glycosaminoglycans are involved in bacterial adherence to lung cells BMC Infect. Diseases, vol. 17, isseu 319, pp. 1-14.*
Keller et al. (2013) PspK of *Streptococcus pneumoniae* Increases Adherence to Epithelial Cells and Enhances Nasopharyngeal Colonization, Infect. Immun., vol. 81, pp. 173-181.*
Benam et al. (2016) Small airway-on-a-chip enables analysis of human lung inflammation and drug responses in vitro, Nature Methods, vol. 13, No. 2, pp. 151-157.*
Guevara, C. et al. (2016) "Highly differentiated human airway epithelial cells: a model to study host cell-parasite interactions in pertussis," *Infectious Diseases 48*(3), 177-188.

(Continued)

*Primary Examiner* — Suzanne M Noakes
(74) *Attorney, Agent, or Firm* — Medlen & Carroll, LLP

(57) ABSTRACT

The present invention relates to microfluidic fluidic systems and methods for the in vitro modeling diseases of the lung and small airway. In one embodiment, the invention relates to a system for testing responses of a microfluidic Small Airway-on-Chip infected with one or more infectious agents (e.g. respiratory viruses) as a model of respiratory disease exacerbation (e.g. asthma exacerbation). In one embodiment, this disease model on a microfluidic chip allows for a) the testing of anti-inflammatory and/or anti-viral compounds introduced into the system, as well as b) the monitoring of the participation, recruitment and/or movement of immune cells, including the transmigration of cells. In particular, this system provides, in one embodiment, an in-vitro platform for modeling severe asthma as "Severe Asthma-on-Chip." In some embodiments, this invention provides a model of viral-induced asthma in humans for use in identifying potentially effective treatments.

9 Claims, 32 Drawing Sheets

(56) References Cited

OTHER PUBLICATIONS

Meng, F. et al. (2016) "Efficient suilysin-mediated invasion and apoptosis in porcine respiratory epithelial cells after streptococcal infection under air-liquid interface conditions," *Scientific Reports* 6(1), Article No. 26748.
Yonker, L. M. et al. (2015) "A Novel Model: Transepithelial Neutrophil Migration Using Differentiated Human Airway Stem Cell Air-Liquid Interface," in *C39. Regulation of Inflammation and Lung Injury II*, pp. A4342-A4342.
Australian Search Report for Application No. 2018273233 dated Aug. 6, 2021.
Singapore Search Report for Application No. 11201910993Y dated May 28, 2021.
Australian Search Report for Application No. 2018273233 dated Mar. 25, 2021.
Balibar, C. J. et al. (2015) "Mutant Alleles of lptD Increase the Permeability of Pseudomonas aeruginosa and Define Determinants of Intrinsic Resistance to Antibiotics," *Antimicrobial Agents and Chemotherapy* 60(2), 845-854.
Benam, K. H. et al. (2016) "Small airway-on-a-chip enables analysis of human lung inflammation and drug responses in vitro," *Nature Methods* 13(2), 151-157.
Boers, J. E. et al. (1999) "Number and Proliferation of Clara Cells in Normal Human Airway Epithelium," *American Journal of Respiratory and Critical Care Medicine* 159(5), 1585-1591.
Busse, W. W. et al. (2010) "Role of viral respiratory infections in asthma and asthma exacerbations," *Lancet (London, England)* 376(9743), 826-834.
Clevers, H. (2016) "Modeling Development and Disease with Organoids," *Cell* 165(7), 1586-1597.
Doerr, A. (2016) "The condition-dependent proteome," *Nature Methods* 13(2), 117-117.
Ehrhardt, C. et al. (2006) "Towards an in vitro model of cystic fibrosis small airway epithelium: characterisation of the human bronchial epithelial cell line CFBE41o-," *Cell and Tissue Research* 323(3), 405-415.
Fahya et al. (1995) "Prominent neutrophilic inflammation in sputum from subjects with asthma exacerbation," *Journal of Allergy and Clinical Immunology* 95(4), 843-852.

Høiby, N. et al. (2010) "Pseudomonas aeruginosa biofilms in cystic fibrosis," *Future Microbiology* 5(11), 1663-1674.
Jakiela, B. et al. (2008) "Basal cells of differentiated bronchial epithelium are more susceptible to rhinovirus infection," *American Journal of Respiratory Cell and Molecular Biology* 38(5), 517-523.
Lachowicz-Scroggins, M. E. et al. (2010) "Interleukin-13-induced mucous metaplasia increases susceptibility of human airway epithelium to rhinovirus infection," *American Journal of Respiratory Cell and Molecular Biology* 43(6), 652-661.
Livraghi, A. et al. (2007) "Cystic Fibrosis and Other Respiratory Diseases of Impaired Mucus Clearance," *Toxicologic Pathology* 35(1), 116-129.
Mercer, R. R. et al. (1994) "Cell Number and distribution in human and rat airways," *American Journal of Respiratory Cell and Molecular Biology* 10(6), 613-624.
Pauwels, R. A. et al. (2004) "Burden and clinical features of chronic obstructive pulmonary disease (COPD)," *Lancet* 364(9434), 613-620.
Piroth, L. et al. (1999) "Development of a new experimental model of penicillin-resistant *Streptococcus pneumoniae* pneumonia and amoxicillin treatment by reproducing human pharmacokinetics," *Antimicrobial Agents and Chemotherapy* 43(10), 2484-2492.
Rai, P. et al. (2015) "*Streptococcus pneumoniae* secretes hydrogen peroxide leading to DNA damage and apoptosis in lung cells," *Proceedings of the National Academy of Sciences* 112(26), E3421.
Soto, S. M. (2013) "Role of efflux pumps in the antibiotic resistance of bacteria embedded in a biofilm," *Virulence* 4(3), 223-229.
Torres, A. et al. (1996) "Value of intracellular bacteria detection in the diagnosis of ventilator associated pneumonia," *Thorax* 51(A), 378-384.
Wanner, A. et al. (1996) "Mucociliary clearance in the airways," *American Journal of Respiratory and Critical Care Medicine* 154(6), 1868-1902.
WHO. Chronic obstmctive pulmonary disease (COPD) www.who.int/respiratory/copd/en/index.html.
Wong, A. P. et al. (2012) "Directed differentiation of human pluripotent stem cells into mature airway epithelia expressing functional CFTR protein," *Nature Biotechnology* 30(9), 876-882.
PCT International Search Report of International Application No. PCT/US2018/034116 dated Aug. 23, 2018.

* cited by examiner

Figure 1A-B
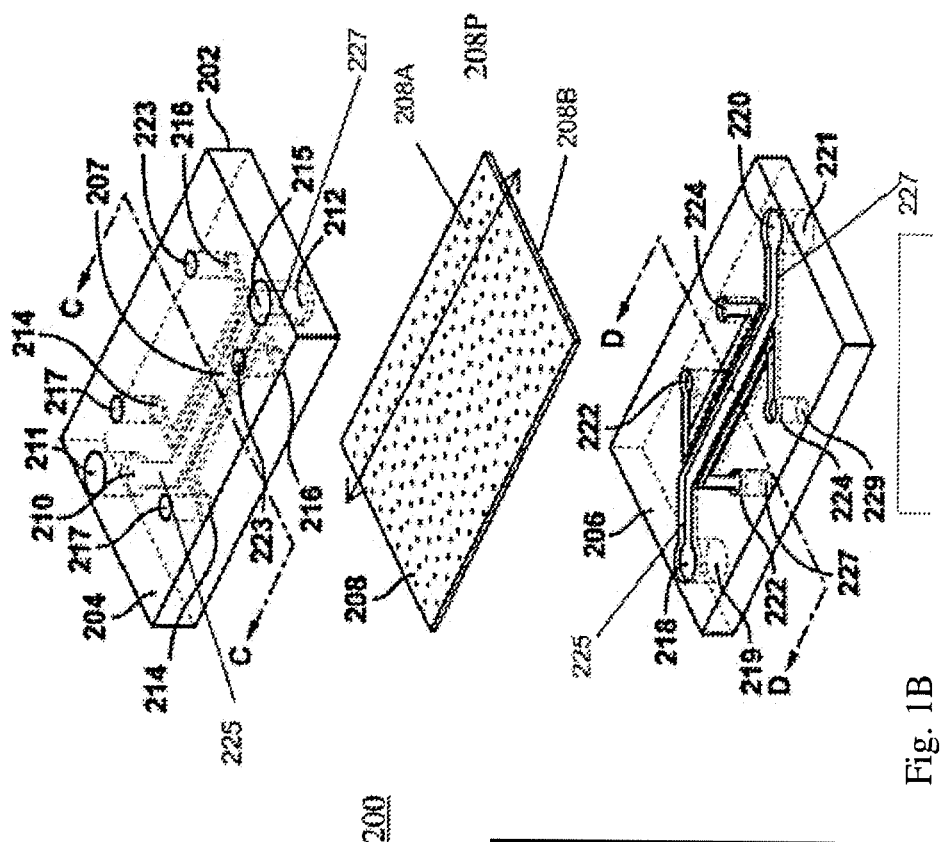
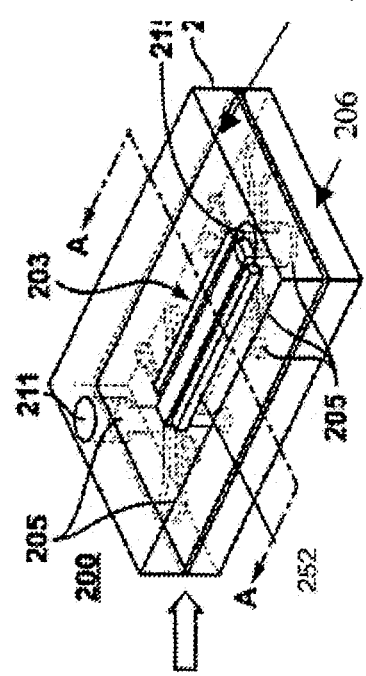
Fig. 1A
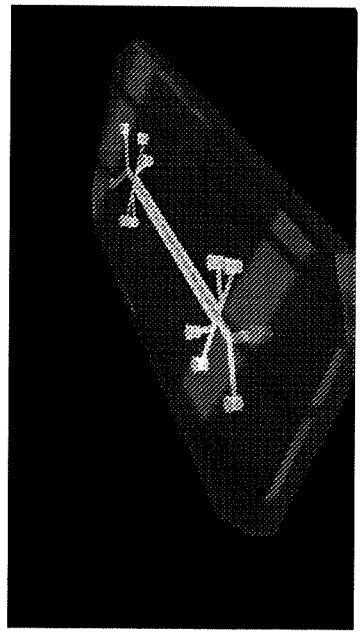
Fig. 1B

Figure 3A-H
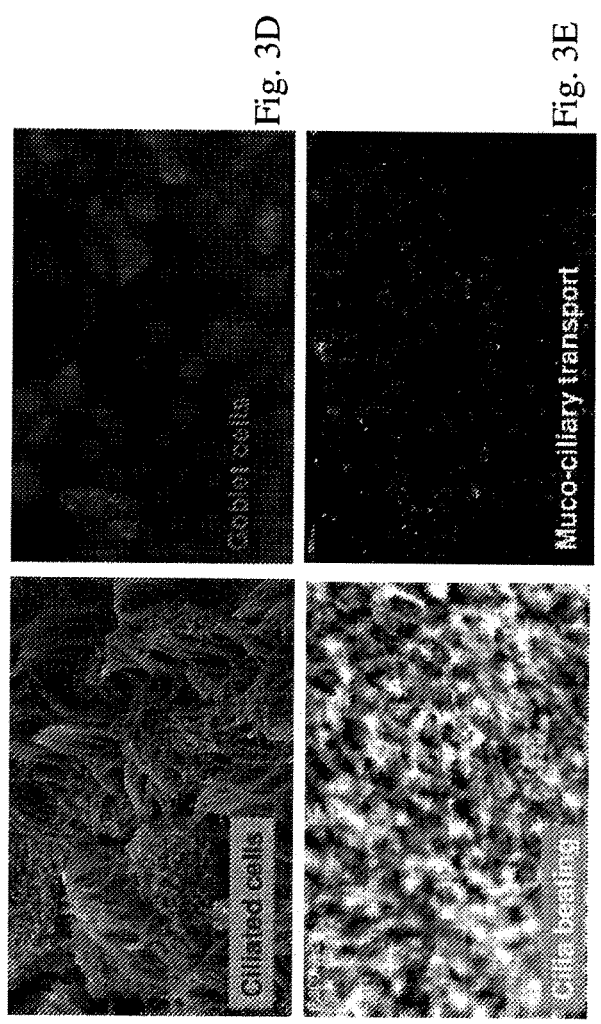
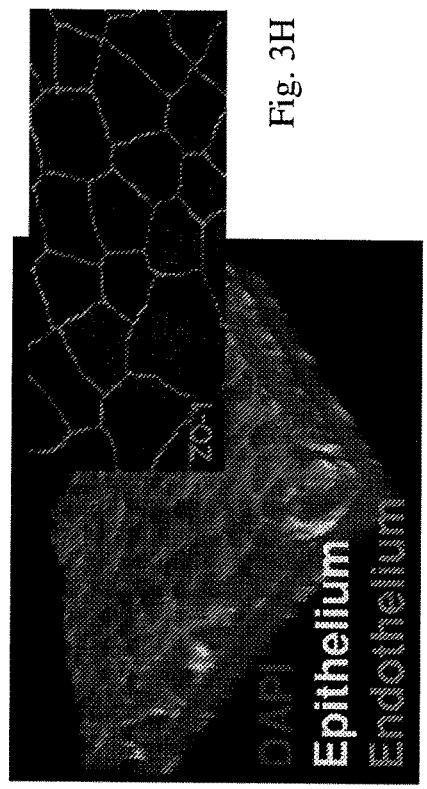
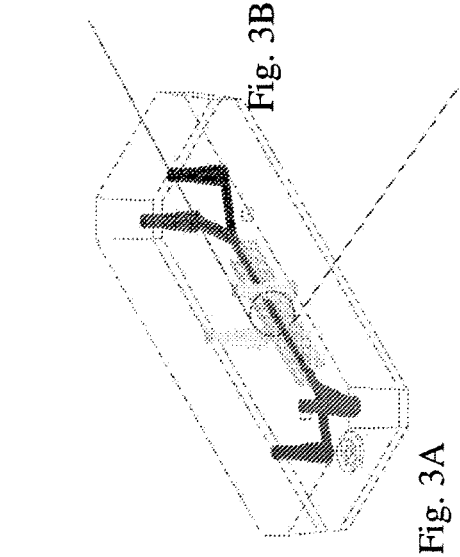
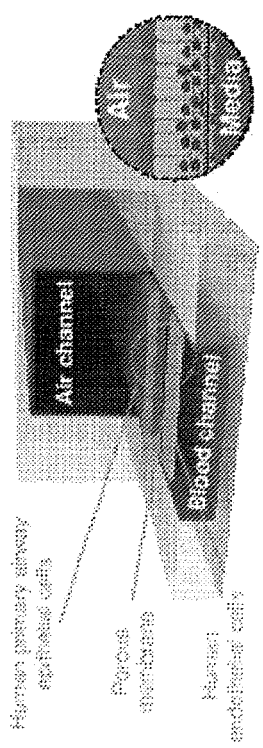

Figure 4A-F
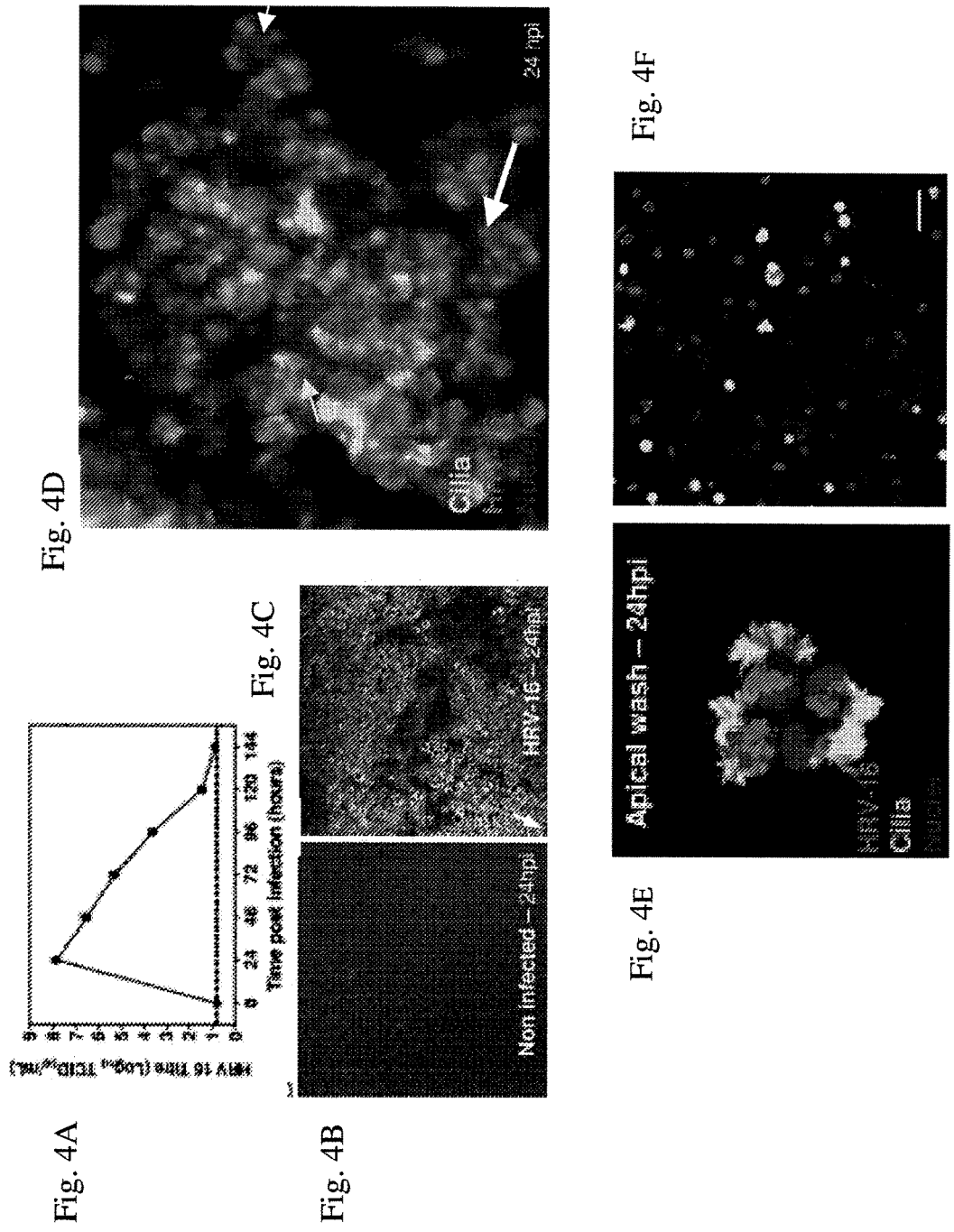

Figure 5A-E
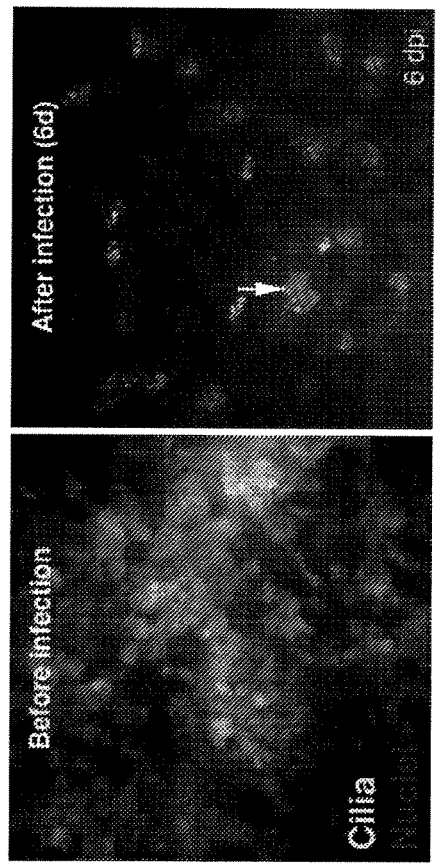
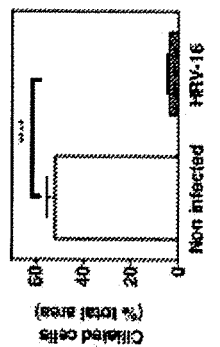
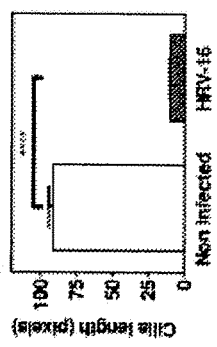
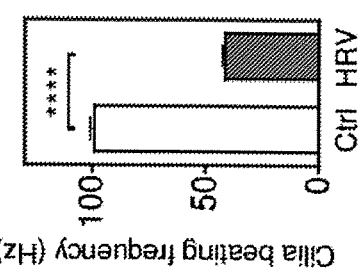
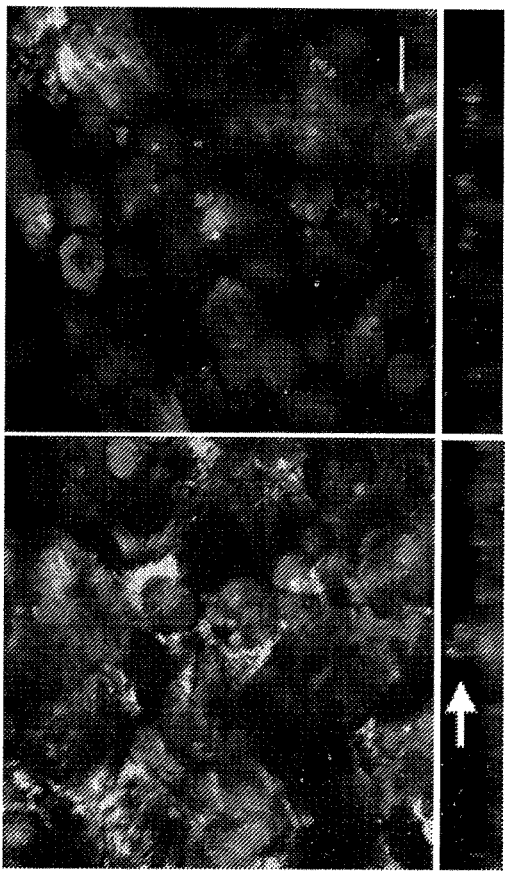

Figure 6A-B

Figure 7A1-4 - 7B1-5
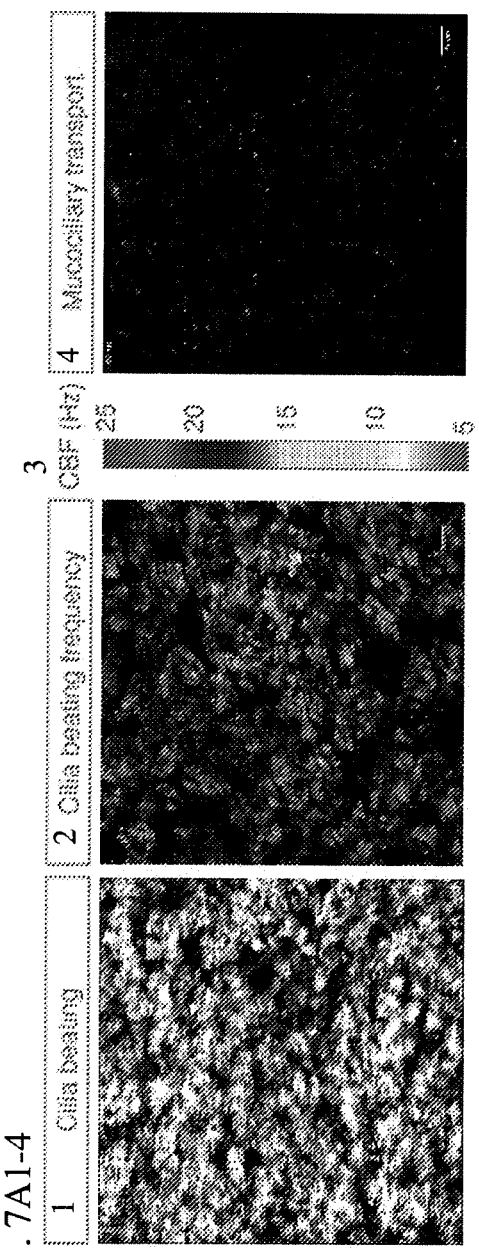
Fig. 7A1-4
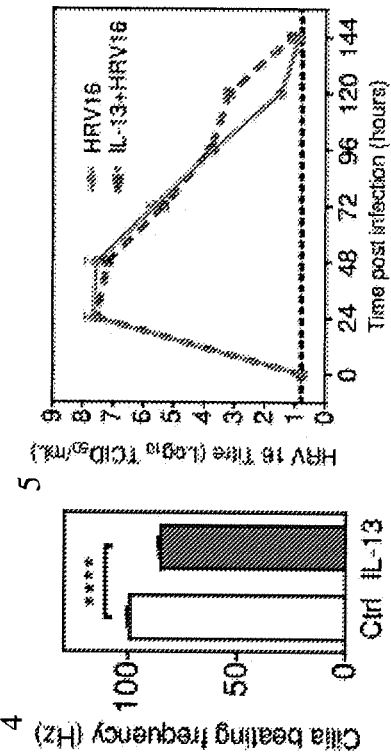
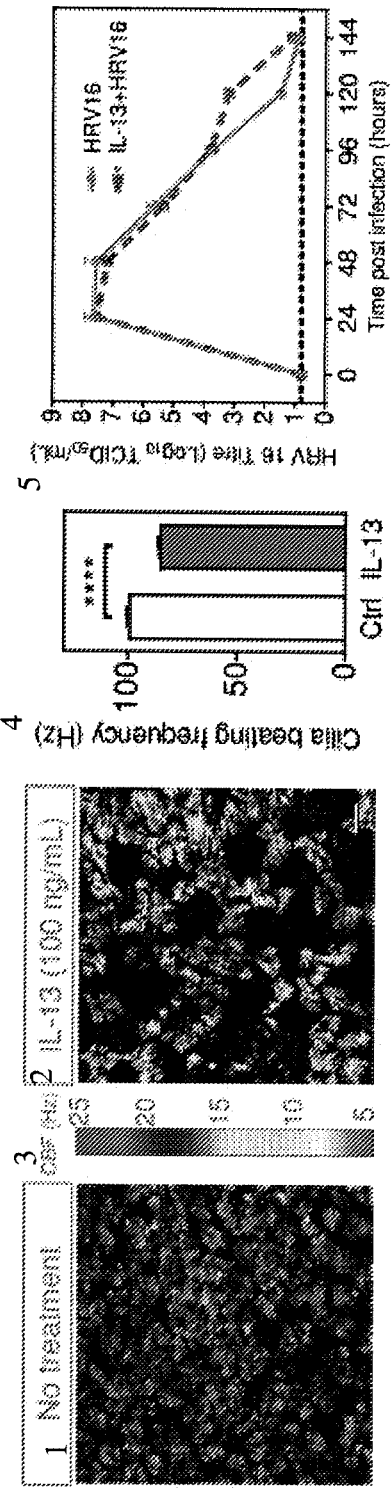
Fig. 7B1-5

Figure 8A-D

Figure 9A-C
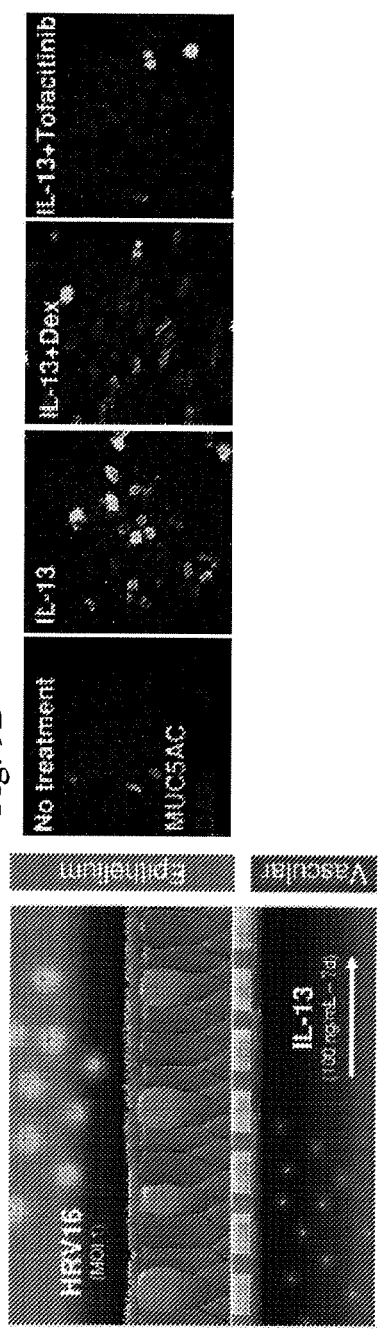
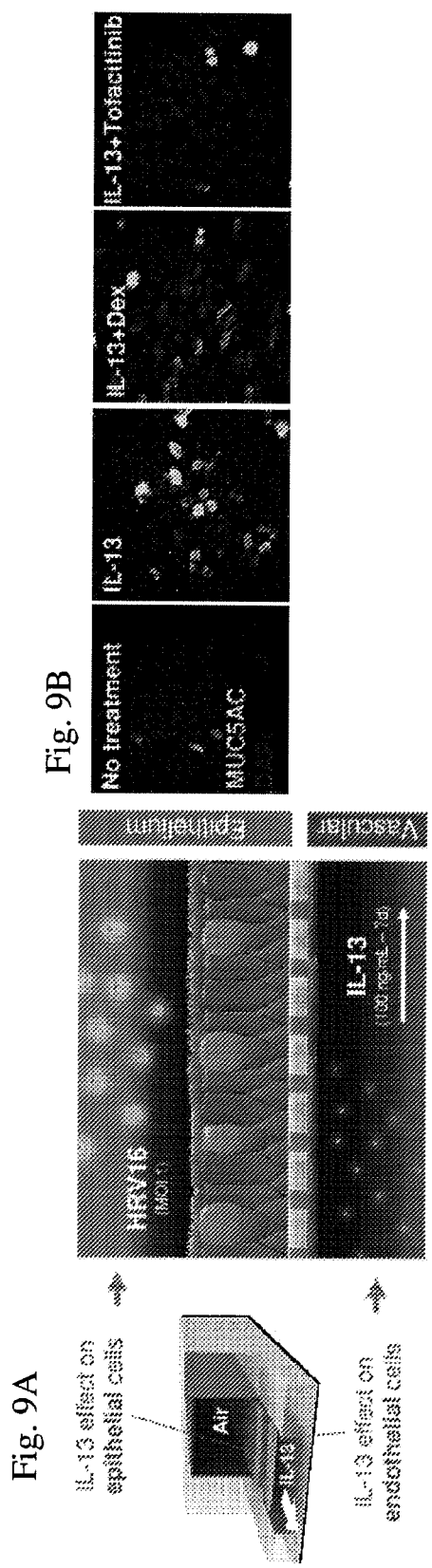
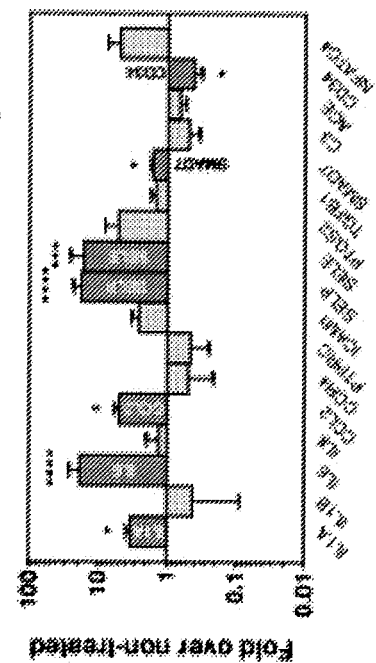
Fig. 9A
Fig. 9B
Fig. 9C

Figure 13A-C
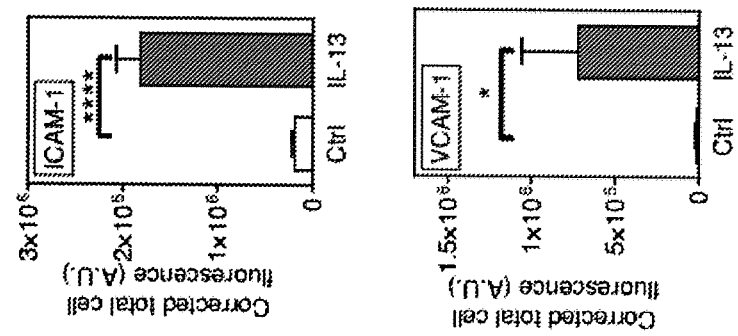
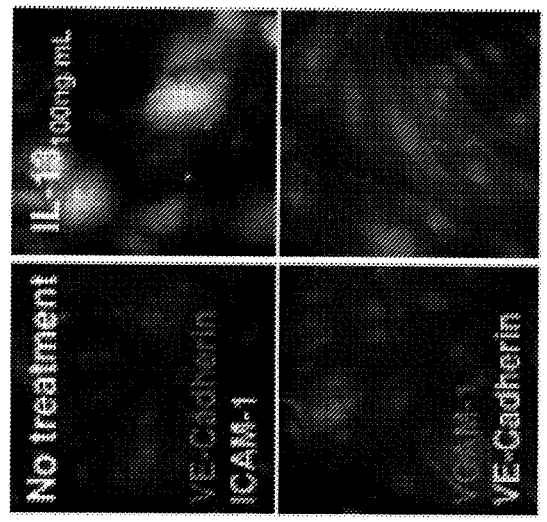
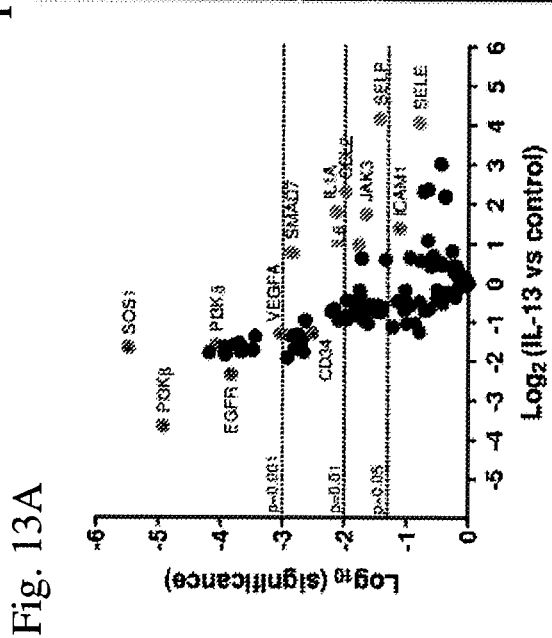

Figure 14A-C
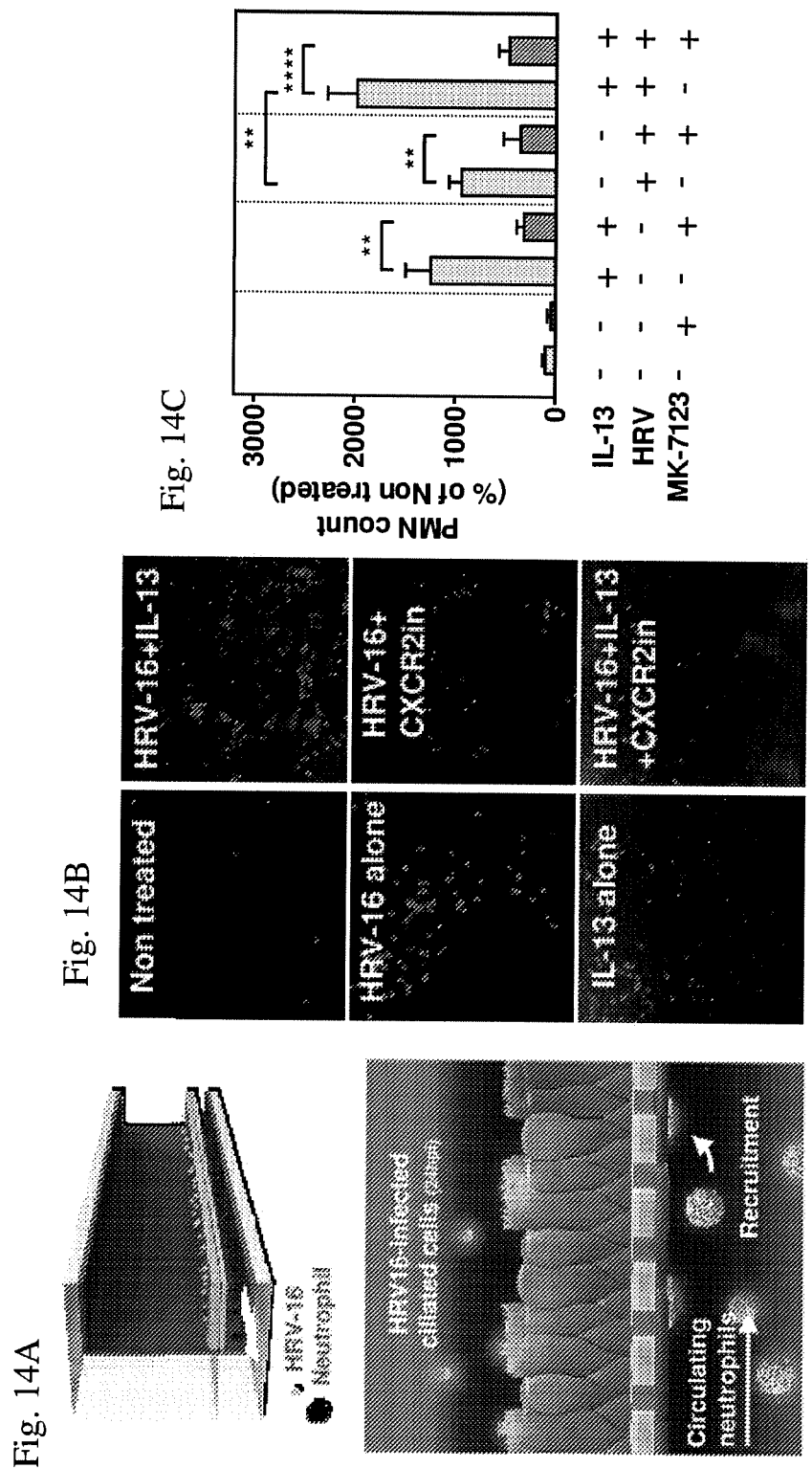

Figure 15A-D

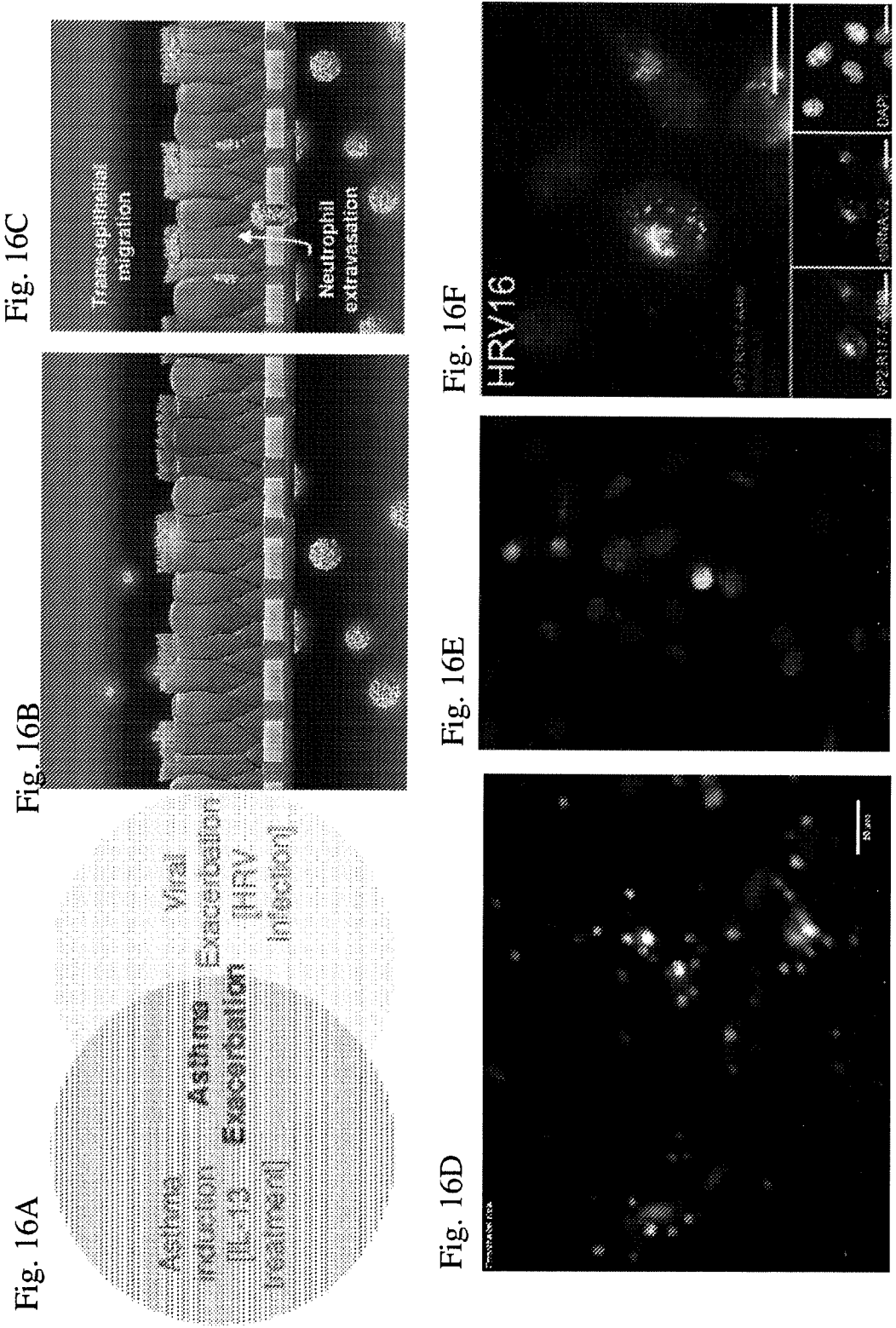
Figure 16A-F

Figure 17A-C
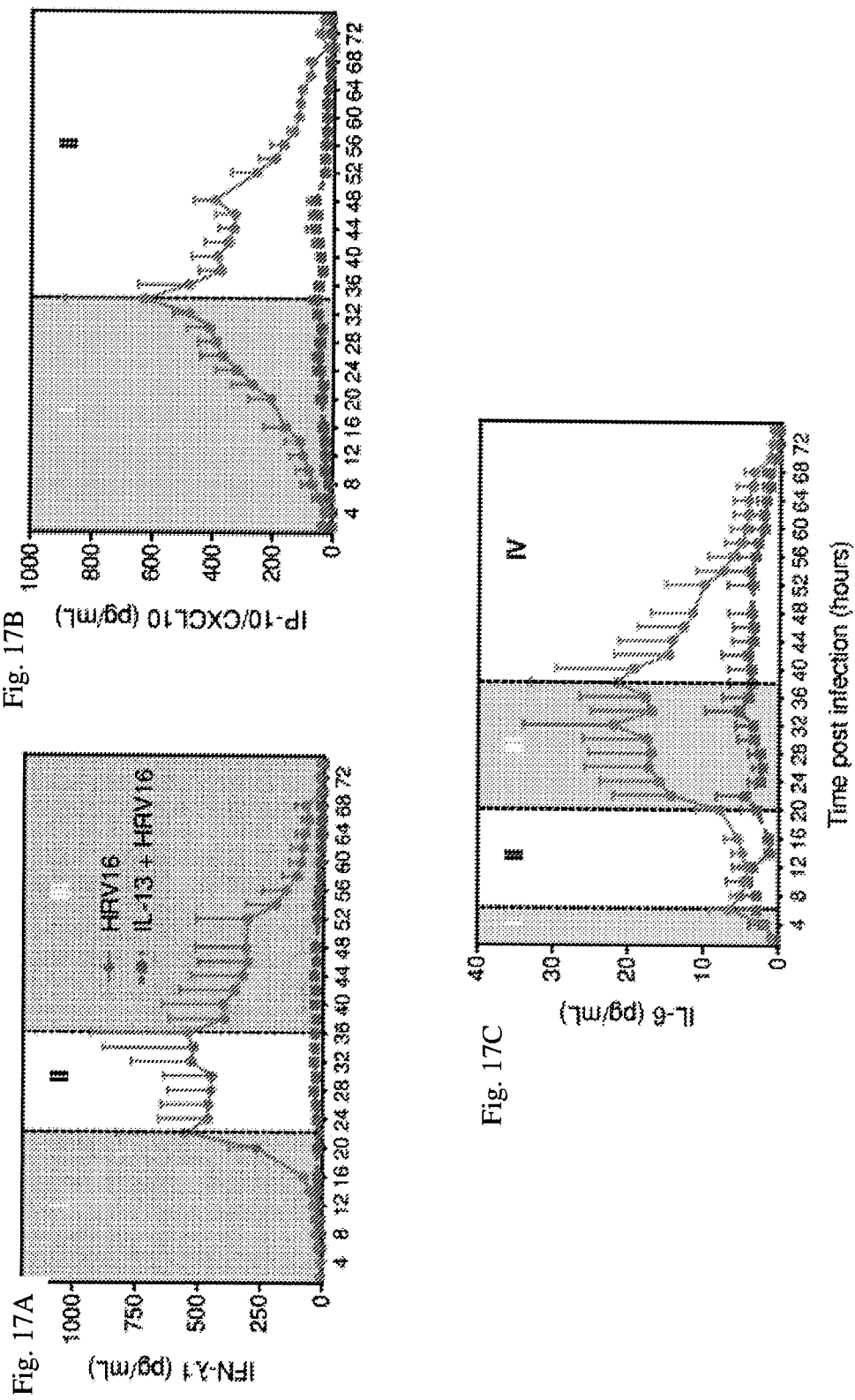

Figure 19A-B
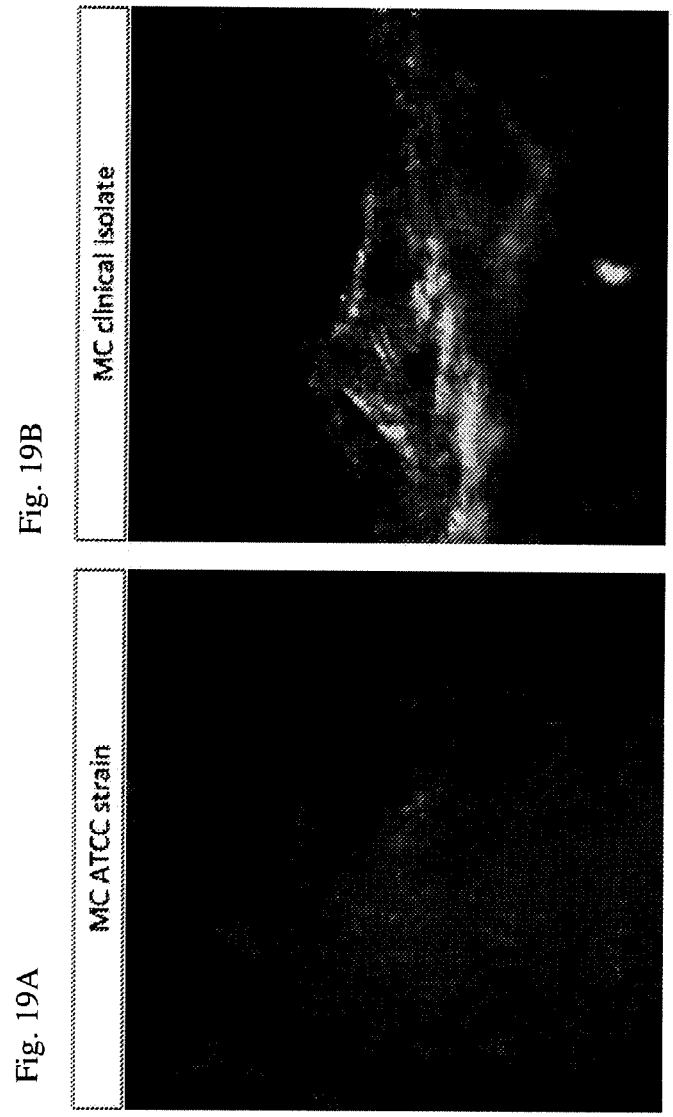

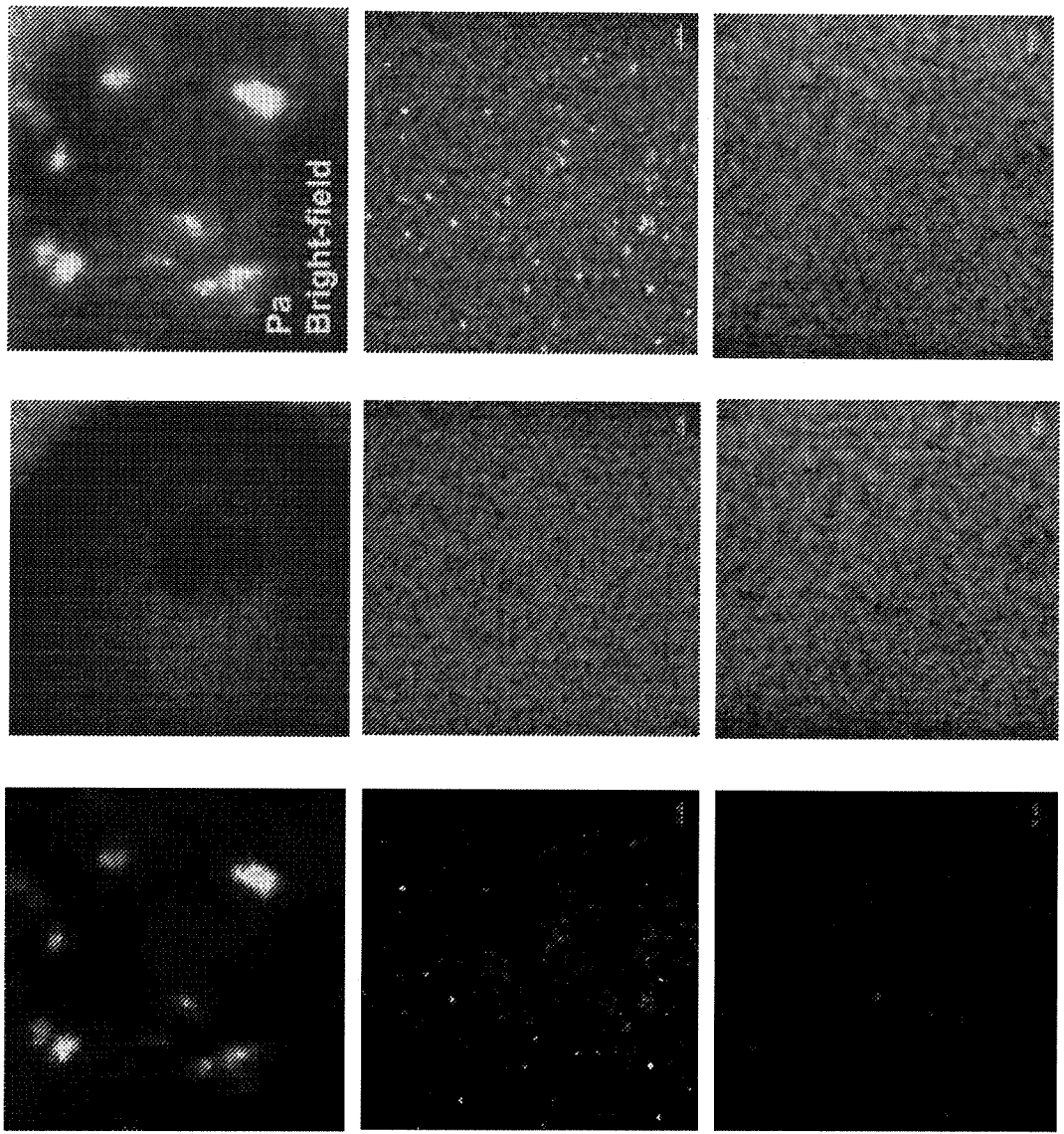
Figure 28A-C

Figures 32A-D
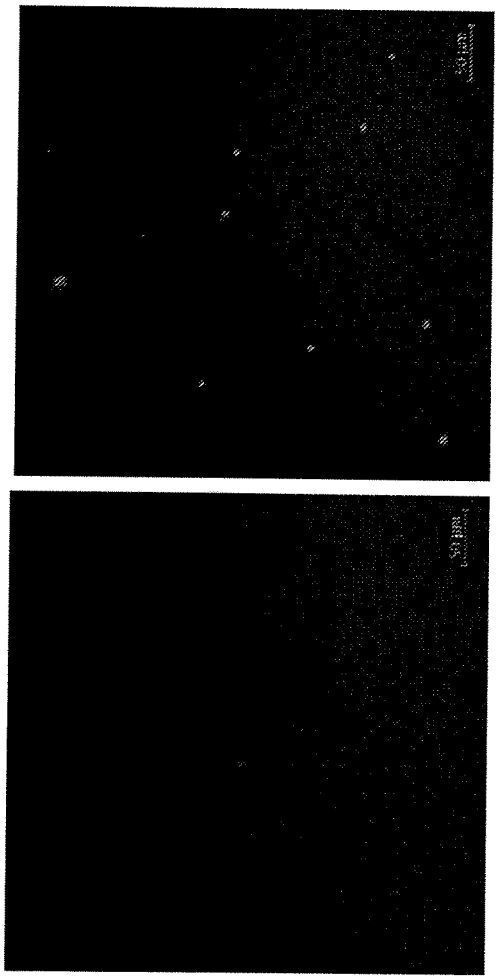
Figure 32A
Figure 32B
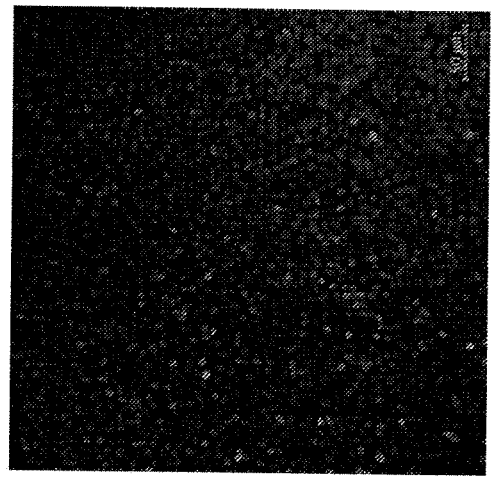
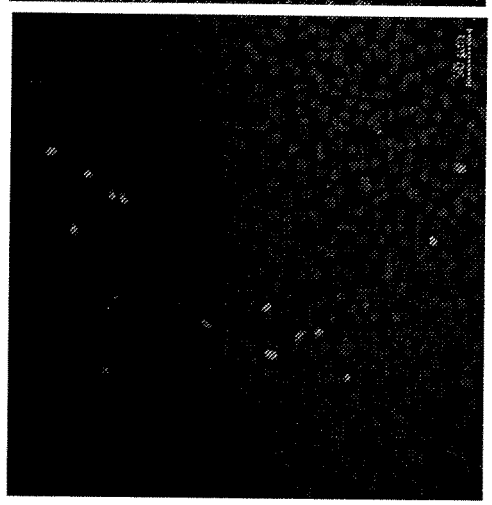
Figure 32C
Figure 32D

ADVANCED PULMONARY MODELS

TECHNICAL FIELD

The present invention relates to microfluidic fluidic systems and methods for the in vitro modeling diseases of the lung and small airway. In one embodiment, the invention relates to a system for testing responses of a microfluidic Small Airway-on-Chip infected with one or more infectious agents (e.g. respiratory viruses) as a model of respiratory disease exacerbation (e.g. asthma exacerbation). In one embodiment, this disease model on a microfluidic chip allows for a) the testing of anti-inflammatory and/or anti-viral compounds introduced into the system, as well as b) the monitoring of the participation, recruitment and/or movement of immune cells, including the transmigration of cells. In particular, this system provides, in one embodiment, an in-vitro platform for modeling severe asthma as "Severe Asthma-on-Chip." In some embodiments, this invention provides a model of viral-induced asthma in humans for use in identifying potentially effective treatments.

BACKGROUND

Effective therapies for severe asthma, in particular to reduce exacerbations that lead to hospitalization and sometimes death, are in great demand. However, advanced pre-clinical models to further elucidate underlying contributions to asthma exacerbations (and attacks) in humans are lacking because the pathogenesis is difficult to recapitulate in vitro.

Therefore, identification of new therapeutic target opportunities remains an unmet medical need, in particular for human asthmatic patients having serious medical implications, especially in younger (children) and in elderly populations.

SUMMARY OF THE INVENTION

The present invention relates to microfluidic fluidic systems and methods for the in vitro modeling diseases of the lung and small airway. In one embodiment, the invention relates to a system for testing responses of a microfluidic Small Airway-on-Chip infected with one or more respiratory viruses as a model of asthma exacerbation. In one embodiment, this disease model on a microfluidic chip allows for a) the testing of anti-inflammatory and/or anti-viral compounds introduced into the system, as well as b) monitoring/investigation of the participation, recruitment and/or movement of immune cells, including the transmigration of cells. In particular, this system provides an in-vitro platform for modeling severe asthma as "Severe Asthma-on-Chip." In some embodiments, this invention provides a microfluidic chip for us in the study of disease processes and mechanisms. In some embodiments, this invention provides a model of viral-induced asthma in humans for use in identifying potentially effective treatments.

In one embodiment, the invention provides a method of treating cells, comprising: providing a microfluidic device and respiratory cells; stimulating said respiratory cells in said microfluidic device, or stimulating said respiratory cells outside said microfluidic device, so as to create stimulated cells, said stimulated cells exhibiting a respiratory disease phenotype, wherein when said respiratory cells are stimulated outside said microfluidic device they are thereafter introduced into said microfluidic device; and contacting said stimulated cells with a microorganism or virus to create stimulated cells with a severe respiratory disease phenotype. It is not intended that the present invention be limited by the particular respiratory disease. In one embodiment, said respiratory disease phenotype is an asthma phenotype. In one embodiment, said respiratory disease phenotype is a COPD phenotype. In one embodiment, said respiratory disease phenotype is a CF phenotype. In one embodiment, said stimulated cells in said microfluidic device are subject to flow conditions, said flow conditions comprising flowing air and/or flowing culture media. In one embodiment, said stimulating comprises exposing said respiratory cells to a cytokine. In one embodiment, said cytokine is an interleukin. In one embodiment, said interleukin is IL-13. In one embodiment, said respiratory cells are in a layer on a surface of said microfluidic device. In one embodiment, said surface is part of a channel. In one embodiment, said surface is a membrane. In one embodiment, said respiratory cells are lung epithelial cells. In one embodiment, said microfluidic device comprises a channel and said respiratory cells are disposed in said channel. In one embodiment, the method further comprises measuring cell size and/or number (e.g. cell count) for at least one population of cells present in the microfluidic device. In one embodiment, the method further comprises the step of d) imaging the stimulated cells after step c). In one embodiment, the method further comprises the step of d) measuring the concentration of at least one cytokine. In one embodiment, the method further comprises the step of d) detecting hyperplasia (whether by counting cells or measuring the size of cells, or both, or by another method). In one embodiment, said hyperplasia is goblet cell hyperplasia. In one embodiment, said lung epithelial cells are on a first surface of a membrane and endothelial cells are on a second surface of a membrane. In one embodiment, the method further comprises the step of adding immune cells to said microfluidic device. In one embodiment, the method further comprises the step of measuring the extent of recruitment of said immune cells into the endothelium and/or epithelium. In one embodiment, said immune cells comprise neutrophils. In one embodiment, said stimulated cells of step b) are contacted by bacteria in step c). In one embodiment, said stimulated cells of step b) are contacted by fungi in step c). In one embodiment, said stimulated cells of step b) are contacted by a virus in step c). In one embodiment, said contacting by a virus induces viral replication on-chip. In one embodiment, said replication comprises a reinfection of cells on-chip. In one embodiment, said replication comprises infection of previously uninfected cells on-chip. In one embodiment, said stimulated cells of step b) are contacted by a respiratory virus in step c). In one embodiment, said respiratory virus is selected from the group consisting of parainfluenza virus, influenza virus, rhinovirus, coronaviruses, human respiratory syncytial virus, and adenoviruses. In one embodiment, said respiratory cells are bronchial cells. In one embodiment, said bronchial cells are mucociliary bronchiolar airway epithelial cells.

In one embodiment, the invention provides a method of treating cells, comprising: providing a microfluidic device and respiratory cells using cells that are already diseased (e.g. cells or tissues derived from a diseased patient).

In one embodiment, the invention provides a method of treating cells, comprising: providing a microfluidic device and respiratory cells derived from a patient with a respiratory disease; and contacting said respiratory cells with a microorganism or virus in said microfluidic device, or contacting said respiratory cells with a microorganism outside said microfluidic device, so as to create a severe respiratory disease phenotype wherein when said respiratory cells are contacted outside said microfluidic device they are thereafter introduced into said microfluidic device. It is not intended that the present invention be limited by the particular respiratory disease. In one embodiment, said respiratory disease phenotype is asthma. In one embodiment, said respiratory disease is a COPD. In one embodiment, said respiratory disease is a CF. In one embodiment, said respiratory cells in said microfluidic device are subject to flow conditions, said flow conditions comprising flowing air and/or flowing culture media. In one embodiment, said respiratory cells are contacted by bacteria in step b). In one embodiment, said respiratory cells are contacted by fungi in step b). In one embodiment, said respiratory cells are contacted by a virus in step b). In one embodiment, said respiratory cells are contacted by a respiratory virus in step b). In one embodiment, said respiratory virus is selected from the group consisting of parainfluenza virus, influenza virus, rhinovirus, coronaviruses, human respiratory syncytial virus, and adenoviruses. In one embodiment, said respiratory cells are bronchial cells. In one embodiment, the method further comprises measuring cell size and/or number for at least one population of cells present in the microfluidic device. In one embodiment, the method further comprises c) exposing said respiratory cells to a test agent. In one embodiment, the method further comprises the step of c) imaging the cells after step b). In one embodiment, the method further comprises the step of c) measuring the concentration of at least one cytokine. In one embodiment, the method further comprises the step of c) detecting hyperplasia (whether by counting cells or measuring the size of cells, or both, or by another method). In one embodiment, said hyperplasia is goblet cell hyperplasia In one embodiment, the invention provides a method of treating cells, comprising: providing a microfluidic device comprising a first channel and a second channel, said first channel comprising respiratory epithelial cells, said second channel comprising endothelial cells; stimulating said respiratory epithelial cells to create stimulated epithelial cells with an respiratory disease phenotype; and contacting said stimulated epithelial cells with a microorganism or vims to create stimulated epithelial cells with a severe respiratory disease phenotype. In one embodiment, said first channel is an upper channel and said second channel is a lower channel separated from said upper channel by a membrane. In one embodiment, the method further comprises exposing said respiratory epithelial cells to an air interface. In one embodiment, the method further comprises exposing said endothelial cells to culture media at a flow rate. In one embodiment, said respiratory epithelial cells are bronchial cells. In one embodiment, said bronchial cells are mucociliary bronchiolar airway epithelial cells. In one embodiment, said endothelial cells are microvascular endothelial cells. In one embodiment, the method further comprises exposing said stimulated cells to a test agent. In one embodiment, said test agent comprises a candidate drug. In one embodiment, said test agent comprises a CXCR2 inhibitor. In one embodiment, said candidate drug reduces or prevents a severe respiratory disease phenotype. In one embodiment, said test agent is a steroid. In one embodiment, said respiratory disease phenotype is an asthma phenotype. In one embodiment, said respiratory disease phenotype is a COPD phenotype. In one embodiment, said respiratory disease phenotype is a CF phenotype. In one embodiment, the method further comprises the step of detecting hyperplasia (whether by counting cells or measuring the size of cells, or both, or by another method). In one embodiment, said hyperplasia is goblet cell hyperplasia.

A method of treating cells, comprising a) providing respiratory cells derived from a patient with a respiratory disease and a microfluidic device, said microfluidic device comprising a first channel and a second channel, said first channel comprising respiratory epithelial cells, said second channel comprising endothelial cells; and b) contacting said respiratory cells with a microorganism or virus in said microfluidic device, or contacting said respiratory cells with a microorganism outside said microfluidic device, so as to create a severe respiratory disease phenotype wherein when said respiratory cells are contacted outside said microfluidic device they are thereafter introduced into said microfluidic device. In one embodiment, the method further comprises measuring cell size and/or number for at least one population of cells present in the microfluidic device.

A method of treatment, comprising: a) providing i) a patient having one or more symptoms of asthma and ii) a drug selected from the group consisting of IL-6, an IL-6 derivative, an IL-6 mimic, and an agonist of IL-6 for stimulating IL-6 production; and b) administering said drug to said patient. In one embodiment, said patient has symptoms of severe asthma. In one embodiment, said patient does not have exacerbated asthma. In one embodiment, said drug is administered as an aerosol. In one embodiment, said drug is administered by injection or by mouth. In one embodiment, said patient has a respiratory virus infection. In one embodiment, said patient has a respiratory bacterial infection. In one embodiment, said patient had at least one prior episode of asthma symptoms. In one embodiment, said patient had at least one prior episode of severe asthma symptoms.

An aerosolized formulation of a drug selected from the group consisting of IL-6, an IL-6 derivative, an IL-6 mimic, and an agonist of IL-6 for stimulating IL-6 production. In some embodiments, said formulation of said drug ranges from 1 picogram per ml to 100 nanogram per ml or more.

A drug delivery device comprising a drug selected from the group consisting of IL-6, an IL-6 derivative, an IL-6 mimic, and an agonist of IL-6 for stimulating IL-6 production, wherein said drug delivery device is configured to generate an aerosol comprising said drug. In some embodiments, said formulation of said drug is in a liquid for aerosol administration. In some embodiments, said concentration of said drug in said solution ranges from a 1picogram per ml to 100 ng per ml or more.

In one embodiment, the present invention contemplates a method of modeling disease, comprising: a) providing a fluidic device comprising living cells; b) culturing said living cells under conditions comprising flow, wherein said conditions establish a disease phenotype in said living cells; and c) contacting said stimulated cells with an irritant so as to create irritated cells. In one embodiment, said irritant is a microorganism. In one embodiment, said irritant is a virus. In one embodiment, said irritant is a dust mite. In one embodiment, said irritant is an allergen. In one embodiment, the disease phenotype is a phenotype of COPD. In one embodiment, said cells are derived from a COPD patient. In one embodiment, the disease phenotype is a phenotype of asthma. In one embodiment, said cells are stimulated with IL-13. In one embodiment, the disease phenotype is a phenotype of CF. In one embodiment, said cells are derived from a CF patient. In one embodiment, said cells a modified to include CF genotype or phenotype. In one embodiment, said living cells are lung epithelial cells. In one embodiment, said living cells are intestinal epithelial cells. In one embodiment, the said living cells are selected from the group consisting of primary cells, organoid-derived cells, a cell line, and iPS-derived cells. In one embodiment, the said living cells comprise cells modified to induce disease genotype or phenotype (e.g. in CF).

In one embodiment, the present invention contemplates a method of modeling cystic fibrosis, comprising: a) providing a microfluidic device comprising a first channel and a second channel, said first channel comprising respiratory epithelial cells, said second channel comprising endothelial cells, wherein said epithelial cells comprises cells of a cystic fibrosis genotype and/or phenotype; and b) culturing at least one of said epithelial and endothelial cells under conditions comprising flow. In one embodiment, the method further comprises c) contacting said epithelial cells with an irritant. In one embodiment, the method further comprises c) applying an agent. In one embodiment, the said epithelial cells are selected from the group consisting of patient-derived cells, organoid-derived cells, iPS-derived cells, and/or cell-lines. In one embodiment, the method further comprises testing water transport across the cell layers (improper water transport is one of the hallmarks of the CFTR mutation). In one embodiment, the method further comprises infecting the Chip with a microorganism or virus. In one embodiment, the microorganism comprises bacteria. In one embodiment, the bacteria comprise *P. aeruginosa*.

BRIEF DESCRIPTION OF THE DRAWINGS

FIG. 1A illustrates a perspective view of one embodiment of a microfluidic device with enclosed microfluidic channels (upper) with one embodiment of a microfluidic device as a CAD image (lower).

FIG. 1B illustrates an exploded view of one embodiment of a microfluidic device-showing a microfluidic channel in a top piece and a microfluidic channel in a bottom piece, separated by a membrane.

FIGS. 3A-H shows an example of human primary airway cells cultured in a microfluidic Airway-on-Chip. FIG. 3A is a schematic representation of one embodiment of an Airway-on-Chip where cells seeded in the upper channel and grown with an air interface (blue), on top of a lower channel under media flow (red). FIG. 3B shows a colored scanning electron micrograph of ciliated cells, where cilia are artificially colored blue with non-ciliated cells artificially colored brown. FIG. 3C shows a still shot (video frame) of cilia beating (blurry cilia). FIG. 3D shows an immunofluorescent micrograph of Goblet cells (red stained mucine proteins with blue colored nuclei). FIG. 3E shows a still shot from a video micrograph of mucociliary transport (i.e. mucociliary escalator) where the white dots are fluorescent microbeads moving across the upper surface of the epithelium. FIG. 3F illustrates a perspective view of one embodiment of a cross section through the Airway Chip microfluidic device with showing its two hollow linear channels (air channel above; blood channel below) separated by a porous membrane which supports growth and differentiation of human primary airway epithelial cells on its upper surface and human pulmonary microvascular endothelial cells underneath. FIG. 3G shows an exemplary scanning confocal electron micrograph of cilia forming on the differentiated airway epithelium formed on-chip (3D reconstruction showing fully differentiated, pseudostratified, airway epithelium (green, F-actin) underlined by human pulmonary endothelial cells (red, F-Actin)). FIG. 3H shows an exemplary differentiated human airway epithelium exhibiting continuous tight junctional connections on-chip, as evidenced by ZO1 staining in red enclosing the cells in black.

FIGS. 4A-F shows an example of human Rhinovirus replicating in one embodiment of the microfluidic Airway-on-Chip. FIG. 4A is an exemplary graph of a growth curve of the virus showing replication inside of the microfluidic Airway-on-Chip over a period of 6 days, with high amounts of virus released from cells (and by disintegrating dying cells) within 24 hours. Infected chips (n=3) were washed apically daily and replicating virus was quantified. HRV 16 Titer (Log 10 TCID 50/mL) vs Time post infection (hours); FIG. 4B shows phase contrast images of Non-infected (control) cells observed at the same time as the post 24 infected cells (i.e. Non infected—24 hpi). Infected chips display high apical cell sloughing. FIG. 4C shows rhinovirus-infected HRV-16 cells in an Airway-on-Chip. Note the rounded cells sloughing off the epithelium in the infected cultures, example shown at the white arrow head (HRV-16-24 hpi); FIG. 4D shows identification of dying cells in the chip. The vast majority of cells shown here damaged by the infection are ciliated (green staining). Most of these ciliated cells are also infected with HRV-16 (red staining) e.g. cell identified by a thick white arrow while an e.g. of another cell type is identified by a thin white arrow. Nuclei are shown in blue. (24 hpi). A blue arrow points to a rounded cell filled with virus located in the cell cytoplasm. Confocal imaging of detached apical cells showing that most detached cells are HRV-infected ciliated cells, suggesting that HRV primarily infects multiciliated cells; FIG. 4E shows exemplary confocal imaging of detached apical cells (from washing the apical surface) showing that most detached cells are HRV-infected ciliated cells, suggesting that HRV primarily infects multiciliated cells and FIG. 4F shows HRV-16 infection induced cytopathic effects in one embodiment of an Airway Chip. Immunofluorescence staining shows TUNEL positive (apoptotic) cells in apical washes of HRV-infected chips.

FIGS. 5A-E shows an example of human Rhinovirus specifically damaging ciliated cells. FIG. 5A is a micrograph of fluorescent imaging of ciliated cells (stained cilia are shown in green with stained cell nuclei shown in blue) before (left) and after Rhinovirus infection (right) 6 days after infection (6d: 6 dpi). Note the large amounts of cilia in the left panel as opposed to the almost total destruction of ciliated cells at the end point of the infection in the right panel. Examples of ciliated cells are identified by white arrows. FIG. 5B shows a graphical representation of the area covered by ciliated cells before and after infection. Ciliated cells (% total area) comparing non infected to HRV-16 infected chips. FIG. 5C shows graphical quantification of the length of cilia before and after infection. Note that after infection cilia are very small compared with before infection. This graph shows cilia length in pixels comparing non-infected to HRV-16 infected cells. FIG. 5D shows Rhinovirus infecting ciliated cells (24 hours pi) but not detected in mucus producing cells. In fact, infected ciliated cells were observed to protrude from the epithelial surface while cilia beating frequency was reduced following infection. Upper left image shows bright green (white) labeling of beta-tubulin in ciliated cells having co-localized monoclonal (m) antibody (Ab) J2 (mabJ2) staining in red (darker areas) show locations of double-strand RNA indicative of viral replication in infected ciliated cells. DAPI stained and blue colored nuclei show in the darkest staining. Upper left image shows bright green (white) labeling of MUCSAC in goblet cells that do not appear to be co-localized with monoclonal (m) antibody (Ab) J2 (mabJ2) staining in red (darker areas) showing locations of double-strand RNA indicative of viral replication. DAPI stained and blue colored nuclei show in the darkest staining. Below each image is a cross-sectional fluorescent image of the epithelial cell layer showing (left) the presence of virus in a ciliated cell as staining positive for beta-tubulin, see white arrow, while the right lower image shows viral staining, red, that is not associated with the MUC5AC staining of goblet cells. FIG. 5E shows an exemplary result of cilia beating frequency (Hz) being significantly reduced following infection.

FIG. 6A shows cells at 24 h post infection: Pink arrows point to examples of rounded ciliated cells. Note the rounded cells moving (blurry) due to cilia beating. These cells are predicted to detach from the epithelium layer/membrane. FIG. 6B shows quantification of cilia beat frequency between non-infected and HRV-16 infected chips. Cilia beating frequency(Hertz: Hz) comparing frequency measured in non-infected to infected chips.

FIGS. 7A1-4-B1-5 shows embodiments for modeling asthma exacerbation on chip by measuring cilia beating frequency and mucociliary transport on-chip for modeling changes in function of Human Airway Epithelium. Although IL-13 stimulation also reduces cilia beating frequency but do not sensitize the epithelium to rhinovirus. FIG. 7A shows a panel of micrographs along with a CBF (cilia beating frequency) (HZ) colorized scale demonstrating cilia beating in FIG. 7A1, a colorized cilia beating frequency micrograph FIG. 7A2 using a CBF scale shown in FIG. 7A3. FIG. 7A4 shows a still shot from a video micrograph of mucociliary transport (i.e. mucociliary escalator) where the white dots are fluorescent microbeads moving across the upper surface of the epithelium. FIG. 7B1-7B2 shows a panel of micrographs demonstrating cilia beating frequency in colorized micrographs a CBF scale shown in FIG. 7B3. FIG. 7B4 shows a chart of cilia beating frequency (Hz). FIG. 7B5 shows comparative HRV-16 viral titers (Log10 TCID50/ml) showing little difference in amount of virus produced in IL-13 co-treatments.

FIG. 8A is a micrograph showing fluorescent imaging of mucus producing cells (Goblet cells (MUCSAC+)-red) before of after (6 days) infection. Note that after infection almost all the cells are goblet cells, typical of a goblet cell hyperplasia/metaplasia. MUC5AC staining also suggests increase of apical mucus secretion. Nuclei are shown in blue.

FIG. 8B shows quantification of the goblet cells hyperplasia/metaplasia after infection (6 days). Goblet cells (% total area) vs. comparing non infected to HRV-16 infected chips. FIG. 8C shows pro-inflammatory chemokines secreted following HRV-16 infection. CXCL10 is secreted upon Interferon stimulation. MIP-1 a and MCP-1 are chemoattractants for neutrophils. CXCL10 (pg/mL) MIP-1α (pg/mL) MCP-1 (pg/mL). Comparing non-infected to HRV-16 infected chips at 24 hpi (hours post infection) and 48 hpi. FIG. 8D demonstrates exemplary immunofluorescence staining showing chromatin condensation in nuclei of HRV-infected cells. HRV-16 virions are shown in red. Nuclei stained with DAPI are shown in blue.

FIGS. 9A-B shows an example of one embodiment of an Airway-on-Chip inducing an asthma-like phenotype using IL-13 stimulation. Creation of a Th2 microenvironment through IL-13 stimulation induces an asthma-like phenotype in the Airway Chip. Exacerbation is then triggered by infecting with human rhinovirus 16. FIG. 9A is a schematic illustration showing IL-13 in the context of an Airway-on-Chip, where IL-13 effects both epithelial cells in the upper channel with an air interface and endothelial cells in the lower channel under flow (left). Another schematic (right) shows additional detail of a mucociliary airway epithelium (ciliated blue cells and pink large goblet cells) in the process of being contacted (infected) with an exemplary respiratory virus at an MOI of 1 (green dots) in the epithelial channel, where a membrane separates the epithelial channel from the endothelial cells in the vascular channel. IL-13 is added to the endothelial channel at an exemplary 100 ng/ml for an exemplary 7 days. FIG. 9B shows effects of IL-13 on epithelial cells: IL-13 induces goblet cells hyperplasia as shown in micrographs of immunostained cells. No treatment, IL-13 treatment, IL-13+Dex (dextran) and IL-13+Tofacitinib. MUC5AC (Mucin 5AC, Oligomeric Mucus/Gel-Forming) (green) and cell nuclei are stained with DAPI (4',6-diamidino-2-phenylindole) as shown in blue. FIG. 9C shows effects of IL-13 on endothelial cells: a graphical measurement of gene expression over time compared to non-treated cells shows that IL-13 up regulates adhesion proteins such as Selectins (P and E) and ICAM-1 and VCAM-1 graphed as IL-13-induced gene expression changes (Fold over non-treated vs. agent added to chip). Other compounds tested included Interleukin alpha (IL1A), Interleukin beta (IL1B), Interleukin-6 (IL6), Interleukin-8 (IL8), The chemokine (C-C motif) ligand 2 (CCL2), C-C Motif Chemokine Receptor 4 (CCR4), Protein Tyrosine Phosphatase, Receptor Type C (PTPRC), Intercellular Adhesion Molecule 1 (ICAM1), Selectin P (SELP), Selectin E (SELE), Prostaglandin-Endoperoxide Synthase 2 (PTGS2), Transforming Growth Factor Beta 1 (TGFB1), SMAD Family Member 7 (SMAD7), Complement C3 (C3), Angiotensin I Converting Enzyme (ACE), cluster of differentiation 34: CD34 antigen: CD34 molecule (CD34) and Nuclear Factor Of Activated T-Cells 4 (NFATC4).

FIG. 10A. Shows an exemplary One step growth curves of HRV-16 (MOI=2) in infected Airway chips treated with IL-13 or not. No differences in growth were noted when chips were treated with IL-13. FIG. 10B demonstrates exemplary graphs showing apical interferon response following IL-13 treatment and HRV-16 infection of Airway Chips at 24 h and 48 h post infection. Quantification of interferon response shows that IL-13 treatment alter type I and III interferon and interferon stimulated genes CXCL10 and CXCL11 during HRV-16 infection.

FIG. 11B shows corresponding basal secretion.

FIG. 12B shows corresponding basal secretion.

FIGS. 13A-C shows exemplary inflammatory response in an Airway-on-Chip model of asthma. In one embodiment, an asthma phenotype was generated using IL-13 stimulation. This stimulation led to the activation of human endothelium at 48 hours of treatment. IL-13 induces vessel (endothelial cell) wall priming as part of recruitment of immune cells. FIG. 13A demonstrates log10 significance differences including p values, at horizontal dotted lines, after staining for endothelial cell proteins vs. differences on a Log2 basis between IL-13 induced cells and a control without treatment with IL-13. FIG. 13B shows effects of IL-13 on endothelial cells: as shown in micrographs of immunostained cells: increased adhesion molecule expression was observed. IL-13 100 ng/mL (right panels) vs. no treatment controls (left panels) VE-Cadherin (red), ICAM-1 (green) in the upper panels. VCAM-1 (red) VE-Cadherin (green). Cell nuclei are stained with DAPI (4',6-diamidino-2-phenylindole) as shown in blue. FIG. 13C shows quantitative charts of comparative ICAM-1 (upper chart) and VCAM-1 (lower chart) significant induction vs. controls.

FIGS. 14A-C shows an example of one embodiment of an Airway-on-Chip emulating acute asthma exacerbation by combining Rhinovirus infection with IL-13 stimulation in the presence of an exemplary immuno-modulatory compound: Neutrophil recruitment following exacerbation with HRV can be reduced by an exemplary CXCR2 antagonist MK-7123. FIG. 14A (upper image) shows one embodiment of an Airway-on-Chip that enables testing of immunomodulatory compounds, e.g. for neutrophil recruitment, in a model of acute asthma exacerbation. HRV-16 is represented as small green dots in the upper channel while neutrophil cells (also described as polymorphonuclear leukocytes (PMN)) are represented as large purple spots in the lower channel. An enlarged schematic is demonstrated schematically in the lower image showing a HRV-infected Airway Chip during perfusion in the vascular channel of freshly isolated human neutrophil. FIG. 14B shows a series of fluorescent micrographs showing comparisons of stained neutrophil cells (red) recruited to the endothelium and attached to non-treated cells. Treatments included HRV-16 alone infected cells, IL-13 alone treated cells, HRV-16 and (+) IL-13 treated cells, HRV-16+CXCR2in (inhibitor) treated cells, and HRV-16+IL-13+CXCR2in. Non-stimulated chips are showing limited neutrophil recruitment while HRV infected and IL-13-treated chips show increased neutrophil recruitment. IL-13+HRV induce an additive increase in neutrophil recruitment, while treatment with a CXCR2 antagonist. MK-7123 (10 microM) significantly reduced neutrophil recruitment under three stimulation conditions. FIG. 14C is a graphical comparison showing PMN (neutrophil) cells counts as % of untreated cells and cells treated with combinations shown for IL-13, HRV, and CXCR2 (in) treatments. Quantification of neutrophil recruitment (* * p<0.01; * * * * p<0.001).

FIG. 15A is a micrograph showing effects of HRV-16 infected cells (24 hpi) on cell attachment and FIG. 15B shows effects of HRV-16 infected cells (24 hpi) treated with CXCR2in (10 µM) on cell attachment. FIG. 15C shows a graph of the number of spots (i.e. neutrophil cells: N spots) counted over time (up to 300 seconds) for HRV-16 infected cells (24 hpi). FIG. 15D shows a graph of N spots counted over time (up to 600 seconds) for HRV-16 infected cells (24 hpi) treated with CXCR2in (10 µM).

FIGS. 16A-F show exemplary schematics and data, showing viral-induced exacerbation on-chip inducing neutrophil transmigration, for use in on-chip testing of prophylactic treatments for reducing incidents of severe asthma attacks and for treatments during severe asthma attacks to reduce at least one symptom. FIG. 16A shows an exemplary schematic (as a Venn Diagram) where asthma induction as an inflamed airway is represented by IL-13 treatment (left circle) and viral exacerbation of asthma is represented by a rhinovirus (HRV) infection (right circle). The area of overlap represents asthma exacerbation in a patient or on-chip when both conditions are present. FIG. 16B shows an exemplary schematic of one embodiment of asthma exacerbation where a virus is infecting ciliated epithelial cells in the airway channel (green dots and green ciliated cells) which induces neutrophil (bumpy round cells) recruitment (attachment) and movement through the endothelium on the vascular channel, then as shown in FIG. 16C, neutrophils show extravasation through the porous membrane then into the airway side of the membrane, i.e. trans-epithelial migration. FIG. 16D shows one embodiment of a severe asthma chip enabling neutrophil diapedesis: HRV16 (24 hpi) infected cells visualized by immunofluorescent staining of Myeloperoxidase (MPO) stained neutrophils showing a Z-stack confocal microscopic image. FIG. 16E shows a colorized immunofluorescent image of HRV16 (24 hpi) infected cells stained with Myeloperoxidase (MPO) (green)/mAbJ2 (red)/DAPI (blue) where MPO+ cells are located near virally infected cells. And FIG. 16F shows a monoclonal antibody (mabJ2) (mouse) detecting double-strand RNA as an RNA replication-center assay for one embodiment of a high content image-based quantification of human rhinovirus and Coxsackie virus infections.

FIG. 17A-C HRV-16-induced interferons, chemokines and pro-inflammatory cytokines profile is altered by IL-13 treatment in one embodiment of a severe asthma on-chip. These exemplary graphs show results from high resolution, kinetic profiles of an IFN Lambda 1 response FIG. 17A; IP-10/CXCL10 FIG. 17B; IL-6 response FIG. 17C; following HRV16 infection. A severe asthma on-chip was stimulated with IL-13 (lower red line and squares) while a duplicate chip was not stimulated with IL-13 (upper blue line and circles). IL-13 treatment was over 72 hours post infection. Data represent mean±SEM of cells from three to four different donors, with one or two biological replicates (chips) per donor.

FIGS. 19A-B shows exemplary infection of one embodiment of an Airway Chip with bacteria *Moraxella catharalis* (MC), two different strains used at MOI 10 ($10^6$ CFU per chip) at 24 post-infection (hpi). Bacteria are labeled in green. Biofilm formation (including biofilm-like structures and microcolonies) is observed on top of epithelial cells. We showed that it is possible to infect the Airway Chip with bacterial pathogens for several days. FIG. 19A MC ATCC strain. FIG. 19B MC clinical isolate strain isolated from a human patient.

FIG. 20A PA 5919-WT. FIG. 20B PA 5890-Mutant. Left: Alexa fluor 488-anti-*P. aeruginosa* (Pa) antibody. Central: Bright-field. Right: Alexa fluor 488-anti-*P. aeruginosa* (Pa) antibody-Bright-field.

FIG. 21A PA 5919-WT. Actin (red); Pa (green); DAPI (blue). FIG. 21B PA 5890-Mutant. Actin (pink); Pa (green); DAPI (blue). Images were acquired 24 hpi. FIG. 21C shows a confocal immunofluorescent micrograph side view of a cell layer infected with *P. aeruginosa* in a microfluidic airway chip, 24 hours post infection. Actin (pink); Pa (green); DAPI (blue). Bacterial aggregates on apical surface as well as intracellular bacteria are observed.

FIG. 22A shows non-infected control microfluidic chip image representing beating cilia. FIG. 22B PA 5890 shows Mutant infected microfluidic chip image representing loss of beating cilia. FIG. 22C PA 5919 shows WT microfluidic chip image also representing a loss of beating cilia.

FIG. 26A shows exemplary Imipenem (Merck compound) effects on *P. aeruginosa* infection in a Transwell culture. FIG. 26B Imipenem treatment reduces total bacterial counts via bacterial killing in one embodiment of a *P. aeruginosa* infection on chip. Two-way ANOVA with Dunnett's post-test <0.05, <0.001 (compared to untreated).

FIG. 27A shows exemplary Imipenem treatment. FIG. 27B shows exemplary Carbenicillin treatment. FIG. 27C shows exemplary Tetracycline treatment. Two-way ANOVA with Dunnett's post-test <0.05, <0.001, *** <0.0001 (compared to untreated).

FIGS. 28A-C shows exemplary real time imaging of Imipenem effects on *P. aeruginosa* infection on one embodiment of a PA 5919 WT *Pseudomonas* infection on chip. *P. aeruginosa* infection shown on chip with WT strain (green). FIG. 28A shows an untreated, infected control. FIG. 28B shows infection on-chip treated with 50 µg/ml Imipenem. FIG. 28C shows infection on-chip treated with 500 µg/ml Imipenem for 24 h. There is an obvious reduction in bacterial load indicated by the reduction in fluorescent bacteria as shown by live imaging. Imipenem effect is demonstrated by bacterial killing and control of infection. PA 5919 WT 24 hpi. Left: Alexa fluor 488-anti-*P. aeruginosa* (Pa) antibody. Central: Bright-field. Right: Alexa fluor 488-anti-*P. aeruginosa* (Pa) antibody-Bright-field.

FIG. 28A untreated (noninfected) control. FIG. 28B infection treated with 50 ug/ml imipenem. FIG. 28C infection treated with 500 ug/ml imipenem for 24 h. PA 5890 Mutant 24 hpi. Left: Alexa fluor 488-anti-*P. aeruginosa* (Pa) antibody. Central: Bright-field. Right: Alexa fluor 488-anti-*P. aeruginosa* (Pa) antibody-Bright-field.

FIG. 30A shows an exemplary infection of Sp at MOI 1. F-actin immunostain shown in red; B-tubulin immunostain shown in purple; Bacteria immunostain shown in green. Cell nuclei DAPI stained and shown in blue. FIG. 30B shows an exemplary infection of Sp at MOI 10. F-actin immunostain shown in red; MUC5AC immunostain shown in yellow; Bacteria immunostain shown in green. Cell nuclei DAPI stained and shown in blue.

FIGS. 32A-D shows exemplary apoptosis via TUNEL staining at 24 h post infection. Apoptotic, TUNEL+, (pink); nuclei, DAPI+, (blue). FIG. 32A uninfected; FIG. 32B Pa infected; FIG. 32C staurosporin treatment. Staurosporin refers to an ATP-competitive kinase inhibitor. FIG. 32D DNAse I treatment. DNAse I refers to an endonuclease that nonspecifically cleaves DNA to release di-, tri- and oligonucleotide products with 5'-phosphorylated and 3'-hydroxylated ends. DNase I acts on single- and double-stranded DNA, chromatin and RNA:DNA hybrids.

DEFINITIONS

Figure 2:
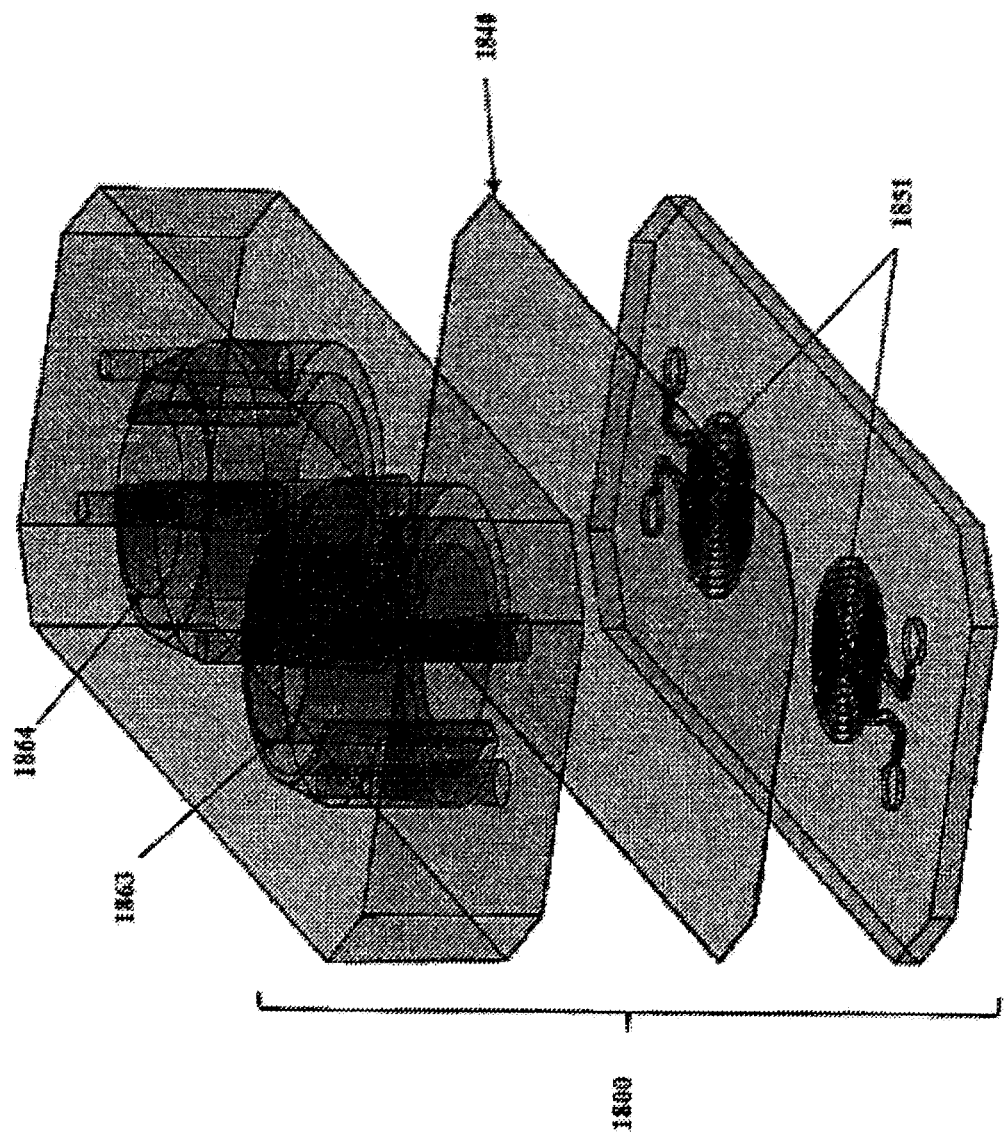
FIG. 2 shows an exemplary schematic of a microfluidic device with the lid removed ("open top") comprising two chambers with microfluidics underneath.

As used herein, "asthma" refers to a condition or disease that affects the airways of lungs. As an example, asthma typically results in episodes or attacks with symptoms including but not limited to breathlessness, chest tightness and wheezing.

As used herein, "stimulation" or "stimulated" refers to airway cells being treated in a manner that alters their phenotype from a healthy phenotype to cells exhibiting a respiratory disease phenotype, including but not limited to, changes in cytokine expression, for non-limiting examples, increasing IL-1alpha, IL-6 production; and/or changes in adhesion molecule expression, for non-limiting examples, increasing (up regulating) adhesion proteins, such as Selectins (P and E) and ICAM-1, VCAM-1, VE-Cadherin, etc. Stimulation includes but is not limited to treatment of airway cells with a stimulation agent, including but not limited to a cytokine, such as IL-13; infection of healthy cells with a microbe or virus; acute and chronic exposures to aerosolized allergens, such as pollen; tobacco/cigarette smoke, etc. Thus, depending upon the context, "stimulation" in reference to generating an underlying disease model (e.g. IL-13 stimulation of respiratory cells for generating an asthma phenotype) refers to generating a disease phenotype whereas "stimulation" in reference to exacerbation (e.g. viral stimulation of respiratory cells having an asthma phenotype) refers to inducing a severe disease phenotype.

As an alternative to stimulating airway cells, cells may be derived from a patient or have induced genetic changes to create a disease background. As one non-limiting example, the present invention contemplates inducing a CF background by transforming airway cells with a gene(s) having a known association with CF.

As used herein, "exacerbation" in reference to stimulated airway cells refers to onset of a "severe" respiratory disease phenotype, including but not limited to "severe" respiratory disease on-a-chip. Such "severe" respiratory disease on-a-chip includes but is not limited to "Severe Asthma-on-a-Chip", "Severe Cystic Fibrosis-on-a-Chip", "Severe Chronic Obstructive Pulmonary Disease-on-a-Chip", etc. For example, stimulated airway cell layers demonstrating an inflammatory phenotype, such as by using treatment with IL-13 or asthma cells derived from a patient, can be further treated wherein the airway cells are also infected with (or exposed to) at least one agent (whether microbial or viral) for creating a "severe" respiratory disease on-a-chip "Severe Asthma-on-a-Chip".

More specifically, and for an example, a "Severe Asthma-on-a-Chip" refers to a small airway chip having stimulated airway cells, wherein a co-factor, including but not limited to other stimulation agents, such as infection by at least one or more microbial agents, such as a respiratory virus, bacteria, fungi, induces exacerbation of, i.e.-worsening of, asthmatic phenotypic effects, including but not limited to altered phenotypes and/or markers, such as increased PMN infiltration, goblet cell hyperplasia, increased mucus production, altered mucus composition, decreased rates of muco-cilary (mucocilary) transport, lower rates of beating cilia, increased rates of cells sloughing off of epithelial layers, etc. Altered markers are not intended to be limited to these examples, and may include changes in cytokine production, such as lowered expression of IFNalpha2; changes in cytokine receptor expression, etc.

As used herein, a "Severe Cystic Fibrosis-on-a-Chip" or a "Severe CF-on-a-Chip" refers to exacerbation of "Cystic Fibrosis-on-a-Chip."

As used herein, a "Severe Chronic Obstructive Pulmonary Disease-on-a-Chip" or a "Severe COPD-on-a-Chip" refers to exacerbation of "Chronic Obstructive Pulmonary Disease-on-a-Chip."

As used herein, "asthma attack" refers to a sudden worsening of asthma symptoms caused in part by tightening of muscles around airways (i.e. bronchospasms), increased amounts of mucus in addition to swollen/inflamed linings of the airway. Attacks range from mild to severe and may occur as intermittent attacks or as persistent attacks. An acute, or sudden, asthma attack is usually caused by an exposure to allergens or an upper respiratory tract infection.

As used herein, "respiratory virus" refers to a virus capable of infecting cells in the respiratory system, such as bronchial epithelial cells, examples including but not limited to parainfluenza virus, influenza virus, rhinovirus, coronaviruses, human respiratory syncytial virus, adenoviruses, etc.

As used herein, "parainfluenza virus" or "PIV" refers to a virus that can cause both upper and lower respiratory infections including colds, bronchiolitis, bronchitis, croup and pneumonia. PIV-1 and PIV-2 are common causes of croup, whereas PIV-3 often causes lower respiratory tract infections (LRIs), such as bronchiolitis and pneumonia. Human parainfluenza virus may be referred to as "HPIV."

As used herein, "rhinovirus" refers to any virus of a group of picornaviruses, including those that cause some forms of the common cold.

As used herein, "flu" refers to an infectious disease caused by an influenza virus in addition to other "flu-like" viruses, characterized by symptoms such as fever, muscle pain, headache, and inflammation of the mucous membranes in the respiratory tract.

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels. Examples of microfluidic devices with microfluidic channels are provided in U.S. Pat. No. 8,647,861, hereby incorporated by reference in its entirety.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid source such as a fluid reservoir. Two components may be coupled to each other even though they are not in direct contact with each other. For example, two components may be coupled to each other through an intermediate component (e.g. tubing or other conduit).

An "aerosol" is herein defined as a suspension of liquid or solid particles of a substance (or substances) in a gas. The term "charge" is used to describe the amount of drug placed into the delivery system. "Inhaled mass" refers to the actual amount inhaled by the patient. "Deposition" refers to the dose actually deposited in the patient. The "charge" may be high depending on device efficiency. Even with low efficiency delivery, good control over delivery (reproducible over a small range) is preferred as the means of controlling dose.

The present invention contemplates the use of both atomizers and nebulizers of various types. An "atomizer is an aerosol generator without a baffle, whereas a "nebulizer" uses a baffle to produce smaller particles. However, the term "nebulizer" in the claims is meant to encompass atomizers.

In one embodiment, the present invention contemplates using the commercially available Aerogen™ aerosol generator which comprises a vibrational element and dome-shaped aperture plate with tapered holes. When the plate vibrates several thousand times per second, a micro-pumping action causes liquid to be drawn through the tapered holes, creating a low-velocity aerosol with a precisely defined range of droplet sizes. The Aerogen™ aerosol generator does not require propellant.

"Baffling" is the interruption of forward motion by an object, i.e. by a "baffle." Baffling can be achieved by having the aerosol hit the sides of the container or tubing. More typically, a structure (such as a ball or other barrier) is put in the path of the aerosol (See e.g. U.S. Pat. No. 5,642,730, hereby incorporated by reference in its entirety, and in particular see, FIG. 6, element 6 of this patent). The present invention contemplates, in one embodiment, the use of a baffle in order to slow the speed of the aerosol as it exits the delivery device.

A "dose metering element" is an element that controls the amount of drug administered. The element can, but need not, measure the amount of drug as it is administered. In a preferred embodiment, the element is characterized simply as a container of defined volume (e.g. a reservoir). In a preferred embodiment, the defined volume is filled by the manufacturer or hospital professional (e.g. nurse, pharmacist, doctor, etc.) and the entire volume is administered. In another embodiment, the reservoir is configured as a transparent or semi-transparent cylinder with visible measurement indicia (e.g. markings, numbers, etc.) and the filling is done to a desired point (e.g. less than the entire capacity) using the indicia as a guide.

A "fluid driving element" is an element that moves fluid in a direction along the device. In simple embodiments, the fluid driving element comprises a plunger driven by compressed gas, said compressed gas stored in a canister. In other embodiments, it comprises a pump. In still other embodiments, it comprises a hand actuated plunger (in the manner of a syringe).

As used herein, "agonist" refers to a substance that initiates the same reaction or activity typically produced by the binding endogenous substance when combined with a receptor. As one example, an IL-6 agonist simulates IL-6 activity. Examples of IL-6 agonists include but are not limited to soluble receptors sIL-6R, Epstein-Barr virus-induced gene 3 (EBI3), and sCNTF-R of the IL-6 family, see, Scheller, et al., "The pro- and anti-inflammatory properties of the cytokine interleukin-6." Biochimica et Biophysica Acta (BBA)—Molecular Cell Research, 1813(5): 878-888, 2011.

As used herein, "TCID" refers to an assay procedure performed to determine the infectious titer of any virus which can cause cytopathic effects (CPE) in tissue culture over a reasonable period of days while cells in culture remain viable. More specifically, "$TCID_{50}$" refers to amount of a pathogenic agent that will produce pathological change in 50% of cell cultures inoculated.

As used herein, the term "microorganism" includes but is not limited to bacteria, viruses, fungi, phage, and symbiotic organisms.

DESCRIPTION OF INVENTION

The present invention relates to microfluidic fluidic systems and methods for the in vitro modeling diseases of the lung and small airway. In one embodiment, the invention relates to a system for testing responses of a microfluidic Small Airway-on-Chip infected with one or more respiratory agents (such as viruses) as a model of respiratory disease exacerbation (e.g. asthma exacerbation). In one embodiment, this disease model on a microfluidic chip allows for a) the testing of-anti-inflammatory and/or anti-viral compounds introduced into the system, as well as b) monitoring the participation, recruitment and/or movement of immune cells, including the transmigration of cells. In particular, this system provides an in-vitro platform for modeling severe asthma as "Severe Asthma-on-Chip." In some embodiments, this invention provides a model of viral-induced asthma in humans for use in identifying potentially effective treatments.

New therapies for severe asthma, particularly treatments that reduce exacerbations, remain a significant unmet medical need. Development of advanced pre-clinical models are needed to further elucidate the complex mechanisms underlying asthma exacerbation and investigate new therapeutic strategies.

At least one embodiment of a 3D microphysiological human Small Airway-on-Chip was designed and tested during the development of the present invention, in part for meeting at least one unmet medical need. A Small Airway-on-Chip contained a fully differentiated mucociliary bronchiolar airway epithelium cultured at an air liquid interface underlined by a microvascular endothelium under dynamic fluid-flow.

A Microfluidic Airway-on-Chip Enables Physiological Differentiation of Human Airway Epithelial Cells.

One embodiment of an Airway-Chip was designed to study human respiratory diseases where the epithelium plays a central role (e.g., Chronic Obstructive Pulmonary Disease (COPD)). One embodiment of a microfluidic Airway-on-Chip, described herein, enables physiologically relevant differentiation of human airway epithelial cells. For one example, human primary airway cells cultured in a microfluidic Airway-on-Chip differentiated into epithelium, and in cell compositional ranges similar to in vivo airways, e.g. ciliated epithelial cells (approximately (~) 20-30%), Goblet cells (approximately 10-20%) and basal cells (approximately 20%). In general, goblet cells refer to column-shaped cell, found in the respiratory and intestinal tracts, which secrete gel-forming mucins, as major components of mucus. In general, basal cells refer to a type of cell in the innermost layer of an epithelial tissue.

Ciliated cells in the chip are similar to those in vivo as they show similar cilia structure, e.g. length, parts, (i.e.

axonemes, referring to the central strand of a cilium or flagellum, composed of an array of microtubules, typically in nine pairs around two single central microtubules) and function, (i.e. beating at frequency rates estimated as similar to cilia movements in vivo). See Tables 1A-1B.

Moreover, Goblet cells produce mucus that moves over the surface of the epithelium as part of mucociliary transport. For example, mucociliary velocity in the Airway-on-Chip is 40-100 µm/sec., within the range of velocity measured in humans. See FIG. 3A-H.

TABLE 1A

One embodiment of a microfluidic Airway-on-Chip emulates human airway physiology.

| Parameters | In Humans (in vivo) References are indicated in parenthesis. | In microfluidic Airway-on-Chip (in vitro) |
|---|---|---|
| Cilia beating frequency | 9-20 Hz (1-2) | 9-19 Hz |
| Cilia length | ~6 µm (1-2) | ~6 µm |
| Axoneme structure | 9 + 2 microtubule (1-2) | 9 + 2 microtubule |
| Mucociliary velocity | 40-150 µm/sec (2) | 40-100 µm/sec |
| % of ciliated cells | ~30% (4) | ~20-30% |
| % of goblet cells | ~10-15% (3-4) | ~10-20% |
| % of basal cells | ~6-30% (3-4) | ~20% |

References: 1) Livraghi, et al., "Cystic fibrosis and other respiratory diseases of impaired mucus clearance." Toxicol Pathol, 35(1):116-29, 2007, 2) Wanner, et al, 1996 3) Boers, et al., "Number and proliferation of neuroendocrine cells in normal human airway epithelium." Am J Respir Crit Care Med. 154:758-63, 1999 and 4) Mercer, et al, "Cell number and distribution in human and rat airways." Am J Respir Cell Mol Biol. 10(60):63-24, 1994.

TABLE 1B

One embodiment of a microfluidic Airway-on-Chip emulates human airway physiology.

| Parameters | Human airway | Airway Chip (±SD) |
|---|---|---|
| Cilia beatinq frequency (Hz) | 9-20 (Refs. 1-2) | 16.35 (±2.6) |
| Mucociliary velocity (µm/s) | 40-150 (Ref. 2) | 103.5 µm/s (±46.1) |
| Goblet cells (%) | ~10-15 (Refs. 3-4) | 18.4 (±1.2) |
| Basal cells (%) | ~6-30 (Refs. 3-4) | 10.4 (±3.8) |

References: (1) Am. J. Respir. Crit. Care Med. 15 4, 1868-1902 (1996); (2) Toxicol Pathol, 35:116-29 (2007); (3) Am. J. Respir. Crit. Care Med. 159, 1585-1591 (1999); (4) Am. J. Respir. Cell Mol. Biol. 10, 613-624 (1994).

Thus a microfluidic Airway-on-Chip provides a model for studying infectious disease effects on human airway cells in vitro, such as their effects on developing respiratory conditions, such as pre-asthma, pre-COPD, etc., for effects on pre-existing respiratory conditions (e.g. asthma, COPD, etc.), for effects on respiratory conditions (e.g. asthma, COPD, etc.), and further for infectious disease effects on exacerbating respiratory conditions, e.g. severe asthma.

FIG. 3A-H shows an example of human primary airway cells cultured in a microfluidic Airway-on-Chip. FIG. 3A is a schematic representation of one embodiment of an Airway-on-Chip where cells seeded in the upper channel and grown with an air interface (blue), on top of a lower channel under media flow (red). FIG. 3B shows a colored scanning electron micrograph of ciliated cells, where cilia are artificially colored blue with gobs of mucus artificially colored brown. FIG. 3C shows a still shot (video frame) of cilia beating (blurry cilia). FIG. 3D shows an immunofluorescent micrograph of Goblet cells (red stained muccal proteins with blue colored nuclei). FIG. 3E shows a still shot from a video micrograph of muco-ciliary transport where the white dots are mucus globs moving across the upper surface of the epithelium. The Airway Chip described herein, recapitulates the physiology and function of the airway epithelium that conduct inhaled air to the alveolar air sacs. FIG. 3F illustrates a perspective view of one embodiment of a cross section through the Airway Chip microfluidic device with showing its two hollow linear channels (air channel above; blood channel below) separated by a porous membrane which supports growth and differentiation of human primary airway epithelial cells on its upper surface and, human pulmonary microvascular endothelial cells underneath. FIG. 3G shows an exemplary scanning confocal electron micrograph of cilia forming on the differentiated airway epithelium formed on-chip (3D reconstruction showing fully differentiated, pseudostratified, airway epithelium (green, F-actin) underlined by human pulmonary endothelial cells (red, F-Actin)). FIG. 3H4 shows an exemplary differentiated human airway epithelium exhibiting continuous tight junctional connections on-chip, as evidenced by ZO1 staining in red enclosing the cells in black.

When infected with human Rhinovirus (HRV), a leading cause of asthma exacerbation in children and adults, the Airway Chip demonstrated induction of a pro-inflammatory response characterized by ciliated cell deaths, goblet cell hyperplasia and release of cytokines including IFN-α2, IFN-λ1, CXCL10 and CXCL11, as well as recruitment and extravasation across the endothelium of circulating human neutrophils. Treatment of the Small Airway on-Chip with a TH2 cytokine IL-13, reconstituted an in vivo relevant release of pro-inflammatory cytokines, hyperplasia of goblet cells and reduced cilia beat frequency representative of an asthma-like medically relevant phenotype.

As an exemplary immuno-modulatory compound, addition of IL-13 to an Airway-on-Chip induced changes in epithelial cell layers in the upper channel with an air interface and endothelial cells in the lower channel under media fluid flow conditions are shown. It was discovered that IL-13 added to this embodiment of Airway-on-Chip effects both the epithelial cell layer in the upper channel with an air interface and the endothelial cells in the lower channel under media flow conditions. FIG. 9A is a schematic illustration showing IL-13 in the context of an Airway-on-Chip, where IL-13 effects both epithelial cells in the upper channel with an air interface and endothelial cells in the lower channel under flow (left). Another schematic (right) shows additional detail of a mucociliary airway epithelium (ciliated blue cells and pink large goblet cells) in the process of being contacted (infected) with an exemplary respiratory virus at an. MOI of 1 (green dots) in the epithelial channel, where a membrane separates the epithelial channel from the endothelial cells in the vascular channel. IL-13 is added to the endothelial channel at an exemplary 100 ng/ml for an exemplary 7 days.

IL-13 induced goblet cell hyperplasia, see, FIG. 9B, where goblet cells are identified using a marker for Mucin SAC (Mucin 5AC, Oligomeric Mucus/Gel-Forming). This hyperplasia effect can be inhibited by Tofacitinib, an inhibitor of the JAK/STAT pathway (Janus Kinase (JAK) and Signal Transducer and Activator of Transcription (STAT)).

Induced gene expression for adhesion molecules was also observed after IL-13 treatment, FIG. 9C. Examples of IL-13 induced Selectins (P and E) and ICAM-1 (intercellular Adhesion Molecule 1) and VCAM-1 (vascular cell adhesion molecule-1). Doerr, "The condition-dependent proteome." Nat Methods. 13(2):117, 2016. Gene expression in FIG. 9C was correlated with upregulated protein expression observed in fluorescently stained cells shown in FIG. 13B for ICAM1, Vascular cell adhesion molecule 1 (VCAM1) and Vascular endothelial (VE)-cadherin (VE-Cadherin).

FIGS. 9A-B shows an example of one embodiment of an Airway-on-Chip inducing an asthma-like phenotype using IL-13 stimulation. Creation of a Th2 microenvironment through IL-13 stimulation induces an asthma-like phenotype in the Airway Chip. Exacerbation is then triggered by infecting with human rhinovirus 16 (HRV-16). FIG. 9A is a schematic illustration showing IL-13 in the context of an Airway-on-Chip, where IL-13 effects both epithelial cells in the upper channel with an air interface and endothelial cells in the lower channel under flow (left). Another schematic (right) shows additional detail of a mucociliary airway epithelium (ciliated blue cells and pink large goblet cells) in the process of being contacted (infected) with an exemplary respiratory virus at an MOI of 1 (green dots) in the epithelial channel, where a membrane separates the epithelial channel from the endothelial cells in the vascular channel. IL-13 is added to the endothelial channel at an exemplary 100 ng/ml for an exemplary 7 days. FIG. 9B shows effects of IL-13 on epithelial cells: IL-13 induces goblet cells hyperplasia as shown in micrographs of immunostained cells. No treatment, IL-13 treatment, IL-13+Dex (dextran) and IL-13+Tofacitinib. MUCSAC (Mucin 5AC, Oligomeric Mucus/Gel-Forming) (green) and cell nuclei are stained with DAPI (4',6-diamidino-2-phenylindole) as shown in blue.

FIG. 9C shows effects of IL-13 on endothelial cells: a graphical measurement of gene expression over time compared to non-treated cells shows that IL-13 up regulates adhesion proteins such as Selectins (P and E) and ICAM-1 and VCAM-1 graphed as IL-13-induced gene expression changes (Fold over non-treated vs. agent added to chip). Other compounds tested included Interleukin alpha (IL1A), Interleukin beta (IL1B), Interleukin-6 (IL6), Interleukin-8 (IL8), The chemokine (C-C motif) ligand 2 (CCL2), C-C Motif Chemokine Receptor 4 (CCR4), Protein Tyrosine Phosphatase, Receptor Type C (PTPRC), Intercellular Adhesion Molecule 1 (ICAMI), Selectin P (SELP), Selectin E (SELE), Prostaglandin-Endoperoxide Synthase 2 (PTGS2), Transforming Growth Factor Beta 1 (TGFB1), SMAD Family Member 7 (SMAD7), Complement C3 (C3), Angiotensin I Converting Enzyme (ACE), cluster of differentiation 34: CD34 antigen: CD34 molecule (CD34) and Nuclear Factor Of Activated T-Cells 4 (NFATC4).

FIGS. 13A-C shows exemplary inflammatory response in an Airway-on-Chip model of asthma. In one embodiment, an asthma phenotype was generated using IL-13 stimulation. This stimulation led to the activation of human endothelium at 48 hours of treatment. IL-13 induces vessel (endothelial cell) wall priming as part of recruitment of immune cells. FIG. 13A demonstrates log10 significance differences including p values, at horizontal dotted lines, after staining for endothelial cell proteins vs. differences on a Log2 basis between IL-13 induced cells and a control without treatment with IL-13. FIG. 13B shows effects of IL-13 on endothelial cells: as shown in micrographs of immunostained cells: increased adhesion molecule expression was observed. IL-13 100 ng/mL (right panels) vs. no treatment controls (left panels) VE-Cadherin (red), ICAM-1 (green) in the upper panels. VCAM-1 (red) VE-Cadherin (green). Cell nuclei are stained with DAPI (4',6-diamidino-2-phenylindole) as shown in blue. FIG. 13C shows quantitative charts of comparative ICAM-1 (upper chart) and VCAM-1 (lower chart) significant induction vs. controls.

To recapitulate viral-induced asthma exacerbation and model molecular responses observed in severe asthma, IL-13-treated Airway Chip was infected with HRV. HRV challenge of IL-13-treated cultures resulted in altered interferon response and increase of neutrophil recruitment when compared with IL-13 or HRV stimulation alone.

In one exemplary embodiment, IL-13 stimulation generates an Airway-on-Chip model of asthma. Therefore, in one embodiment, a disease state is modeled for an asthmatic phenotype, such as produced by IL-13 stimulation of a respiratory cell layer, that is also infected with a respiratory virus, e.g. a human Rhinovirus. It is not meant to limit IL-13 as a stimulatory agent for inducing an inflammatory phenotype, such as asthma, in a respiratory cell layer. In some embodiments, stimulatory agents such as IL-1 alpha, IL-1beta, IL-3, IL-4, IL-36 (alpha, beta and/or gamma), CXCL8, GM-CSF, and lipid mediators, prostaglandins (e.g. PGE2, PGI2) glucocorticoids, etc., may be used alone or in combination with or without IL-13 for stimulating an inflammatory phenotype.

FIGS. 9A-B shows an example of one embodiment of an Airway-on-Chip inducing an asthma-like phenotype using IL-13 stimulation. Creation of a Th2 microenvironment through IL-13 stimulation induces an asthma-like phenotype in the Airway Chip. Exacerbation is then triggered by infecting with human rhinovirus 16. FIG. 9A is a schematic illustration showing IL-13 in the context of an Airway-on-Chip, where IL-13 effects both epithelial cells in the upper channel with an air interface and endothelial cells in the lower channel under flow (left). Another schematic (right) shows additional detail of a mucociliary airway epithelium (ciliated blue cells and pink large goblet cells) in the process of being contacted (infected) with an exemplary respiratory virus at an MOI of 1 (green dots) in the epithelial channel, where a membrane separates the epithelial channel from the endothelial cells in the vascular channel. IL-13 is added to the endothelial channel at an exemplary 100 ng/ml for an exemplary 7 days. FIG. 9B shows effects of IL-13 on epithelial cells: IL-13 induces goblet cells hyperplasia as shown in micrographs of immunostained cells. No treatment, IL-13 treatment, IL-13+Dex (dextran) and IL-13+Tofacitinib. MUCSAC (Mucin 5AC, Oligomeric Mucus/Gel-Forming) (green) and cell nuclei are stained with DAPI (4',6-diamidino-2-phenylindole) as shown in blue.

Figures 10A, 10B:
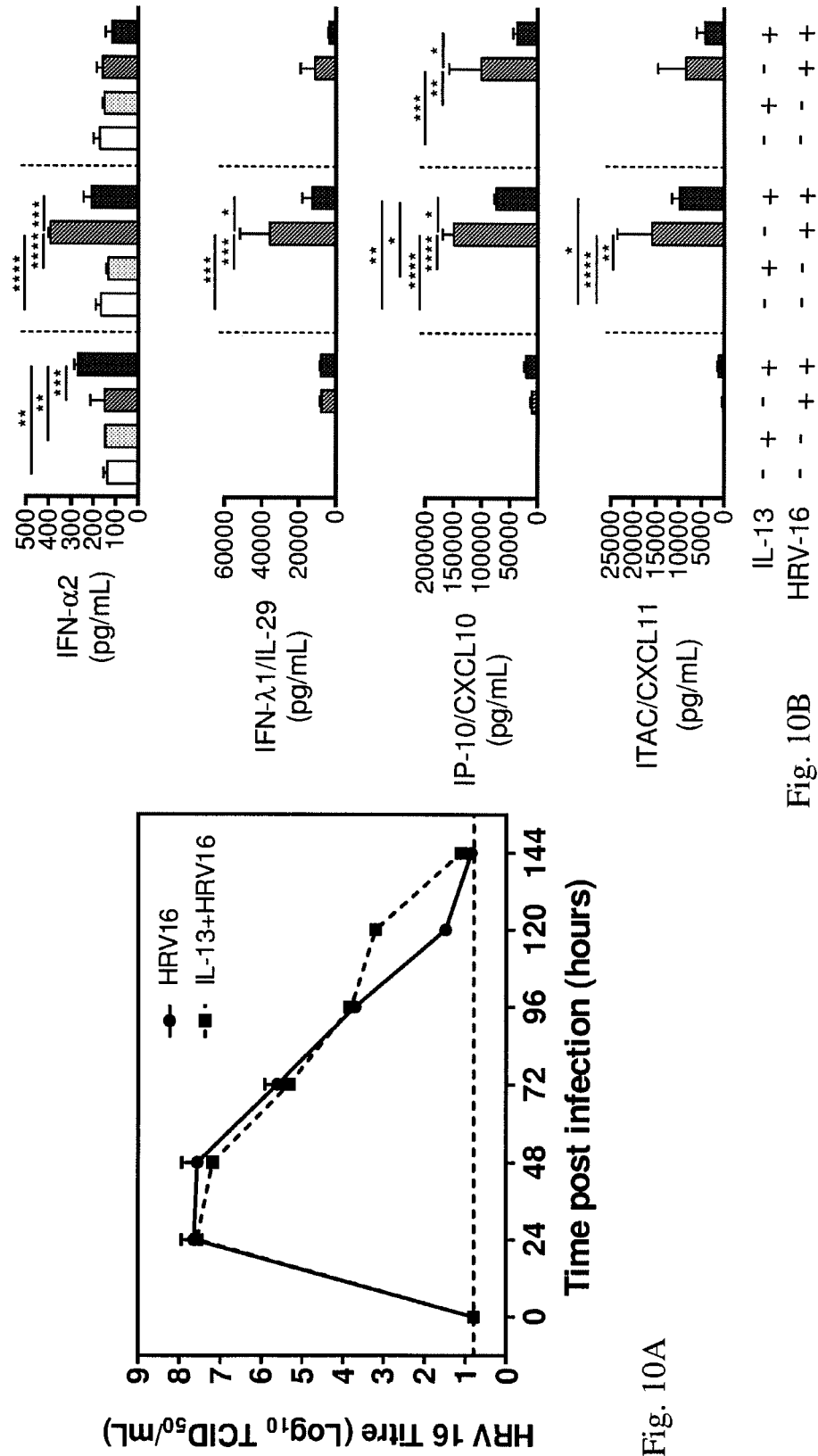
FIGS. 10A-B shows examples of charts comparing cytokine expression after HRV-16 infection in a healthy vs. asthmatic background (in this case implementation by comparing Chips under exemplary variables: with and without IL-13 treatment prior to viral exposure: IL-13 treatment does not alter HRV infectivity but impairs epithelial interferon response.

Additional data shown in FIGS. 10A-B supports the observation that IL-13 treatment does not alter HRV infectivity, FIG. 10A, but impairs epithelial interferon response, FIG. 10B.

FIGS. 10A-B shows examples of charts comparing cytokine expression after HRV-16 infection in a healthy vs. asthmatic background (in this case implementation by comparing Chips under exemplary variables: with and without IL-13 treatment prior to viral exposure: IL-13 treatment does not alter HRV infectivity but impairs epithelial interferon response. FIG. 10A. Shows an exemplary One step growth curves of HRV-16 (MOI=2) in infected Airway chips treated with IL-13 or not. No differences in growth were noted when chips were treated with IL-13. FIG. 10B demonstrates exemplary graphs showing apical interferon response following IL-13 treatment and HRV-16 infection of Airway Chips at 24 h and 48 h post infection. Quantification of interferon response shows that IL-13 treatment alter type I and III interferon and interferon stimulated genes CXCL10 and CXCL11 during HRV-16 infection.

Figures 11A, 11B:
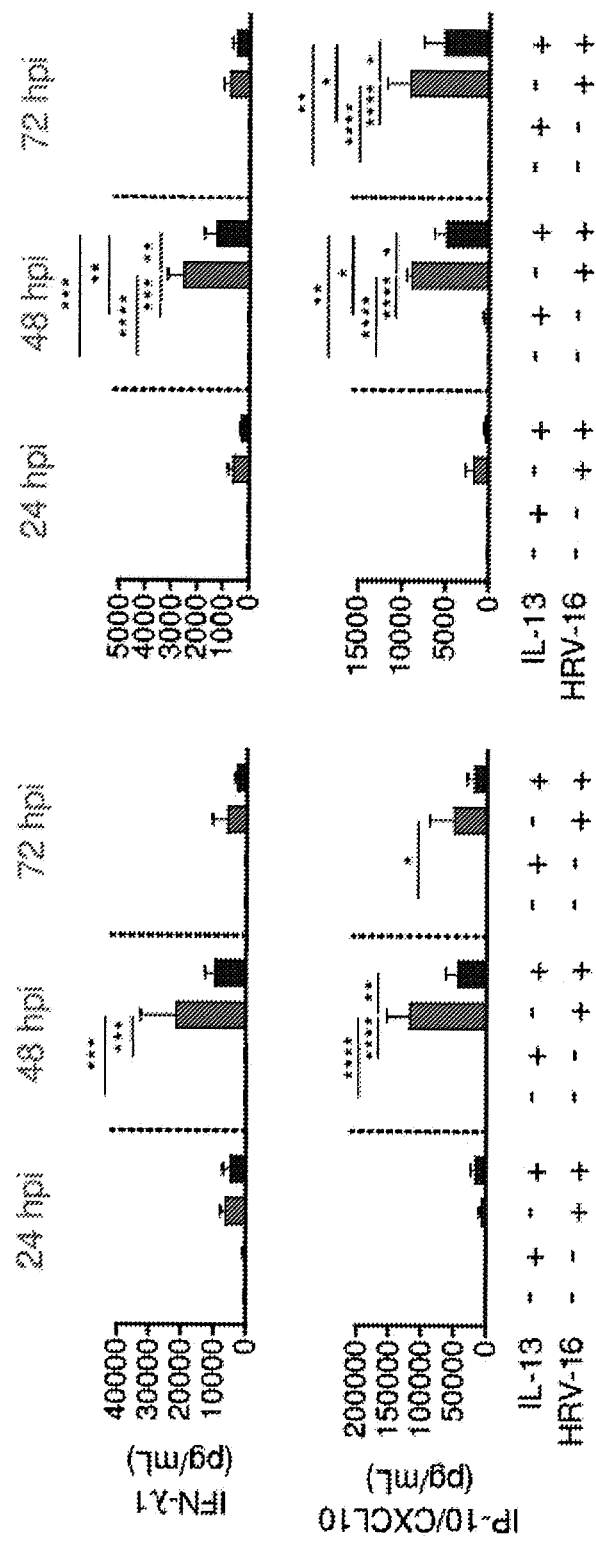
FIGS. 11A-B shows exemplary IL-13 stimulation reduces HRV16-induced interferon response thus an antiviral response is altered by IL-13 treatment of chips. Charts show IFN-λ1 (pg/mL) and IP-10/CXCL10 (pg/mL) measured in apical and basal secretions collected at 24, 48 and 72 h post HRV16 infection comparing control, IL-13 alone, HRV-16 alone and combined treatments. Measurements from release in the upper channel are shown in FIG. 11A apical release and in the lower channel

FIGS. 11A-B shows exemplary IL-13 stimulation reduces HRV16-induced interferon response thus an antiviral response is altered by IL-13 treatment of chips. Charts show IFN-λ1 (pg/mL) and IP-10/CXCL10 (pg/mL) measured in apical and basal secretions collected at 24, 48 and 72 h post HRV16 infection comparing control, IL-13 alone, HRV-16 alone and combined treatments. Measurements from release in the upper channel are shown in FIG. 11 apical release and in the lower channel FIG. 11B shows corresponding basal secretion.

Figures 12A, 12B:
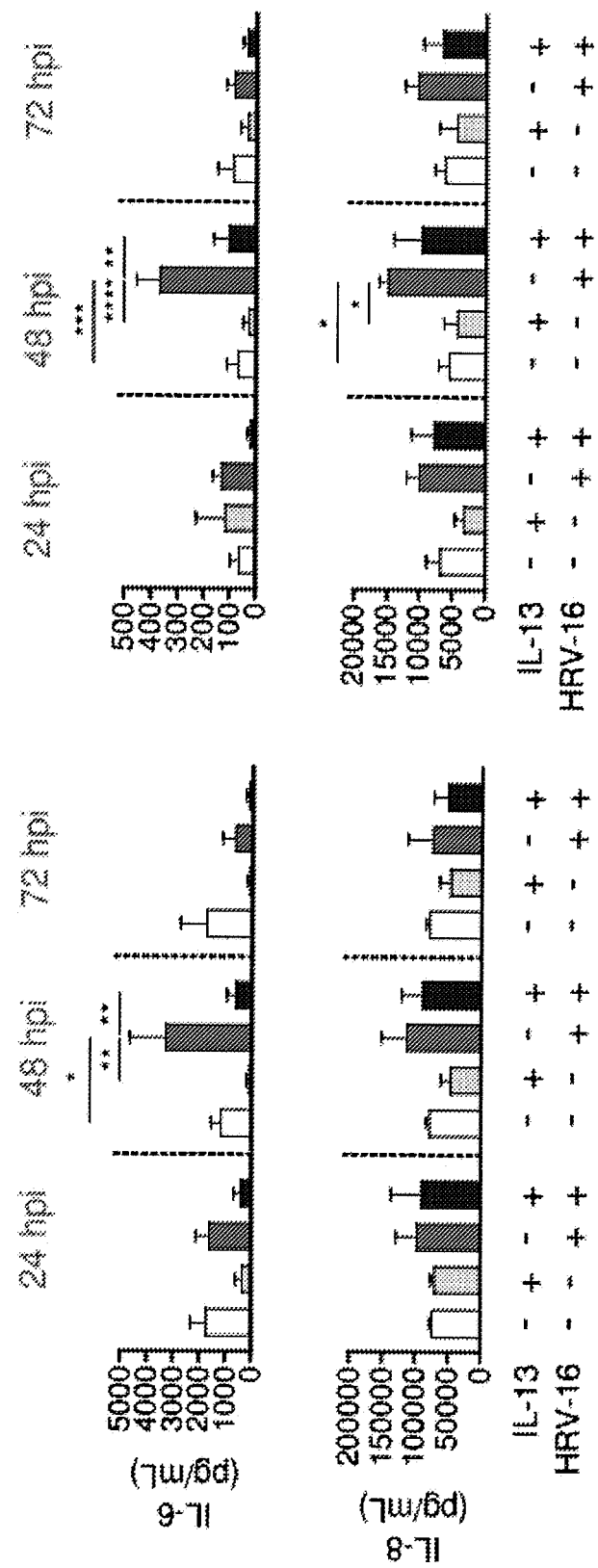
FIGS. 12A-B shows that exemplary HRV16-induced IL-6 secretion is inhibited by prior stimulation with IL-13. Thus, IL-13 may delay or prevent IL-6-driven resolution of HRV-induced inflammation. Charts (i.e. readouts) show IL-6 (pg/mL) and IL-8 (pg/mL) measured in apical and basal secretions collected at 24, 48 and 72 h post HRV16 infection comparing control, IL-13 alone, HRV-16 alone and combined treatments. Measurements from release in the upper channel are shown in FIG. 12A shows apical release and in the lower channel

FIGS. 12A-B shows that exemplary HRV16-induced IL-6 secretion is inhibited by prior stimulation with IL-13. Thus, IL-13 may delay or prevent IL-6-driven resolution of HRV-induced inflammation. Charts (i.e. readouts) show IL-6 (pg/mL) and IL-8 (pg/mL) measured in apical and basal secretions collected at 24, 48 and 72 h post HRV16 infection comparing control, IL-13 alone, HRV-16 alone and combined treatments. Measurements from release in the upper channel are shown in FIG. 12A shows apical release and in the lower channel FIG. 12B shows corresponding basal secretion.

Neutrophil recruitment could be pharmacologically inhibited by MK-7123, a CXCR2 antagonist (10 µM). In fact, as shown herein, a CXCR2 antagonist MK-7123 inhibits neutrophil recruitment, neutrophil migration (crawling) and trans-migration in one embodiment of a severe asthma chip. In fact, as shown herein, MK-7123 reduces neutrophil mobility and limits trans-migration. Thus, in one embodiment, an Airway Chip enables testing of immuno-modulatory compounds of neutrophil recruitment in a model of acute asthma exacerbation.

Thus, a CXCR2 antagonist reduces neutrophil mobility and limits trans-migration.

Therefore, this embodiment of an Airway-on-chip enables the study of neutrophil adhesion, crawling and extravasation by demonstrating the capability to monitor neutrophil crawling and trans-migration of cells out of the endothelial channel.

FIGS. 14A-C shows an example of one embodiment of an Airway-on-Chip emulating acute asthma exacerbation by combining Rhinovirus infection with IL-13 stimulation in the presence of an exemplary immuno-modulatory compound: Neutrophil recruitment following exacerbation with HRV can be reduced by an exemplary CXCR2 antagonist MK-7123. FIG. 14A (upper image) shows one embodiment of an Airway-on-Chip that enables testing of immuno-modulatory compounds, e.g. for neutrophil recruitment, in a model of acute asthma exacerbation. HRV-16 is represented as small green dots in the upper channel while neutrophil cells (also described as polymorphonuclear leukocytes (PMN)) are represented as large purple spots in the lower channel. An enlarged schematic is demonstrated schematically in the lower image showing a HRV-infected Airway Chip during perfusion in the vascular channel of freshly isolated human neutrophil. FIG. 14B shows a series of fluorescent micrographs showing comparisons of stained neutrophil cells (red) recruited to the endothelium and attached to non-treated cells. Treatments included HRV-16 alone infected cells, IL-13 alone treated cells, HRV-16 and (+) IL-13 treated cells, HRV-16+CXCR2in (inhibitor) treated cells, and HRV-16+IL-13+CXCR2in. Non-stimulated chips are showing limited neutrophil recruitment while HRV infected and IL-13-treated chips show increased neutrophil recruitment. IL-13+HRV induce an additive increase in neutrophil recruitment, while treatment with a CXCR2 antagonist. MK-7123 (10 microM) significantly reduced neutrophil recruitment under three stimulation conditions. FIG. 14C is a graphical comparison showing PMN (neutrophil) cells counts as % of untreated cells and cells treated with combinations shown for IL-13, HRV, and CXCR2 (in) treatments. Quantification of neutrophil recruitment (* * $p<0.01$; * * * * $p<0.001$).

Figure 15A:
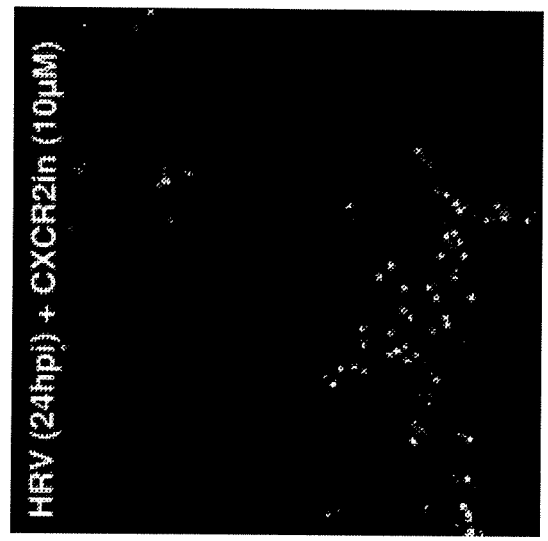
FIGS. 15A-D shows an example of one embodiment of an Airway-on-Chip demonstrating the effect of a CXCR2 antagonist (inhibitor: in) on neutrophil crawling and transmigration of cells out of the endothelial channel.
Figure 15B:
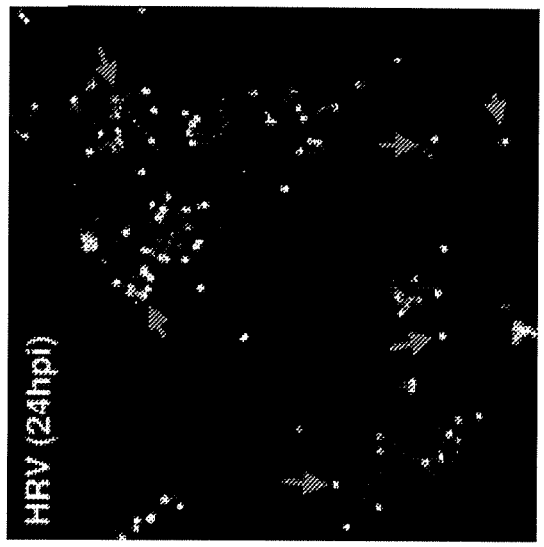
Figure 15C:
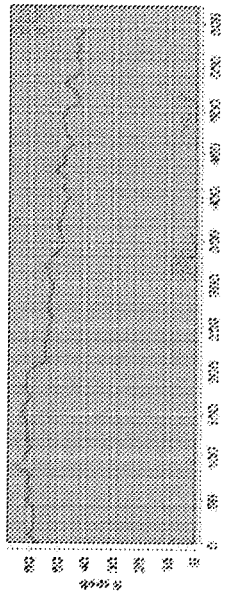
Figure 15D:
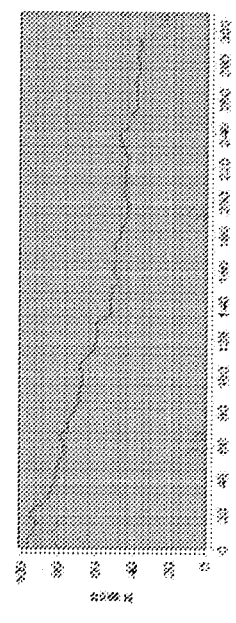

FIGS. 15A-D shows an example of one embodiment of an Airway-on-Chip demonstrating the effect of a CXCR2 antagonist (inhibitor: in) on neutrophil crawling and trans-migration of cells out of the endothelial channel. FIG. 15A is a micrograph showing effects of HRV-16 infected cells (24 hpi) on cell attachment and FIG. 15B shows effects of HRV-16 infected cells (24 hpi) treated with CXCR2in (10 µM) on cell attachment. FIG. 15C shows a graph of the number of spots (i.e. neutrophil cells: N spots) counted over time (up to 300 seconds) for HRV-16 infected cells (24 hpi). FIG. 15D shows a graph of N spots counted over time (up to 600 seconds) for HRV-16 infected cells (24 hpi) treated with CXCR2in (10 µM).

The consequences of a respiratory infection on stimulated epithelium and endothelium contained in the microfluidic chip are then characterized for use with: disease modeling, testing effects of test agents and for drug compound testing, such as CXCR2 inhibitors. Furthermore, human immune cells (e.g. neutrophils) were added inside of the chip to identify the extent of recruitment into the endothelium and epithelium; in addition to observing the pharmacological modulation of interactions between the endothelium and immune cells. For example, neutrophils were used in testing compounds (i.e. pharmacological compounds as immune inhibitors, such as an exemplary CXCR2 inhibitor. In a preferred embodiment, a test compound reduces or prevents the onset of severe asthma symptoms, e.g. reducing or preventing a severe asthma phenotype.

The microfluidic Severe Asthma-on-Chip model is different from previous systems where static transwells cultures were stimulated with IL-13 then infected with Rhinovirus (Am J Respir Cell Mol Biol. 2008 May; 38(5): 517-523; Am J Respir Cell Mol Biol. 2010 December; 43(6):652-61). By contrast, some embodiments of Small Airway-on-Chip described herein have a dynamic component comprising microfluidic movements of media and/or flowing air. Certain embodiments also contemplate the addition of immune cells and behavioral observation of these cells inside the chips; and the use of additional cell types, such as endothelium e.g. as an endothelium microchannel; and cells isolated from patients, such as endothelial cells, epithelial cells, immune cells; etc.

Moreover, the Severe Asthma-on-Chip, is different from the human lung Small Airway-On-A-Chip, described in Benam, et al., "Small airway-on-a-chip enables analysis of human lung inflammation and drug responses in vitro." Published Online 21 Dec. 2015, pages 1-7 and supplemental. Infection with an actual virus was not involved. In contrast, embodiments of microfluidic Severe Asthma-On-Chips described herein comprise infecting cells with respiratory viruses. In other embodiments, microfluidic Severe Asthma-On-Chips comprise immune cells within cell layers in microfluidic Severe Asthma-On-Chips.

As exemplified herein, data demonstrated the physiologically-relevant modeling of the human airway tissue and included demonstration of the capability to infection the Small Airway Lung-Chip with a virus that recapitulates viral-induced exacerbation in asthma. Viral infection in asthma patients can lead to exacerbation of the symptoms and severe asthma. More specifically, the data demonstrated the ability of the Small Airway Lung-Chip to recreate aspects of the pathophysiology of viral-induced asthma exacerbation, including (but not limited to): A) Recreation of airway tissue interfaces of the lung's small airway, with fully differentiated mucociliary bronchiolar airway epithelium underlined by a microvascular endothelium which experiences fluid flow. B) Induction of a pro-inflammatory response characterized by cell deaths, goblet cell hyperplasia, and release of cytokines, was observed when the Small Airway Lung-Chip was infected with human Rhinovirus (HRV), a leading cause of asthma exacerbation in children and adults. C) Accurate modeling of molecular responses was observed in severe asthma, by showing altered interferon response and recruitment of circulating human neutrophils (immune cells). D) Pharmacological modulation of neutrophil recruitment was recreated by demonstrating that neutrophils, that drive innate inflammatory cell infiltration to the lungs in viral-induced asthma exacerbations, can be modulated by a selective CXCR2 antagonist drug agent.

In part, experiments and embodiments described herein, are directed to why asthmatic patients are at risk of developing life-threatening exacerbations following rhinovirus infection while healthy individuals may experience a harmless cold? As discovered by results described herein, risk factors for exacerbations in asthma include but are not limited to having asthma in combination with a respiratory viral infection, e.g. HRV infection, see FIG. 16A for an example. Additional risk factors include but are not limited to having direct viral cytopathic effects, defective or exaggerated antiviral responses, and a dysregulated inflammatory response.

FIGS. 16A-F show exemplary schematics and data, showing viral-induced exacerbation on-chip inducing neutrophil transmigration, for use in on-chip testing of prophylactic treatments for reducing incidents of severe asthma attacks and for treatments during severe asthma attacks to reduce at least one symptom. FIG. 16A shows an exemplary schematic (as a Venn Diagram) where asthma induction as an inflamed airway is represented by IL-13 treatment (left circle) and viral exacerbation of asthma is represented by a rhinovirus (HRV) infection (right circle). The area of overlap represents asthma exacerbation in a patient or on-chip when both conditions are present. FIG. 16B shows an exemplary schematic of one embodiment of asthma exacerbation where a virus is infecting ciliated epithelial cells in the airway channel (green dots and green ciliated cells) which induces neutrophil (bumpy round cells) recruitment (attachment) and movement through the endothelium on the vascular channel, then as shown in FIG. 16C, neutrophils show extravasation through the porous membrane then into the airway side of the membrane, i.e. trans-epithelial migration. FIG. 16D shows one embodiment of a severe asthma chip enabling neutrophil diapedesis: HRV16 (24 hpi) infected cells visualized by immunofluorescent staining of Myeloperoxidase (MPO) stained neutrophils showing a Z-stack confocal microscopic image. FIG. 16E shows a colorized immunofluorescent image of HRV16 (24 hpi) infected cells stained with Myeloperoxidase (MPO) (green)/mAJ2 (red)/DAPI (blue) where MPO+ cells are located near virally infected cells. And FIG. 16F shows a monoclonal antibody (mabJ2) (mouse) detecting double-strand RNA as an RNA replication-center assay for one embodiment of a high content image-based quantification of human rhinovirus and Coxsackie virus infections.

Additionally, as described herein, results identify exemplary points for targeting drugs/therapeutics based in part on the following: Rapid elimination of ciliated cells combined with HRV-induced goblet cells hyperplasia in an already damaged and remodeled asthmatic lung tissue is likely to suppress mucociliary transport in infected area of the respiratory tract, leading to defective clearing of cell debris, viral particles and excessive mucus, thus worsening the burden of the disease.; An impaired IFN response following HRV infection of asthmatic lungs may also contribute to the disease burden by decreasing viral clearance and extend the duration of infection. IL-13-induced priming of microvascular endothelial cells may amplify infiltration of inflammatory cells to the site of infection; and reduced IL-6 secretion might delay resolution of the immune response in airways, e.g. allergic airways, leading to a prolonged neutrophilic episode and ultimately increasing tissue damage.

As one example, relatively high levels of IL-6 secretion in response to a respiratory virus infection, i.e. HRV16, in a microfluidic device without an asthma phenotype was significantly reduced in both the apical and basal regions in combination with an asthma phenotype, i.e. IL-13 stimulation, and a respiratory virus infection, i.e. HRV16 in a severe asthma microfluidic device. This observation (i.e. readout) shows that an IL-6 response to viral infection is diminished in combination with an asthma phenotype, therefore may represent a sub-type of asthma (e.g. in asthma patients and/or during an asthmatic episode) where IL-6 may be diminished. In other words, a reduction in IL-6 secretion in an asthmatic phenotype in vivo, that also becomes infected with a respiratory virus, may result in a severe asthma attack. Thus, at least one sub-type of asthma in vivo having an IL-13 associated inflammatory respiratory epithelium, (i.e. modeled by IL-13 treatment of respiratory cells in vitro) may benefit from administration of a drug, e.g. IL-6 as described herein, for reducing asthmatic symptoms for reducing symptoms of asthma, i.e. in the absence of severe asthma, and/or as a prophylactic for reducing the incidence of severe-asthma in asthma patients and/or reducing the symptoms of severe asthma. Support for the use of IL-6 in asthmatic patients is provided in part in, FIG. 12. It is not meant to limit a potential therapeutic to IL-6, thus IL-10 may also be a potential therapeutic, see FIG. 11.

Therefore, as one example of a potential therapeutic identified herein, IL-6, IL-6 derivatives, IL-6 analogues, IL-6 mimics, or IL-6 agonists may be employed. Such a therapeutic may be administered to a human subject with a respiratory disease, such as asthma. Such a therapeutic may be administered to a human subject with a respiratory disease that has been exacerbated by an agent, such as asthma exacerbated by a pathogen (e.g. viral or bacterial) or to a subject where the asthma is not exacerbated. In one embodiment, such a therapeutic is administered by injection or by mouth. In one embodiment, such a therapeutic may be administered as an aerosol directly to the lung. In some embodiments, such a therapeutic reduces damage to the lung. Thus, in one embodiment, the present invention provides an improved means of treating respiratory disease (such as asthma) in a human subject (including but not limited to the nosocomial patient), preferably with aerosolized therapeutic as discussed above (i.e. IL-6, IL-6 derivatives, IL-6 analogues, IL-6 mimics, or IL-6 agonists) in sufficient amounts for therapeutic effect. In one aspect, the invention assures this result when aerosol is delivered.

A variety of patient types and delivery devices are contemplated. In one embodiment, the therapeutic (i.e. IL-6, IL-6 derivatives, IL-6 analogues, IL-6 mimics, or IL-6 agonists and agents that induce the release or production of IL-6) is administered directly to the mucosal surface of the lungs of spontaneously breathing patients in aerosols (liquid droplets or dry powders) delivered via various nebulizers. In another embodiment, such an aerosol is delivered to the intubated patient by introduction into the ventilator circuit (e.g. aerosol is delivered directly to the airways distal of the ventilator circuit). In one embodiment, it is delivered directly to the airways of the animal subject or human patient, largely by-passing the ventilator circuit. In one embodiment, particular with respect to "constant-flow" ventilators, the present invention contemplates limiting the delivery event strictly to the inspiratory phase of the ventilator cycle and, if possible, at a reduced flow-rate. Thus, in one embodiment, said aerosolizing of step (c) is actuated on (or in fixed relation to) the inspiration phase of the breathing cycle. In one embodiment, a mechanical ventilator controls a breathing cycle for the patient, said cycle comprising an inspiration phase of the breathing cycle.

Moreover, while some embodiments of the present invention are presented in the context of the intubated patient, other patients at risk for infection are contemplated (i.e. non-intubated patients) as treatable with the methods and devices of the present invention. For example, the elderly (particularly those in nursing homes), horses, dogs and cats in competitions (show and racing animals), animals that frequently travel (e.g. circus animals), animals in close quarters (e.g. zoos or farms), humans and animals in general are at risk for lung infections. The present invention contemplates delivery of aerosols to the trachea and/or deep lung for such individuals—both prophylactically (i.e. before symptoms) and under acute conditions (i.e. after symptoms)—wherein said aerosols comprise IL-6, IL-6 derivatives, IL-6 analogues, IL-6 mimics, or IL-6 agonists.

By using an aerosol formulation of the therapeutic, it is contemplated that the treatment means concentrates the therapeutic agent specifically at affected sites in the lung such that therapeutic levels of administrated drug are achieved without significant systemic exposure of the patient to the drug. In one embodiment, the invention further contemplates a dose control device to govern this specialized regimen. In one embodiment, the present invention contemplates an aerosol comprising the therapeutic (IL-6, IL-6 derivatives, IL-6 analogues, IL-6 mimics, or IL-6 agonists).

In one embodiment, the present invention contemplates a drug-loaded nebulizer comprising the therapeutic (IL-6, IL-6 derivatives, IL-6 analogues, IL-6 mimics, or IL-6 agonists) in solution (i.e. to be aerosolized). In another embodiment, the present invention contemplates a device comprising a fluid driving element attached to a dose metering element, said dose metering element engaged to an aerosolizing catheter. In a preferred embodiment, the dose metering element is detachably engaged to said aerosolizing catheter and comprises a reservoir of defined volume, said reservoir being preferably configured as a transparent or semi-transparent cylinder or tube, with or without visible measurement indicia. In this preferred embodiment, the therapeutic formulation (i.e. IL-6, IL-6 derivatives, IL-6 analogues, IL-6 mimics, or IL-6 agonists) for the patient is placed in the reservoir, the fluid driving element being disposed in relation to the reservoir such that, in operation, the fluid driving element urges the fluid formulation out of the reservoir and into the aerosolization device. In a preferred embodiment, the fluid driving element comprises a plunger or piston driven by compressed gas, said compressed gas stored in a container or canister and released by the operator of the device. When the release of compressed gas is triggered, the plunger or piston pushes the defined volume of the therapeutic formulation into the aerosolizing catheter. In a particularly preferred embodiment, the device is a "stand alone" device configured such that it can engage an opening or port in a ventilation system, wherein said aerosolizing catheter is dimensioned to fit inside (or along side) an endotracheal tube (and/or tracheostomy tube) of an intubated patient, such that the delivery end (i.e. out of which the aerosol is delivered) of the catheter extends approximately to the end of the tube (or preferably below the end of the tube, thereby delivering aerosol in a manner that bypasses the tube). In a particularly preferred embodiment, the end of the aerosolizing catheter comprises a baffle to slow the speed of the aerosol.

In some embodiments, a drug treatment to lung tissue in a patient includes but is not limited to a spray, aerosol, gel, solution, emulsion, or suspension. In some embodiments, a formulation of a drug is used for drug treatment, wherein in some embodiments, a formulation of a drug may range from a 1 picogram per ml to 100 ng per ml to 1 mg per 100 ml or more. In some embodiments, a formulation of a drug is ingestible by mouth. In some embodiments, a formulation of a drug in a liquid for aerosol administration may range from a 1 picogram per ml to 100 ng per ml or more. In some embodiments, a drug is administered by a metered-dose inhaler, by controlled inhalation flow rates, as a predetermined dose of aerosolized drug, administered as one or more pulses. In some embodiments, a puff from an inhaler results in about 7-40 percent of the drug reaching the lungs. In some embodiments, a puff from an inhaler results in about 40 percent or more up to 100% of the drug reaching the lungs under efficient conditions of patient use of an inhaler.

In some embodiments, said where said drug is administered as an aerosol, said drug has a concentration of 1 picogram per ml up to 100 ng per ml or more. In some embodiments, a formulation of a cytokine ranges from 1 picogram/ml to 100 ng per ml or more. In some embodiments, a formulation of an IL-6 cytokine ranges from 1 picogram per ml to 100 ng per ml or more.

In some embodiments, the amount of a drug administered to a patient is measured. Thus in some embodiments, the amount of drug delivery to the lung is measured in a bronchial lavage (BAL).

In some embodiments, the amount of a drug in an aerosol is measured. In some embodiments, an amount of drug administered to a patient's lungs that is not absorbed is measured.

Thus, in some embodiments, an aerosol-to-liquid sampler is used for measurement of cytokine levels from an aerosol device or in exhaled air from a patient, starting in the sub-picogram/mL concentration range using a multiplex immunoassay, e.g. high sensitivity human cytokine LINCOplex Kits (Millipore, Billerica, Mass.). In one embodiment, airborne concentrations of cytokines are reported in $pg/m^3$ air. Other reported results are presented in total mass (pg) of cytokine measured or collected by the sampling device.

In another embodiment, the present invention contemplates a method, comprising a) providing i) a patient exhibiting one or more symptoms of asthma, and ii) a nebulizer comprising a formulation of a therapeutic (i.e. IL-6, IL-6 derivatives, IL-6 analogues, IL-6 mimics, or IL-6 agonists); and b) administering said formulation as an aerosol to said patient via said nebulizer. In one embodiment, said patient exhibits one or more symptoms of exacerbated asthma. In one embodiment, said patient also exhibits one or more symptoms of an infection (e.g. viral or bacterial). In one embodiment, said patient is elderly (e.g. 60 or more years of age, and more preferably 70 or more years of age). In one embodiment, said patient is intubated with a tube selected from endotracheal tubes and tracheostomy tubes. In one embodiment, said tube is connected to a ventilator circuit comprising an inspiratory line and an expiratory line converging at a junction, wherein the nebulizer is positioned in proximity to said junction and in fluid communication with said tube, wherein said nebulizer is not positioned in said inspiratory line or said expiratory line.

Further, a Small Airway Lung-Chip is contemplated for use in high through put cytokine treatment and evaluation, and even further for high through put testing of drug treatments for severe respiratory infections, such as asthma, COPD and CF. It is not intended that the present invention be limited to how a particular phenotype is generated. In one embodiment, a COPD phenotype is generated by exposure of respiratory cells to smoke (e.g. tobacco smoke) on a Small Airway Lung-Chips, including but not limited to burning various types of tobacco as a means of aerosol (or vaporized) delivery.

I. Asthma, Airways And Respiratory Viruses.

Embodiments of microfluidic Airway-on-chips described herein include combining a microfluidic Airway-on-Chip as a 3D physiological system with respiratory viruses for simulating airway responses when cells have underlying viral infections as a microfluidic Severe Asthma-on-Chip. During the development of the present inventions, a microfluidic Small Airway-on-Chip with an underlying viral infection, e.g. a HRV infection, showed characteristics of an airway undergoing a severe asthmatic condition when triggered with an asthma related cytokine, e.g. IL-13. Thus, in preferred embodiments, a microfluidic Severe Asthma-on-Chip comprising a respiratory virus provides a model for pre-asthmatic attack inflammatory conditions. A microfluidic Severe Asthma-on-Chip is contemplated for use in modeling the effects of asthma triggers on infected airway linings. For reference, information is provided below on asthma, airway anatomy in general in relation to asthma and respiratory viruses.

A. Asthma.

Asthma refers to a chronic and often a lifelong respiratory disease, ranging from mildly irritating to a serious, even life-threatening condition, termed severe asthma or 'Status Asthmaticus'. In other words, asthma symptoms vary in frequency and severity. When a person is affected with asthma, in general it becomes more difficult to move air in and out of the lungs. Asthma can start at any age but it most commonly starts in childhood. At least 1 in 10 children and 1 in 20 adults have asthma.

Although asthma makes breathing difficult for millions, including children, there is no cure. In fact, nearly 26 million Americans have asthma, including more than 7 million children. In America, it causes millions of lost school and workdays every year and is the third leading cause of hospitalization among children.

The airways' epithelial lining in an asthma patient tends to be in a hypersensitive state often characterized by redness and swelling (inflammation), that may be referred to as 'asthmatic airways'. This hypersensitive state makes the airways react to an asthma "trigger(s)" such that these asthmatic airways are extra sensitive to certain compounds in the environment, such as dust, chemicals, smoke, pet dander, etc., and/or sensitive to mere exposure to an environmental condition such as cold air, misty air, evening air or time period, etc., alone, or in combination with an increased breathing rate, such as caused by stress or exercise.

When a person breathes in a trigger, the inside linings of the airways (epithelial lining) swell such that asthma usually causes episodes of breathlessness that may be accompanied by chest tightness and/or wheezing. A trigger may also induce bronchial spasms where the muscles that wrap around your airways tighten, making breathing even harder. Spasms of the bronchial tube narrow the space for the air to move in and out of the lungs. When this happens, it's referred to as an asthma flare-up, asthma episode or asthma "attack." Common symptoms are coughing, wheezing, breathless, and may develop a feeling of chest tightness. Symptoms can range from mild to severe between different people, and at different times in the same person. Each episode of symptoms may last just an hour or so, or persist for days or weeks unless treated.

Asthma attacks often do not stop on their own without asthma treatment. When early warning signs of an asthma attack are ignored, this increases the risk of developing Status Asthmaticus, which may require immediate medical attention and treatment, including hospitalization.

The severity of the asthma attack may depend on how well the underlying asthmatic airways are controlled, i.e. reflecting how well the airway inflammation is being controlled. Inhaled steroids (e.g. albuterol) are potent anti-inflammatory drugs that are highly effective in reducing inflammation associated with asthma. However, some asthma attacks do not respond to immediate care (quick-relief medications), e.g. a bronchodilator inhaler rendering an acute asthma attack potentially life-threatening. When an acute asthma attack is unresponsive to treatment with an asthma inhaler (e.g. albuterol), this may be a symptom of a severe asthma attack.

Symptoms of a severe asthma attack may also include: persistent shortness of breath; the inability to speak in full sentences; breathlessness even while lying down; chest that feels closed; bluish tint to lips; agitation, confusion, or an inability to concentrate; hunched shoulders and strained abdominal and neck muscles; and a need to sit or stand up to breathe more easily. These symptoms may also be signs of an impending respiratory system failure from a lack of oxygen due to obstructed airways, which requires immediate medical attention. Ensuing respiratory failure results in hypoxia, carbon dioxide retention and acidosis.

Other physical asthma related symptoms might be noticed as inflammation within the mouth, pharynx, and upper airway, along with increased mucus production and narrowed airway openings. Asthmatic conditions include smaller airways, including bronchioles, in addition to the larger bronchial tubes. For reference, an overview of the "airway" or "respiratory" tract is provided below.

B. Ainvay (Respiratory) Tract.

In part, the descriptions of airway tissues is provided for identifying cell types contemplated for use in microfluidic chips as described herein for providing a Severe Asthma-On-Chip. Thus, the present invention contemplates embodiments where one or more of the cell types from the respiratory tract (described below) are placed within a microfluidic device and exposed to flow conditions. These cells can then be exposed to a stimulating agent (e.g. IL-13) and/or infected with a respiratory virus (e.g. HRV).

A human respiratory tract or "airway" refers to a pathway that carries air from the outside of the body to the lungs and then back out. For reference, it can be divided into upper (conducting) and lower (conducting and respiratory) parts. The upper respiratory tract includes the nose, sinuses, throat (pharynx) and voice box (larynx). After passing through this upper conducting region, inhaled air passes through the lower respiratory tract, including the portion of the larynx below the vocal cords, single trachea, then highly branched conducting airways of bronchi and bronchioles. More specifically, the single trachea divides into a right main bronchus and left main bronchus (bronchus: singular). As the air travels to the lung tissue, from larger to smaller airways, it moves through the trachea into primary bronchi (bronchi: plural), secondary bronchi (lobar bronchi), tertiary bronchia (segmental bronchia) then bronchioles. Intrasegmental bronchi refer to bronchial branches within the lung tissue contiguous with bronchioles. The bronchioles terminate into small collections of air sacs known as alveoli, which is where the actual exchange of CO2 and Oxygen occur. Thus bronchioles include terminal bronchioles, each which support an airway into a lobule of air sacs, and respiratory bronchioles with attached alveolar sacs. Each respiratory bronchiole supplies an airway into each air sac (acinus or respiratory unit). Thus, respiratory parts of the airway include respiratory bronchioles contiguous with an alveolar air duct, allowing air to move from the respiratory bronchioles into and out of the alveolar sac.

In other words, as "airways" of the lungs, inhaled air passes through the nose or mouth into the larynx, then into the trachea through bronchi into bronchioles then into the alveoli (air sacs) of the lungs where an alveolar-capillary interface allows CO2 and O2 air-red blood cell exchange.

Primary bronchi are located in the upper portion of the lungs, with secondary bronchi near the center of the lungs. Tertiary bronchi are located just above the bronchioles. Structurally, the intrapulmonary (secondary) bronchi have a lining of pseudostratified ciliated columnar epithelium, a basement membrane with a lamina propria containing an abundant longitudinal networks of elastic fibers made by resident stromal cells.

Stomal cells in the respiratory airway linings, i.e. connective tissue cells, are cells secreting connective tissue compounds, include but are not limited to fibroblast cells, pericyte cells, etc. Stromal cells particularly in the respiratory tract contribute elastic connective tissue. Additionally there are spirally arranged bundles of smooth muscle, abundant mucoserous glands, and, in the outer part of the wall (adjacent to bodily tissues), and irregular plates of supportive hyaline cartilage.

In bronchi, the C-shaped cartilage of the trachea is replaced by separate plates of cartilage. At the same time, the lamina propria becomes surrounded by a band of smooth muscle fibers that are arranged spirally and criss-cross one another. The smooth muscle can be considered as a separate layer, the muscularis, lying between the mucosa on the one side and the submucosa, fibrocartilage plates and adventitia on the other side.

The mucosa of bronchi, as in the trachea, has epithelium (e.g. ciliated pseudostratified columnar with goblet cells, a basement membrane, and a lamina propria. Goblet cells in bronchi and bronchiole are less numerous than in the trachea. They are usually filled with mucous secretory droplets, which are discharged into the lumen where they form a mucous blanket on top (apical) surface of the epithelial cells. Goblet cell mucus is contemplated to effect ciliary action of the epithelial cells. For example, in the absence of mucus, cilia fail to continue a beat-like motion. This movement is restored by the addition of mucus in experimental systems.

Serous and mucous glands are present in the submucosa of bronchi, with decreasing numbers per area with each division of the branches into smaller order bronchi. The adventitia or peribronchial layer contains many elastic fibers and separates the wall of the bronchus from pulmonary parenchyma. It permits bronchi to move independent of other lung parenchyma.

In contrast to bronchi, bronchioli lack cartilage and glands and generally have a diameter less than 1 mm. Three layers can be distinguished: mucosa, muscularis, and an outer layer. Due to the absence of cartilage and contraction of smooth muscle the mucosa is highly folded. It is lined with a simple cuboidal epithelium, which besides ciliated and mucous-secreting cells includes Clara cells.

The muscularis is the thickest layer. It has thick bands of smooth muscle, which completely encircle the bronchiole. The connective tissue of the thin outer layer is continuous with the parenchyma of the lung so that these bronchiole passages move with the lungs.

When the bronchi become swollen due to irritants or infection, bronchitis may result making breathing more difficult. Bronchitis sufferers also tend to have much more mucus and phlegm than someone without inflamed bronchi. Asthma is a condition that typically affects the smaller airways, e.g. bronchioles. This area of the airway may narrow (i.e. constrict) due to a bronchospasm.

C. Cystic Fibrosis (CF).

In one embodiment, the present invention contemplates a model of Cystic fibrosis (CF) comprising a microfluidic device with respiratory cells from or derived from a CF patient, or respiratory cells that have been modified to mimic the respiratory cells of a CF patient. In some embodiments, the present invention contemplates methods where such respiratory cells are exposed to infectious agents, such as bacteria (e.g. *Pseudomonas aeruginosa*).

CF refers to an inherited disorder that may cause severe damage to the lungs, digestive system (including intestine) and other organs in the body. In people with cystic fibrosis, secretions from goblet cells, or equivalents, are increased in amount and become sticky and thick instead of the more healthy slippery and thin secretions. Secretions in CF patients may plug up drainage tubes, airway ducts and passageways, especially in the lungs, instead of acting as thin and slippery lubricants for moving microbes away from cells and out of the body. Furthermore, sticky and thick mucus in the lungs traps microbes and provides nutrients for their replication and growth unlike healthy and thin mucus. Thus examples of commonly associated complication in CF patients are extreme breathing difficulties, which may lead to susceptibility for chronic respiratory infections, as well as defective signaling in the intestine.

At least one genetic change (i.e. mutation) between the cftr (chloride channel CFTR (cystic fibrosis transmembrane conductance regulator)) gene of nonCF patients vs. CF patients is associated with differences in controlling movement of salt and water in and out of cells. In CF patients, the protein of this gene does not function as well as in healthy patients, in part, causing the thick and sticky mucus, along with increased salt in sweat. A patient may be a CF carrier, having one allele with a cftr mutation, or display active CF with both alleles having a cftr mutation.

Bacterial infections (e.g. *Pseudomonas aeruginosa*) on the disease (CF) background are found clinically. In fact, a chronic infection with *P. aeruginosa* is one of the main proven perpetrators of lung function decline and ultimate mortality in CF patients. Commonly found soil, water and plants, *P. aeruginosa* is considered an opportunist pathogen in that although it may infect healthy people, it rarely causes disease. However, more severe infections may occur in people who already have another illness. Once easily treated by several types of antibiotics, multiple-drug resistant strains known as Multidrug Resistant *Pseudomonas aeruginosa* (MDR-Pa) are becoming increasingly prevalent and much more difficult to treat. In the human body, *P. aeruginosa* forms large colonies over the surface of cells, known as biofilms, which help it avoid consumption (e.g., phagocytosis) by neutrophils in addition to other properties. A biofilm in general refers to a structured consortium of bacteria, embedded in a self-produced polymer matrix consisting of polysaccharide, protein and DNA.

Bacterial biofilms, in part, cause chronic infections because they show increased tolerance to antibiotics and resist phagocytosis, as well as other components of the innate and the adaptive immune system. As a consequence, a pronounced antibody response may develop, leading to immune complex-mediated chronic inflammation, dominated by polymorphonuclear leukocytes (e.g. neutrophils).

Chronic inflammation is a cause of the lung tissue damage in CF. Another contribution to persistence of chronic *Pseudomonas aeruginosa* lung infections in cystic fibrosis (CF) patients is due to biofilm-growing mucoid (alginate-producing) strains. One form of *P. aeruginosa* produces large amounts of a sugar (alginate) matrix and adheres to the damaged epithelial cell surfaces making the organism virtually impossible to eradicate. This type of *P. aeruginosa* is described as "mucoid". In CF lungs, for example, the polysaccharide alginate is the major part of the *P. aeruginosa* biofilm matrix.

Biofilm growth in CF lungs is associated with an increased frequency of mutations, slow growth and adaptation of the bacteria to the conditions in the lungs, and resistant to antibiotic therapy. Low bacterial metabolic activity and increase of doubling times of the bacterial cells in CF lungs are responsible for some of the tolerance to antibiotics. Conversely, conventional resistance mechanisms, such as chromosomal β-lactamase, upregulated efflux pumps, and mutations of antibiotic target molecules in the bacteria, also contribute to the survival of *P. aeruginosa* biofilms.

Biofilms can be prevented by early aggressive antibiotic prophylaxis or therapy, and they can be treated by chronic suppressive therapy. Hoiby, et al., Future Microbiol. 5(11): 1663-74, 2010.

*P. aeruginosa* is also particularly resistant to antimicrobial intervention because it has a large and diverse set of multidrug efflux pumps and an especially impermeable outer membrane (OM), and it can metabolize some antimicrobial compounds. In addition, *P. aeruginosa* is known to form biofilms that can further protect the bacteria. These biofilms are the subject of a significant body of research, and some investigators have proposed that clinical treatment of *P. aeruginosa* should involve elements that break down or prevent the formation of these biofilms (including but not limited to biofilm-like structures and microcolonies).

Another associated infection in CF patient is caused by *Staphylococcus aureus* bacteria, which causes pneumonia and skin infections. It is commonly found in the nose and on the surface of skin. Once easily treated by antibiotics, a methicillin-resistant strain known as MRSA is becoming more common.

Additional bacteria associated with CF respiratory infections include but are not limited to *Burkholderia* spp (*B. multivorans* and *B. cinocepacia*, etc.). This is a particularly aggressive bacterium that can cause a rapid decline in lung function and is often difficult to treat, as it may be resistant to most antibiotics.

Fungi may also contribute to lung impairment in CF patients such as *Aspergillus fumigatus*, a fungus or mold that is common in the environment. It may or may not cause symptoms if it is present in the lungs. However, some patients develop an allergy to the *Aspergillus fumigatus*. This allergy is called allergic bronchopulmonary aspergillosis or ABPA. Treatment of this organism depends on the symptoms.

The body mounts a strong immune response to fight bacteria and other organisms in individuals with CF. However this constant, aggressive response to chronic infection may also lead to lung damage. In healthy lungs, white blood cells, or neutrophils, attack and eradicate bacteria. In CF patients, the neutrophils may function normally, but bacteria may not be eradicated. Further, when neutrophils engulf bacteria, they release chemicals that cause damage to the lungs. Even though the body can normally neutralize these chemicals, the ongoing presence of neutrophils in the airway overwhelms this process. Eventually, lung tissue is destroyed, airway gland secretion is increased, and cilia function decreases.

Bronchiectasis is one of the results of chronic inflammation, infection and mucus obstruction in CF lungs, where the muscular and elastic components of the airways are destroyed. This makes the airways weak and makes them dilated. The airways may balloon out to form a perfect hiding place for infection and pus. Tissue around the airways may also be damaged and scarred, blocking secretions from escaping the bronchial tree.

Medically related complications from producing thick and sticky mucus in the respiratory tract include but are not limited to: increased susceptibility to pneumonia, an increased susceptibility to sinus infections, an increased susceptibility to bronchial infections, an increased susceptibility to lung infections, induced adverse respiratory symptoms, etc., any one of which may lead to coughing, nasal congestion, etc. Additional complications may include induction of nasal polyps, increased sinus and nasal infections. Complications of altered secretions in other areas of the body include but are not limited to inflammation of the pancreas, and digestive tract disorders.

Thus, in some embodiments, a CF chip is contemplated. As one example, in some embodiments, cells may be derived from cystic fibrosis patients for seeding onto microfluidic chips. Such cells include but not limited to primary cells (e.g. cells derived from patient biopsy or lavage), cells derived from organoids grown from patient cells, cell-lines derived from CF patients, and cells derived from patient iPS cells lines that are differentiated into suitable epithelial cells. Any of the aforementioned cells used in embodiments of the CF chip may include epithelial cells lung (e.g. airway epithelial cells), intestinal epithelial cells, or endothelial cells. In some embodiments, cells seeded onto the CF chip comprise cells modified to include CF-related genes or phenotypes. For example, cells from any of the aforementioned cell sources (e.g. primary cells, organoid-derived cells, cell-lines, and iPS-derived cells) can be modified using methods known in the art, including but not limited to transfection (including viral transfection), and zinc-finger nucleases. It is not meant to limit the types of CF cells used in a CF chip. In fact, any of the cells, including immune cells, described herein for this and for use in other microfluidic chips described herein, may find use in a CF chip of the present inventions.

As one example, cells from CF patients may be isolated and used as described herein. In one embodiment, cells from CF patients are immortalized, see for examples of the methods: Ehrhardt, et al., "Towards an in Vitro Model of Cystic Fibrosis Small Airway Epithelium: Characterisation of the Human Bronchial Epithelial Cell Line Cfbe41o." *Cell Tissue Res*, 323(3):405-415 (2006). Such modeling of CF conditions using cells from CF patients is not limited to actual patients, but may include carriers of CF for modeling effects of cells having one allele having a CF gene mutation as compared to mutations in both alleles, in relation to respiratory infections and asthma.

In some embodiments, CF microfluidic chips are contemplated for use in CF drug development (including assessment of compound efficacy), high-throughput drug screening, and the selection of therapies for individual patients (e.g. personalized medicine).

D. Chronic Obstructive Pulmonary Disease (COPD).

In one embodiment, the present invention contemplates a model of Chronic Obstructive Pulmonary Disease (COPD) and related emphysema comprising a microfluidic device with respiratory cells from a COPD patient or respiratory cells that have been modified to mimic the respiratory cells of a COPD patient. In some embodiments, the present invention contemplates methods where such respiratory cells are exposed to infectious agents, such as bacteria, fungi and viruses. COPD is considered the fifth leading cause of death worldwide (Pauwels & Rabe, 2004) and it will become, as predicted by the World Health Organization (WHO), the third leading cause of death worldwide by 2030 (www.who.int/respiratory/copd/en/index.html). Even though airborne pollutants such as smoke from the burning fuel or coals can cause COPD, the main inducing factor is exposure to cigarette smoke.

COPD is a complex syndrome comprised of airway inflammation, mucociliary dysfunction and consequent airway structural destruction. This process is considered non-reversible. Upon the irritant challenge, the airway epithelial cells synthesize and release pro-inflammatory cytokines and chemokines such as IL-8, MIP-3alpha, which in turn recruit neutrophils, CD8+T-lymphocytes, B-Cells, macrophages and dendritic cells to the lumen of the airways. The matrix-metalloproteinases (MMP-6, MMP-9), among other mediators, cause airway injury and remodeling, eventually leading to airway obstruction.

Thus, in some embodiments, a COPD chip is contemplated. In some embodiments, cells may be derived from COPD patients for seeding onto microfluidic chips, including but not limited to primary cells and cells derived from patient cells, such as iPS cell lines and organoid derived cells, that are differentiated into airway cells. It is not meant to limit the types of COPD cells used in a COPD chip. In fact, any of the cells, including airway cells and immune cells, as described herein for this, and for use in other microfluidic chips described herein, may find use in a COPD chip of the present inventions.

As one example, cells from COPD patients may be isolated and used as described herein. In one embodiment, cells from COPD patients are immortalized, see for examples of the methods, such as described herein for CF cells. Such modeling of COPD conditions using cells from COPD patients is not limited to actual patients, but may include relatives of COPD patients, and normal healthy people, for modeling effects of cells chronically exposed to tobacco products. In some embodiments, these effects are in relation to respiratory infections and asthma.

E. Respiratory Viruses.

Pathogenic viruses in some patients, and nuisance viruses in others, induce inflammation of the nasal and/or bronchial system. While in some patients the infection is self-limited with few additional symptoms, in other patients, including patients with pre-existing asthma, the inflammation persists leading to several types of conditions, including but not limited to asthma-like conditions, such as wheezing, where a patient has some asthma symptoms that resolve with short term treatment, asthma that progresses to a longer term condition that may or may not respond to treatment and when asthma causes severe symptoms, a patient may die.

Examples of viruses, e.g. respiratory viruses, that may contribute to induction of asthma attacks, include but are not limited to human Rhinovirus (HRV); flu (influenza) virus; parainfluenza virus; respiratory syncytial virus (RSV); metapneumovirus; coronavirus, and others. Busse, et al., "The Role of Viral Respiratory Infections in Asthma and Asthma Exacerbations." Lancet, 4:376(9743):826-834, 2010. The present invention contemplates in some embodiments infecting respiratory cells in a microfluidic device with such respiratory viruses.

In fact, one embodiment of an infected microfluidic chip, as described herein, with human rhinovirus replicates cytopathic effects and inflammatory phenotypes observed in histological sections of tissue obtained from human subjects infected with rhinovirus.

Moreover, because factors, e.g. inflamed bronchial system; virus infection; allergens; bacteria; etc. may also induce or exuberate asthma, an allergic response to or in the presence of more than one factor, i.e. co-factors, e.g. an allergen such as pollen, pet dander, etc., in combination with inflammation induced by a viral invention, may lead to a severe asthma response including severe asthma attacks. Thus, a factor, such as an allergen, may serve as a co-factor with an inflammatory response to a viral infection, to worsen an asthma attack. The present invention contemplates in some embodiments exposing respiratory cells in a microfluidic device to such factors, including but not limited to, allergens.

F. Bacteria Exacerbators.

In a variation on respiratory virus induced exacerbation of respiratory infections and asthma, bacteria may induce and/or mimic similar physical conditions in a patient. Thus, in yet further contemplated embodiments, bacteria may be used instead of viruses to mimic bacterial-induced exacerbations of asthma or respiratory infections in general. In fact, we showed that it is possible to infect the Airway Chip with bacterial pathogens for several days. Exemplary read-outs after infection include but are not limited to: real time imaging; mucociliary activity assays; immunofluorescence analysis of cell markers; cytokine analysis from effluent collections; RNA analysis of airway cells; microbial counts in effluent; microbial counts in cell samples; microbial counts of stained (direct dyes or antibodies conjugated to dyes) under real time imaging; immunofluorescenc etc.

For one example, pneumococcus is a common cause of bacterial pneumonia, an illness that can be particularly serious in a person with asthma. Thus, in one embodiment, respiratory cells with a disease phenotype (e.g. asthma, COPD, CF) may be exposed "on-chip" to *Pneumococcus* bacteria.

In another example, Group A *Streptococcus* bacteria associated with strep throat infections may be used in place of or in combination with a respiratory virus in an Airway chip. Thus, in one embodiment, respiratory cells with a disease phenotype (e.g. asthma, COPD, CF) may be exposed "on-chip" to Group A *Streptococcus* bacteria. In yet another example, a *Mycobacterium tuberculosis* (TB) bacteria may be used in an Airway chip. Thus, in one embodiment, respiratory cells with a disease phenotype (e.g. asthma, COPD, CF) may be exposed "on-chip" to *Mycobacterium tuberculosis* (TB) bacteria.

II. Infection of a Small Airway-on-Chip to Produce a Severe Asthma-on-Chip.

In some embodiments, a Small Airway-on-Chip of the present invention was infected with an exemplary virus affecting the bronchial system, e.g. a human Rhinovirus (HRV), described herein, triggering characteristics in the cell layers of the chip similar to those found in biopsies from virally infected bronchial tissue. See details in section A below. In the following sections, responses to test agents, including IL-13, were observed and measured in a microfluidic Severe Asthma-on-Chip comprising an exemplary respiratory virus, i.e. HRV.

A. Viral Infection.

In one embodiment, a Small Airway-on-Chip of the present invention comprising respiratory cells was infected with an exemplary virus affecting the bronchial system, e.g. a human Rhinovirus (HRV), thus providing a model for studying viral infections in the respiratory system and a model for drug testing.

1. Human Rhinovirus Replicates and Induces Damages to the Epithelium in the Microfluidic Airway-on-Chip.

The present invention contemplates infecting one or more respiratory cell types with a respiratory virus (including but not limited to human rhinovirus or HRV) in one embodiment of a microfluidic Airway-on-Chip. The cells can be regularly washed or simply maintained in flow conditions; in some embodiments the replicating virus in the wash fluid can be quantified. Typically, the majority of virus produced by infected cells was released from the cells over 6 days, with high amounts of virus released by infected cells within 24 hours. In order to identify whether the virus preferred infecting a particular cell type, infected cells can be stained for identifying individual cells. Typically, the majority of ciliated cells (green) contain virus (red), although other cell types may also be infected. Typically, cell damage is observed. In some cases, rounded cells are observed, sloughing off the epithelium in the infected cultures. Dying cells are also observed. Rounded cells filled with virus located in the cell cytoplasm are observed. An exemplary virus, Human rhinovirus 16 (HRV16: A16 or type 16, referring to a single stranded RNA virus), in capsid form, was added at a multiplicity of infection of 2 to the upper channel and incubated at 33° C. for 3 hours. Infected chips (n=3) were washed apically (upper channel) daily and replicating virus in the wash fluid was quantified. HRV16 Titer (Log 10 TCID 50/mL) vs time post infection (hours). TCID50 refers to a tissue culture infectious dose, which will infect 50% if the cells in a monolayer challenged with the viral inoculum.

The majority of virions produced by infected cells were released from the cells over 6 days, with high amounts of virions released by infected cells within 24 hours. See, FIG. 4A. Visually, phase contrast micrographs compare a non infected cell layer of healthy cells, at 24 hours after a duplicate chip was infected, to rounded infected cells lifting off of the surface of the chip membrane, see, FIGS. 4B and 4C. In order to identify whether the virus preferred infecting a particular cell type, infected cells were stained for cilia and HRV-16 with cell nuclei stained for identifying individual cells. As shown in FIG. 4D, at 24 post-infection (24-hpi), the majority of ciliated cells (green) contain virus (red), an example is shown by the thick white arrow, while other cell types may also be infected, see an example shown by the thin white arrow. A blue arrow points to a rounded cell filled with virus located in the cell cytoplasm, see, FIG. 4D.

Further, cells were tested for apoptotic death by immunostaining for TUNEL reactivity. Terminal deoxynucleotidyl transferase (TdT) dUTP Nick-End Labeling (TUNEL) assay was designed to detect apoptotic cells undergoing DNA degradation during apoptosis. The method is based on the ability of TdT to label blunt ends of double-stranded DNA breaks, e.g. 3'-hydroxyl termini, then in some embodiments, the TdT labeling is detected by immunostaining, including immunofluorescent staining then visualized by florescence microscopy, flow cytometry, etc. When the cells present in an apical wash were immunostained for TUNEL reactivity, numerous apoptotic cells were identified as shown in an exemplary micrograph in FIG. 4F, where bright green or white spots indicate TUNEL positive cells, nuclei were stained by DAPI as colored blue. Results showed that rhinovirus infection induces apical sloughing of ciliated cells and apoptosis. Thus, human rhinovirus induced detachment and apoptosis of ciliated cells.

FIGS. 4A-F show an example of human Rhinovirus replicating in one embodiment of the microfluidic Airway-on-Chip. FIG. 4A is an exemplary graph of a growth curve of the virus showing replication inside of the microfluidic Airway-on-Chip over a period of 6 days, with high amounts of virus released from cells (and by disintegrating dying cells) within 24 hours. Infected chips (n=3) were washed apically daily and replicating virus was quantified. HRV 16 Titre (Log 10 TCID 50/mL) vs Time post infection (hours); FIG. 4B shows phase contrast images of Non-infected (control) cells observed at the same time as the post 24 infected cells (i.e. Non infected—24 hpi). Infected chips display high apical cell sloughing; FIG. 4C shows rhinovirus-infected HRV-16 cells in an Airway-on-Chip. Note the rounded cells sloughing off the epithelium in the infected cultures, example shown at the white arrow head (HRV-16-24 hpi); FIG. 4D shows identification of dying cells in the chip. The vast majority of cells shown here damaged by the infection are ciliated (green staining). Most of these ciliated cells are also infected with HRV-16 (red staining) e.g. cell identified by a thick white arrow while an e.g. of another cell type is identified by a thin white arrow. Nuclei are shown in blue. (24 hpi). A blue arrow points to a rounded cell filled with virus located in the cell cytoplasm; FIG. 4E shows exemplary confocal imaging of detached apical cells (from washing the apical surface) showing that most detached cells are HRV-infected ciliated cells, suggesting that HRV primarily infects multiciliated cells and FIG. 4F shows HRV-16 infection induced cytopathic effects in one embodiment of an Airway Chip. Immunofluorescence staining shows TUNEL positive (apoptotic) cells in apical washes of HRV-infected chips.

2. Human Rhinovirus Specifically Damages Ciliated Cells.

In one embodiment, the infection results in damage to ciliated cells. In particular, after a number of days of Rhinovirus infection, large amounts of cilia are gone and/or the length of cilia is reduced. Comparisons can be made before and after infection. Comparisons can also be made between microfluidic devices, e.g. where in one device infection takes place and in another (control) device the cells are not infected.

In particular, after 6 days of Rhinovirus infection large amounts of cilia are gone, FIG. 5A, right panel, as supported by an exemplary graph in FIG. 5B showing significant loss of ciliated areas and significant loss in length of remaining cilia, see FIG. 5C. White arrows point to exemplary ciliated cells. Thus, in one example, at 6 days post infection (dpi), ciliated cells have almost completely disappeared from the epithelial surface.

FIGS. 5A-E show an example of human Rhinovirus specifically damaging ciliated cells. FIG. 5A is a micrograph of fluorescent imaging of ciliated cells (stained cilia are shown in green with stained cell nuclei shown in blue) before (left) and after Rhinovirus infection (right) 6 days after infection (6d: 6 dpi). Note the large amounts of cilia in the left panel as opposed to the almost total destruction of ciliated cells at the end point of the infection in the right panel. Examples of ciliated cells are identified by white arrows. FIG. 5B shows graphical of the area covered by ciliated cells before and after infection. Ciliated cells (% total area) comparing non infected to HRV-16 infected chips. FIG. 5C shows graphical quantification of the length of cilia before and after infection. Note that after infection cilia are very small compared with before infection. This graph shows cilia length in pixels comparing non infected to HRV-16 infected cells. FIG. 5D shows Rhinovirus infecting ciliated cells (24 hours pi) but not detected in mucus producing cells. In fact, infected ciliated cells were observed to protrude from the epithelial surface while cilia beating frequency was reduced following infection. Upper left image shows bright green (white) labeling of beta-tubulin in ciliated cells having co-localized monoclonal (m) antibody (Ab) J2 (mabJ2) staining in red (darker areas) show locations of double-strand RNA indicative of viral replication in infected ciliated cells. DAPI stained and blue colored nuclei show in the darkest staining. Upper left image shows bright green (white) labeling of MUC5AC in goblet cells that do not appear to be co-localized with monoclonal (m) antibody (Ab) J2 (mabJ2) staining in red (darker areas) showing locations of double-strand RNA indicative of viral replication. DAPI stained and blue colored nuclei show in the darkest staining. Below each image is a cross-sectional fluorescent image of the epithelial cell layer showing (left) the presence of virus in a ciliated cell as staining positive for beta-tubulin, see white arrow, while the right lower image shows viral staining, red, that is not associated with the MUC5AC staining of goblet cells. FIG. 5E shows an exemplary result of cilia beating frequency (Hz) significantly reduced following infection.

In some embodiments, changes in cell morphology of infected ciliated cells can be observed. In some embodiments, reduced cilia beating frequency in infected cells is observed (as compared to non-infected controls. In some embodiments, cells detach from the attachment surface (e.g. channel and/or membrane).

Figure 6B:
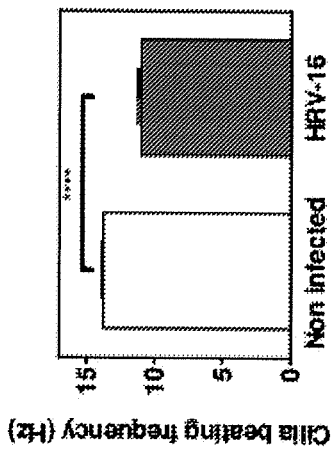
FIGS. 6A-B shows an example of human Rhinovirus induces ciliated cells rounding and reduces cilia beating frequency.
Figure 6A:
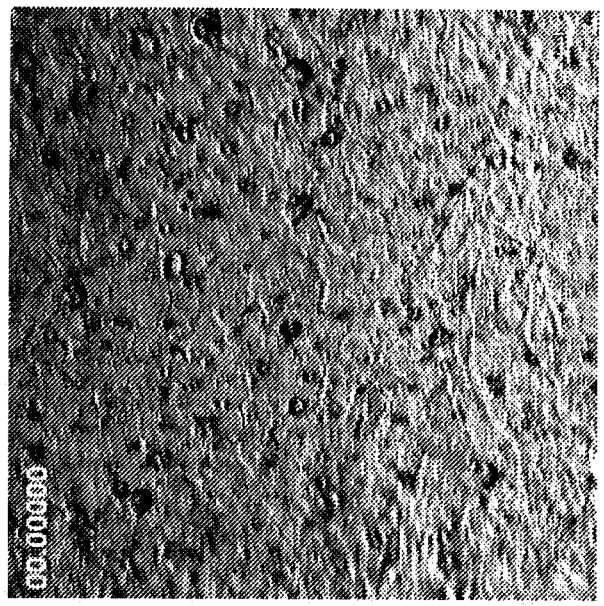

In particular, after 24 hours (h) of Rhinovirus infection ciliated cells shown, in a phase contrast micrograph, are rounded, see, FIG. 6A. Pink arrows point to exemplary rounded cells. This observation is supported by an exemplary graph in FIG. 6B comparatively measuring reduced cilia beating frequency in HRV-16 infected cells as opposed to non-infected controls.

FIGS. 6A-B shows an example of human Rhinovirus induces ciliated cells rounding and reduces cilia beating frequency. FIG. 6A shows cells at 24 h post infection: Pink arrows point to examples of rounded ciliated cells. Note the rounded cells moving (blurry) due to cilia beating. These cells are predicted to detach from the epithelium layer/membrane. FIG. 6B shows quantification of cilia beat frequency between non-infected and HRV-16 infected chips. Cilia beating frequency (Hertz: Hz) comparing frequency measured in non-infected to infected chips.

FIGS. 7A1-4-7B1-5 shows embodiments for modeling asthma exacerbation on chip by measuring cilia beating frequency and mucociliary transport on-chip for modeling changes in function of Human Airway Epithelium. Although IL-13 stimulation also reduces cilia beating frequency but do not sensitize the epithelium to rhinovirus. FIG. 7A1-4 shows a panel of micrographs along with a CBF (cilia beating frequency) (HZ) colorized scale demonstrating cilia beating in FIG. 7A1, a colorized cilia beating frequency micrograph FIG. 7A2 using a CBF scale shown in FIG. 7A3. FIG. 7A4 shows a still shot from a video micrograph of mucociliary transport (i.e. mucociliary escalator) where the white dots are fluorescent microbeads moving across the upper surface of the epithelium. FIGS. 7B1-7B21 shows a panel of micrographs demonstrating cilia beating frequency in colorized micrographs a CBF scale shown in FIG. 7B3. FIG. 7B4 shows a chart of cilia beating frequency (Hz). FIG. 7B5 shows comparative HRV-16 viral titers (Log10 TCID50/ml) showing little difference in amount of virus produced in IL-13 co-treatments.

In some embodiments, metaplasia of the cell layer is observed after infection. Metaplasia in general refers to an abnormal change in the nature of a tissue.

One example of metaplasia refers to a reversible replacement of one differentiated cell type with another mature differentiated cell type. The change from one type of cell to another may generally be a part of normal maturation process or caused by some sort of abnormal stimulus. In some embodiments, metaplasia is induced by the abnormal stimulus of the viral (e.g. HRV-16) infection. In one embodiment, after 6 days of Rhinovirus infection, in addition to the loss of cilia staining, an increased number of goblet cell staining was observed in immunofluorescent micrographs of cells in the layer.

In fact, embodiments of microfluidic devices demonstrate exemplary metaplasia of the cell layer in the upper channel of the infected Airway-on-Chip. Metaplasia in general refers to an abnormal change in the nature of a tissue.

Figures 8A, 8B, 8C, 8D:
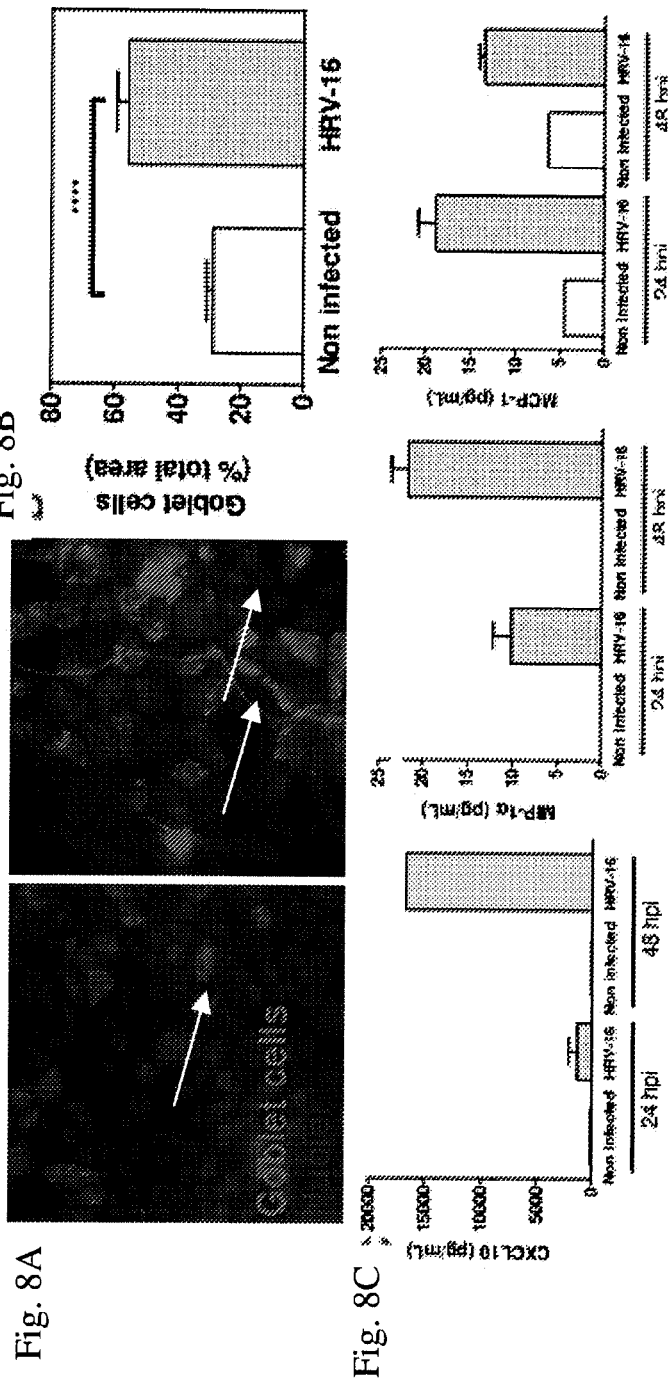
FIGS. 8A-D shows an example of human Rhinovirus induced goblet cells metaplasia and induced secretion of pro-inflammatory chemokines.

One example of metaplasia, shown here, refers to a reversible replacement of one differentiated cell type with another mature differentiated cell type. The change from one type of cell to another may generally be a part of normal maturation process or caused by some sort of abnormal stimulus. However, as supported by the data shown here, metaplasia is induced by the abnormal stimulus of the HRV-16 infection. Thus, after 6 days of Rhinovirus infection, in addition to the loss of cilia staining, an increased number of goblet cell staining was observed in immunofluorescent micrographs of cells in the layer of the upper channel of an infected chip stained with a goblet cell marker, see FIG. 8A, left panel compared to staining of goblet in a non infected chip, to right panel of FIG. 8A showing an infected chip. The observed increase goblet cells by mucin staining (red) inside of these cells, is supported by an exemplary graph in FIG. 8B showing significant increase in goblet cells as a percentage of total area. White arrows point to exemplary ciliated cells.

FIGS. 8A-B shows an example of human Rhinovirus induced goblet cells metaplasia and induced secretion of pro-inflammatory chemokines. FIG. 8A is a micrograph showing fluorescent imaging of mucus producing cells (Goblet cells (MUCSAC+)-red) before (left) or after 6 days from infection (right). Note that after infection almost all the cells are goblet cells, typical of a goblet cell hyperplasia/metaplasia. MUC5AC staining also suggests increase of apical mucus secretion. Nuclei are shown in blue. FIG. 8B shows quantification of the goblet cells hyperplasia/metaplasia after infection (6 days). Goblet cells (% total area) vs. comparing non infected to HRV-16 infected chips.

In one embodiment, infection of respiratory cells in the microfluidic device results in induced secretion of pro-inflammatory chemokines. In some embodiments, metaplasia and/or chemokine secretion is quantified.

In one embodiment, the present invention contemplates causing a pro-inflammatory response of respiratory cells in a microfluidic device by infecting the cells with a respiratory virus. In one embodiment, a time-dependent release of proinflammatory cytokines was detected, including IL-1α, IL-6, CCL2, CCL3, CCL-13, CXCL10 and Th2 associated chemokines, i.e. CCL-11 and CCL-17.

A variety of chemokines and cytokines can be measured. In one embodiment, C-X-C Motif Chemokines Ligand 10

(CXCL10) protein is secreted by HRV-16 infected cells but not non-infected cells. Secretion of MIP-1 alpha (macrophage inflammatory protein 1 alpha: a member of the CC chemokine family) and MCP-1 (Monocyte chemoattractant protein-1 (MCP-1/CCL2)) was also induced by HRV-16 infection. Both of these chemokines are known chemoattractants for neutrophils.

In particular, after 6 days of Rhinovirus infection, amounts of chemokines were measured in fluid collected from the upper and/or lower channel following 24 and 48 hours post-infection with HRV-16. C-X-C Motif Chemokine Ligand 10 (CXCL10) protein is typically secreted upon Interferon-gamma stimulation and found here to be secreted by HRV-16 infected cells but not non infected cells. Secretion of MIP-1 alpha (macrophage inflammatory protein 1 alpha: a member of the CC chemokine family) and MCP-1 (Monocyte chemoattractant protein-1 (MCP-1/CCL2)) was also induced by HRV-16 infection. Both of these chemokines are known chemoattractants for neutrophils. CXCL10 (pg/mL) MIP-1α (pg/mL) MCP-1 (pg/mL), comparing non infected to HRV-16 infected chips at 24 hpi and 48 hpi. See, FIG. 8C.

FIG. 8C shows pro-inflammatory chemokines secreted following HRV-16 infection. CXCL10 is secreted upon Interferon stimulation. MIP-1a and MCP-1 are chemoattractants for neutrophils. CXCL10 (pg/mL) MIP-1α (pg/mL) MCP-1 (pg/mL). Comparing non-infected to HRV-16 infected chips at 24 hpi (hours post infection) and 48 hpi. FIG. 8D demonstrates exemplary immunofluorescence staining showing chromatin condensation in nuclei of HRV-infected cells. HRV-16 virions are shown in red. Nuclei stained with DAPI are shown in blue.

In one embodiment, the present invention provides profiles showing secretory phases of inflammatory cytokines. In one embodiment, HRV-16-induced interferons, chemokines and pro-inflammatory cytokine profiles are altered by IL-13 treatment in the severe asthma chip as shown by high resolution, kinetic profiles of cytokine secretion. These graphs (FIGS. 17A-C) show results using a method for identifying secretory phases (i.e. I, II, III, and IV) of essential inflammatory cytokines. Here we see that IL-13 treatment inhibits secretion of IFN Lambda 1, CXCL10 and IL-6 (pg/ml) over a period of 3 days (72 hours) while infection with IL-13 results in an increase then decrease of these cytokines.

FIGS. 17A-C HRV-16-induced interferons, chemokines and pro-inflammatory cytokines profile is altered by IL-13 treatment in one embodiment of a severe asthma on-chip. These exemplary graphs show results from high resolution, kinetic profiles of an IFN Lambda 1 response FIG. 17A IP-10/CXCL10; FIG. 17B IL-6 response; FIG. 17C following HRV16 infection. A severe asthma on-chip was stimulated with IL-13 (lower red line and squares) while a duplicate chip was not stimulated with IL-13 (upper blue line and circles). IL-13 treatment was over 72 hours post infection. Data represent mean±SEM of cells from three to four different donors, with one or two biological replicates (chips) per donor.

B. Bacteria Infection.

Exemplary Adhesion Assay Protocol (method).

Exemplary on-Chip Infection and Analysis of Bacteria Aadhesion.

Bacteria from log phase cultures were collected and washed with PBS. Three (3)×10⁶ CFU/chip per strain were added to airway chips at an MOI of approximately 10. Where the multiplicity of infection or MOI refers to the ratio of microbial agents (e.g. virus, bacteria) to infection targets, in this case chips containing airway cells. Infect for 1 hour (1 hpi), wash 3× in PBS to remove nonadherent bacteria. Then trypsinize cells, collect cell sample and vortex. Serially dilute samples for CFU quantification. At least N=3.

1. *Moraxella* spp.

Respiratory pathogens involved in exacerbation, i.e. a severe phenotype, include *Moraxella* spp. Thus, in another example, *Moraxella* spp. such as *Moraxella catharctllis* may infect a microfluidic Airway Chip, e.g. a microfluidic asthma Airway Chip; a microfluidic CF Airway Chip; a microfluidic COPD Airway Chip, etc., inducing a severe phenotype on-chip. Thus, in one embodiment, respiratory cells with a disease phenotype (e.g. asthma, COPD, CF) may be exposed "on-chip" to *Moraxella* spp. bacteria.

Isolates of *Moraxella catharcillis* (MC) tested included a MC ATCC strain (ATCC #25238) compared to a MC clinical isolate strain (isolated from one patient). In some embodiments, these bacteria (ATCC strain) are found inside (intracellular) the epithelial cells following infection of a microfluidic Airway Chip, see, FIG. 18. However while the ATCC strain shows a more intracellular straining, the clinical strain *M. catarrhalis* 21 (clinical isolate) shows aggregates and biofilm-like growth forming on the airway epithelium. Thus, in some embodiments, infection with a *Moraxella* spp. (clinical isolate) forms biofilms (including biofilm-like structures and microcolonies), see, FIG. 19B vs. FIG. 19A.

Therefore, *Moraxella catharallis* bacteria are found inside the epithelial cells following infection of a microfluidic Airway Chip. This exemplary confocal image of the infected Airway chip shows intracellular staining (green), FIG. 18. For comparison, transwells infected with 10⁶ CFU per transwell, at a MOI of 10, have no observable stained bacteria.

Figure 18:
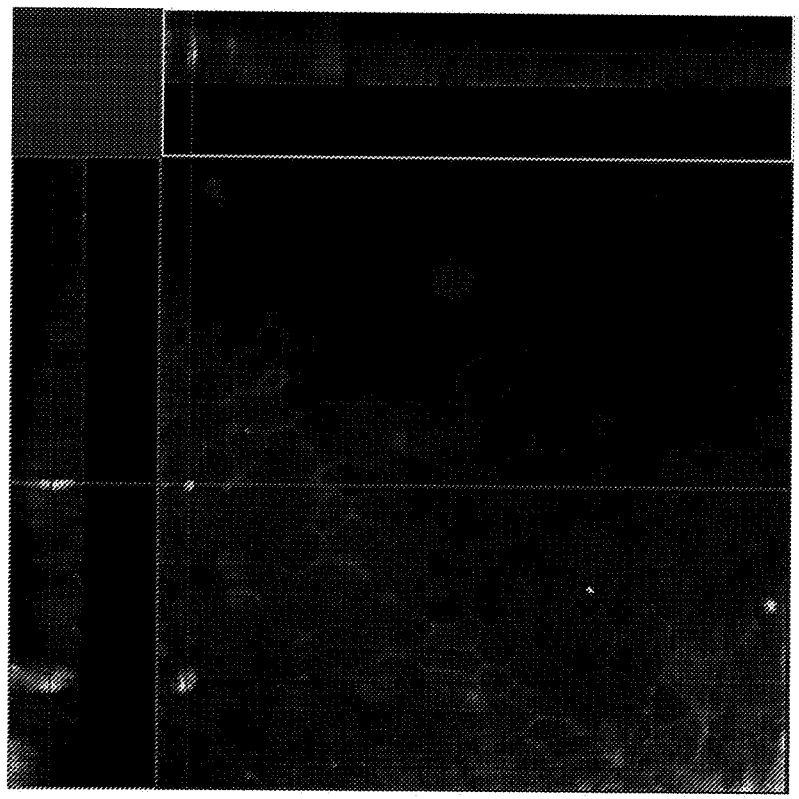
FIG. 18 shows an exemplary bacterial exacerbator infecting one embodiment of a microfluidic Airway On-Chip, including Z-stacks across the top and along the right hand side of the image. Respiratory pathogens involved in exacerbation include *Moraxella catharallis*. The upper (or right side on the side bar) part of the Z-stacks represent apical regions then down through the cells to the basil regions at the bottom of bar (or left side of the side bar). These Z-stacks indicate that bacterium is intracellularly located. Therefore, *Moraxella catharallis* bacteria are found inside the epithelial cells following infection of a microfluidic Airway Chip. This exemplary confocal image of the infected Airway chip shows intracellular staining (green). For comparison, transwells infected with $10^6$ CFU per transwell, at a MOI of 10, have no observable stained bacteria.

FIG. 18 shows an exemplary bacterial exacerbator infecting one embodiment of a microfluidic Airway On-Chip, including Z-stacks across the top and along the right hand side of the image. Respiratory pathogens involved in exacerbation include Moraxella catharallis. The upper (or right side on the side bar) part of the Z-stacks represent apical regions then down through the cells to the basil regions at the bottom of bar (or left side of the side bar). These Z-stacks indicate that bacterium is intracellularly located. This exemplary confocal image of the infected Airway chip shows intracellular staining (green). For comparison, 10⁶ CFU per transwell, MOI 10, no observable stained bacteria.

FIGS. 19A-B shows exemplary infection of one embodiment of an Airway Chip with bacteria Moraxella catharalis (MC), two different strains used at MOI 10 (10⁶ CFU per chip) at 24 post-infection (hpi). Bacteria are labeled in green. Biofilm formation (including biofilm-like structures and microcolonies) is observed on top of epithelial cells. We showed that it is possible to infect the Airway Chip with bacterial pathogens for several days. FIG. 19A MC ATCC strain; FIG. 19B MC clinical isolate strain.

2. *Pseudomonas* spp.

In another example, *Pseudomonas* spp. such as *Pseudomonas* (*P.*) *aeruginosa* (PA) may infect a microfluidic Airway Chip, e.g. a microfluidic asthma Airway Chip; a microfluidic CF Airway Chip; a microfluidic CF Airway Chip, etc., inducing a severe phenotype on-chip. Thus, in one embodiment, respiratory cells with a disease phenotype (e.g. asthma, COPD, CF) may be exposed "on-chip" to *Pseudomonas* spp. bacteria.

At least two strains of *Pseudomonas aeruginosa* were used in this study: MB5919 WT efflux competent strains; and a MB5919 derivative MB5890 multi efflux-pump defective (6-pump knock-out (KO)) mutant strain. See for details, Balibar and Grabowicz, "Mutant Alleles of 1ptD Increase the Permeability of *Pseudomonas aeruginosa* and Define Determinants of Intrinsic Resistance to Antibiotics." *Antimicrob. Agents Chemother.* 60:845-854, 2016. In this 2016 publication, both strains were transfected with plasmids for disrupting LptD, a β-barrel transmembrane transport protein, the final protein involved in Lipopolysaccharides (LPS) transfer of Lipid A of LPS into the outer membrane of gram-negative bacteria. Lipopolysaccharide (LPS) refers to a main component of the outer membrane of Gram-negative bacteria, which provides a barrier for hydrophobic drugs. Both mutations lead to the deletion of a alpha-helical loop which increases extracellular access of antibiotics into the lumen of the defective β-barrel, thus increasing susceptibility of the LPS compromised bacteria to a range of antibiotics, including Imipenem.

MB5919 WT strains; and a MB5890 multi efflux-pump mutant strain that is more susceptible to antibiotics than WT strains. Efflux pumps in general allow microorganisms to regulate their internal environment by removing compounds, including but not limited to: toxic substances, e.g. drugs, antimicrobial agents; metabolites; quorum sensing signal molecules; etc.. Further, these efflux systems are used by the bacterium to pump solutes out of the cell. More specifically, drug efflux is one mechanism of antimicrobial resistance found in Gram-negative bacteria. Bacterial drug efflux pumps have been classified into six families by having combinations of: number of components, number of transmembrane-spanning regions, energy source used by the pump and the types of molecules that the pump exports: (1) the ATP-binding cassette (ABC) superfamily; (2) the major facilitator superfamily (MFS); (3) the multidrug and toxic compound extrusion (MATE); (4) the small multidrug resistance (SMR) family; (5) the resistance-nodulation-division (RND) superfamily; and (6) the drug Metabolite transporter (DMT) superfamily.

The major clinically relevant efflux systems in *P. aeruginosa* belong to the RND superfamily and are typically composed of a cytoplasmic membrane pump, a periplasmic protein and an outer membrane protein channel. Multidrug resistance (MDR) pumps play a role in the antibiotic resistance of *P. aeruginosa*. This microorganism presents several putative MDR efflux pump-encoding genes belonging to the RND family of bacterial transporters. Among these, MexAB-OprM, MexCD-OprJ, MexEFOprN and MexXY have been the most widely studied (ref 1). MB5919 refers to *P. aeruginosa* PAO1. MB5890 refers to efflux-deficient *P. aeruginosa* PAO1 Δ(mexAB-oprM):FRT Δ(mexCD-oprJ): FRT Δ(mexXY):FRT Δ(mexJKL):FRT Δ(mexHI-opmD): FRT Δ(opmH): FRT mutant (ref 2). ref 1: Virulence 4:3, 223-229; Apr. 1, 2013; ref 2: Balibar and Grabowicz, "Mutant Alleles of 1ptD Increase the Permeability of Pseudomonas aeruginosa and Define Determinants of Intrinsic Resistance to Antibiotics." *Antimicrob. Agents Chemother.* 60:845-854, 2016.

In an exemplary but nonlimiting manner, bacteria added to epithelial cells first adhere to epithelial cells (either directly or by attaching to mucin layers); and start forming microcolonies, biofilm-like structures, and biofilms. Some bacteria enter spaces in between cells and some bacteria enter cells to become intracellular.

Figures 20A, 20B:
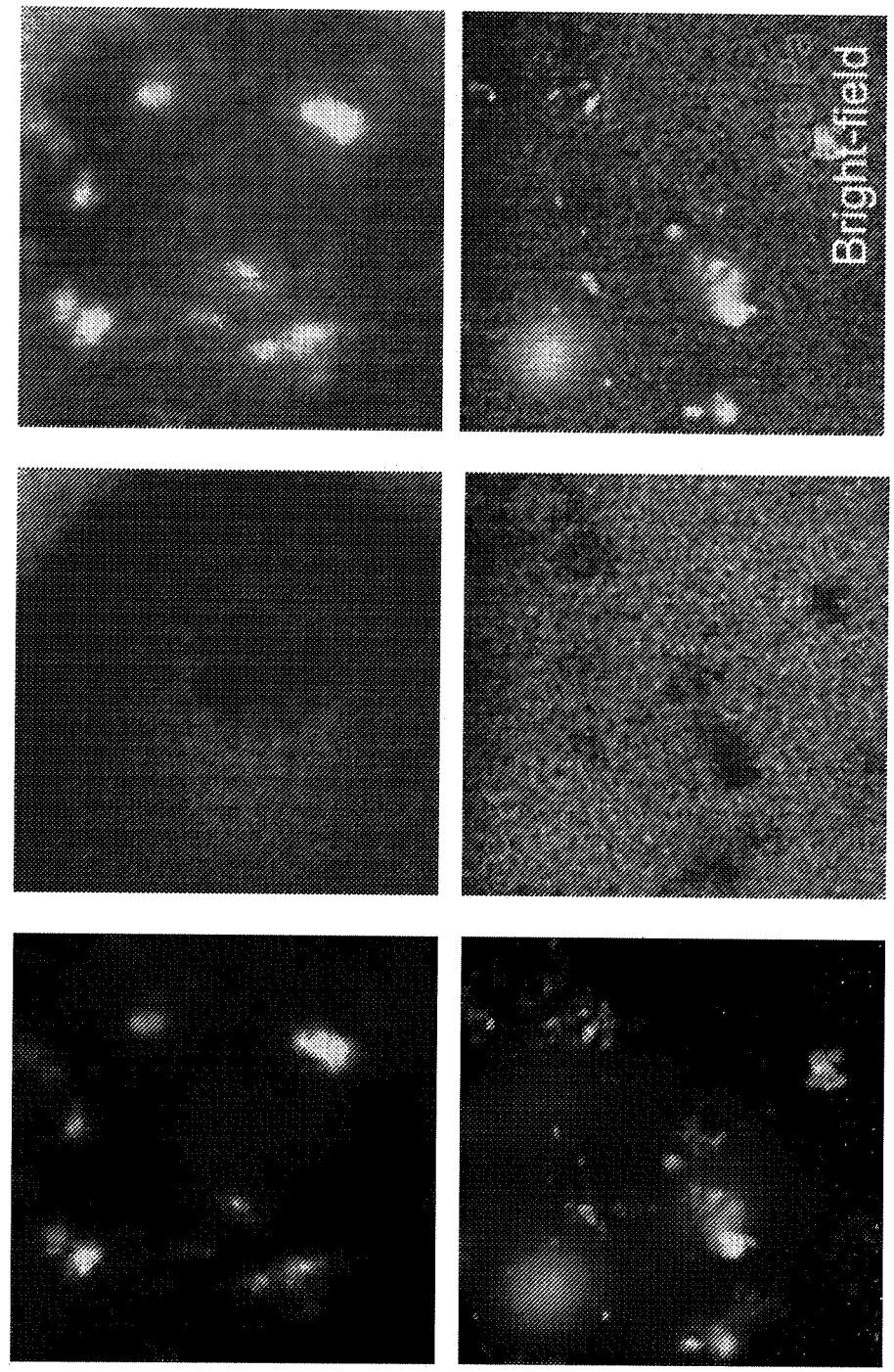
FIGS. 20A-B shows exemplary real time imaging after infection of one embodiment of an Airway Chip with bacteria *P. aeruginosa* infection on chip. Both pseudomonas strains, wild-type (WT) and mutant, form micro-colonies/aggregates on airway chip. Bacterial inoculum was plated and CFU were counted to ensure target MOI. Images were acquired 24 hpi.

In some embodiments, these bacteria are found inside (intracellularly in) the epithelial cells following infection of a microfluidic Airway Chip. In some embodiments, these bacteria form extracellular micro-colonies/aggregates following infection of a microfluidic Airway Chip. FIGS. 20A-B shows exemplary *P. aeruginosa* infection on chip with WT (top) and efflux pump mutant strains (bottom) at 24 hpi. Both strains form microcolonies on airway epithelium. Microfluidic Chip Emulates Damage Induced by Infectious Microbes: i.e. Changes in Mucociliary Activity.

Exemplary on-chip infection protocol. Bacteria from log phase cultures were collected and washed with PBS. Three $(3) \times 10^6$ CFU/chip per strain were infected at an MOI of approximately 10. Infect for 2 h, wash 3×PBS to remove nonadherent bacteria.

FIGS. 20A-B shows exemplary real time imaging after infection of one embodiment of an Airway Chip with bacteria *P. aeruginosa* infection on chip. Both pseudomonas strains, wild-type (WT) and mutant, form micro-colonies/aggregates on airway chip. Bacterial inoculum was plated and CFU were counted to ensure target MOI. Images were acquired 24 hpi. FIG. 20A PA 5919-WT. FIG. 20B PA 5890-Mutant. Left: Alexa fluor 488-anti-*P. aeruginosa* (Pa) antibody. Central: Bright-field. Right: Alexa fluor 488-anti-*P. aeruginosa* (Pa) antibody-Bright-field.

Figure 21A:
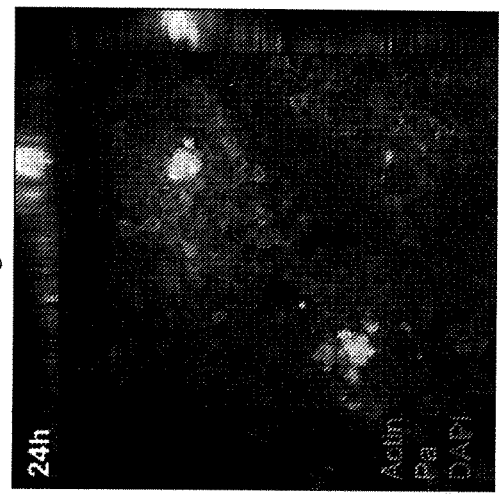
FIGS. 21A-C shows exemplary immunofluorescence, with Z-stacks or a side view, after infection of one embodiment of an Airway Chip with bacteria *P. aeruginosa* infection on chip. Pseudomonas establishes an intracellular niche as well as forming extracellular micro-colonies on the epithelial cell surface. Z-stacks are shown as a bar across the top (to the right of the 24 h label, and the down the right side of the micrographs. The upper (or right side on the side bar) part of the Z-stacks represent apical regions then down through the cells to the basil regions at the bottom of bar (or left side of the side bar). These Z-stacks indicate that bacterium are intracellularly located.
Figure 21B:
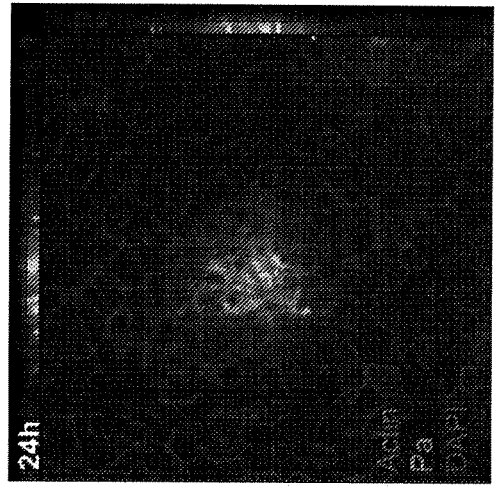
Figure 21C:
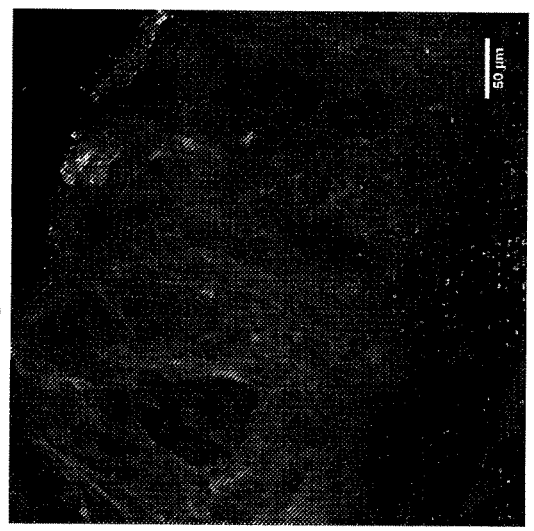

What is apparent in these images, see FIG. 21A-C, is also the rearrangement of the host cell cytoskeleton after *P. aeruginosa* infection. *P. aeruginosa* induces cytoskeletal rearrangements in the cell, particularly of the actin filaments (image with the mutant strain on the right), in order to facilitate its entry into the cell.

FIGS. 21A-B shows exemplary immunofluorescence, with Z-stacks or a side view, after infection of one embodiment of an Airway Chip with bacteria *P. aeruginosa* infection on chip. *Pseudomonas* establishes an intracellular niche as well as forming extracellular micro-colonies on the epithelial cell surface. Z-stacks are shown as a bar across the top (to the right of the 24 h label, and the down the right side of the micrographs. The upper (or right side on the side bar) part of the Z-stacks represent apical regions then down through the cells to the basil regions at the bottom of bar (or left side of the side bar). These Z-stacks indicate that bacterium is intracellularly located. FIG. 21A PA 5919-WT. Actin (red); Pa (green); DAPI (blue). FIG. 21B PA 5890-Mutant. Actin (pink); Pa (green); DAPI (blue). Images were acquired 24 hpi. FIG. 21C shows a confocal immunofluorescent micrograph side view of a cell layer infected with *P. aeruginosa* in a microfluidic airway chip, 24 hours post infection. Actin (pink); Pa (green); DAPI (blue). Bacterial aggregates on apical surface as well as intracellular bacteria are observed.

The effects of *P. aeruginosa* infection on the host mucociliary activity were also assessed. Ciliary beating frequencies (CBF) of uninfected and 24 h infected chips were recorded using a high-speed digital microscopy. Data was analyzed to detect changes in CBF as well as the ciliary coverage. Color table at right indicates ciliary beat frequency (CBF) of individual cilia. Ciliary coverage, which is an indication of the number of ciliated cells in a given area of the epithelium acquired, was also reduced in the infected chips compared to the control. Exemplary images and charts demonstrate mucociliary activity measured after infection, compared to uninfected airway on-chips or comparative airway on-chips.

Figure 23:
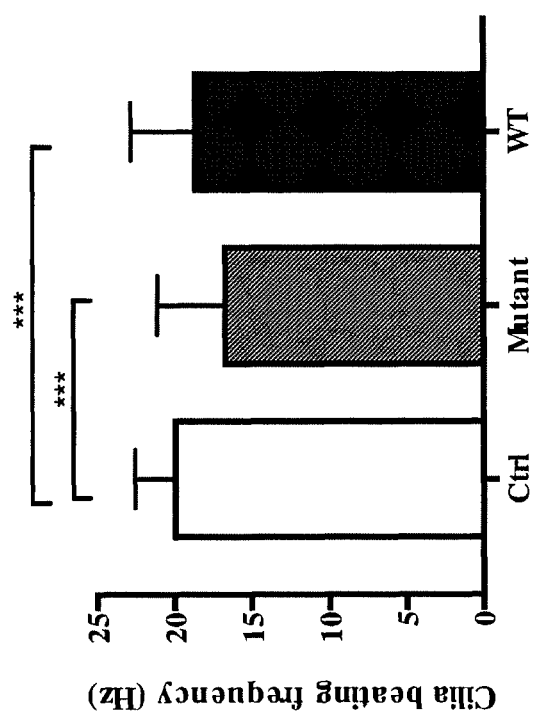
FIG. 23 shows an exemplary comparison of cilia beating frequency (CBF) between *Pseudomonas* strains in one embodiment of a *Pseudomonas* infection on chip. Images from a video of epidermal cells' cilia beating on-chip were quantitatively evaluated showing that both wild type and mutant strains has altered cilia beating frequency compared to controls without added bacteria.

FIG. 23 shows an exemplary comparison of cilia beating frequency (CBF) between *Pseudomonas* strains in one embodiment of a *Pseudomonas* infection on chip. Images from a video of epidermal cells' cilia beating on-chip were quantitatively evaluated showing that both wild type and mutant strains has altered cilia beating frequency compared to controls without added bacteria.

Figure 24:
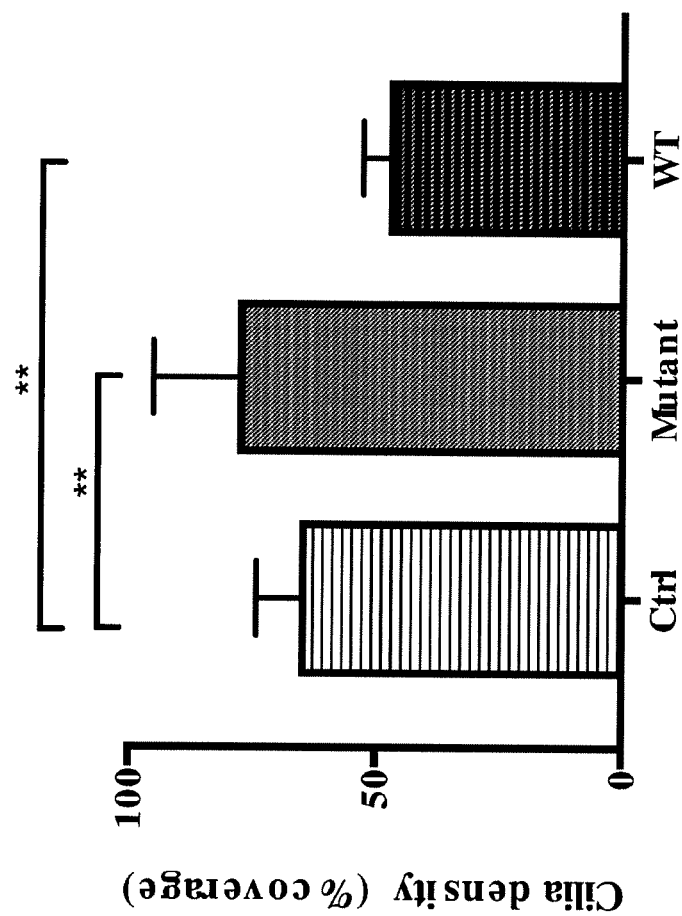
FIG. 24 an exemplary comparison of cellular cilia coverage after infection with *Pseudomonas* strains in one embodiment of a *Pseudomonas* infection on chip. Mutant (increases) and WT (decreases) show significant differences in density compared to controls.

FIG. 24 an exemplary comparison of cellular cilia coverage after infection with *Pseudomonas* strains in one embodiment of a *Pseudomonas* infection on chip. Mutant (increases) and WT (decreases) show significant differences in density compared to controls. Thus, both mutant and wildtype *P. aeruginosa* strains induce alterations in mucociliary activity.

Figure 25:
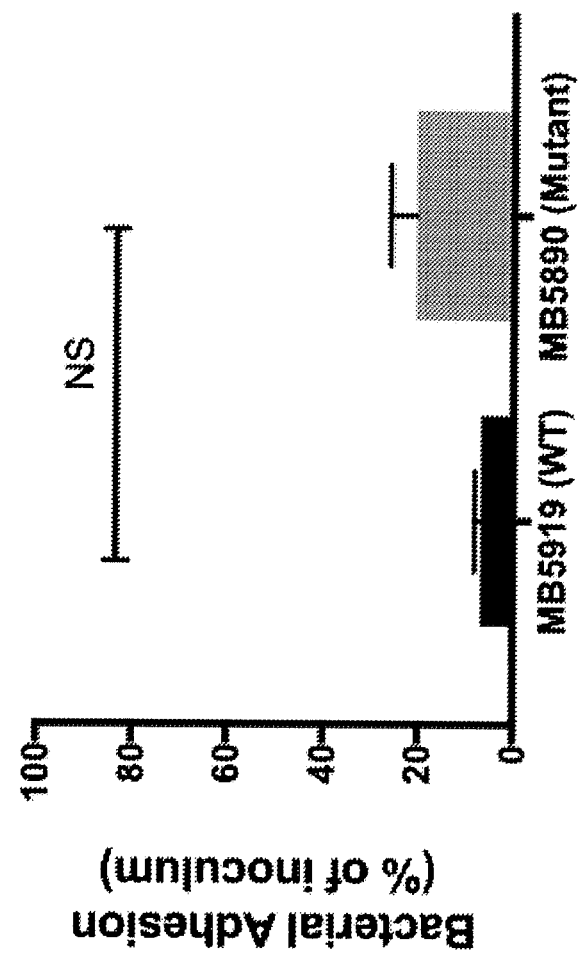
FIG. 25 shows an exemplary Bacterial adherence on chip in one embodiment of a microfluidic airway epithelia. *P. aeruginosa* WT (MB5980) and mutant (MB5919) strains adhere to airway epithelium at similar rates. Unpaired t-tests p=0.0641. N=3.

FIG. 25 shows an exemplary Bacterial adherence on chip in one embodiment of a microfluidic airway epithelia. *P. aeruginosa* WT (MB5980) and mutant (MB5919) strains adhere to airway epithelium at similar rates. Unpaired t-tests p=0.0641. N=3.

3. *S. pneumoniae* spp.

An exemplary airway on-chip was infected with *S. pneumoniae* serotype 1 at multiplicity of infection of 1 and 10, respectively for 24 h. The infection protocol follows 1) inoculation with $10^6$ or $10^7$ CFU/ml for 1 hour 2) 3×PBS wash to remove nonadhered bacteria 3) removing all media to return lung-chip at air-liquid interface 4) incubation up to 24 h of infection. Bacteria labelled in green are found intracellularly (arrows) as shown by the orthogonal z-stack section imaging by confocal microscopy. These chip experiments show that *S. pneumoniae* infection on chip closely mimics in vivo infection such as pneumonia where intracellular bacteria are reported to present in human lung and infiltrate into the tissue.

Figures 30A, 30B:
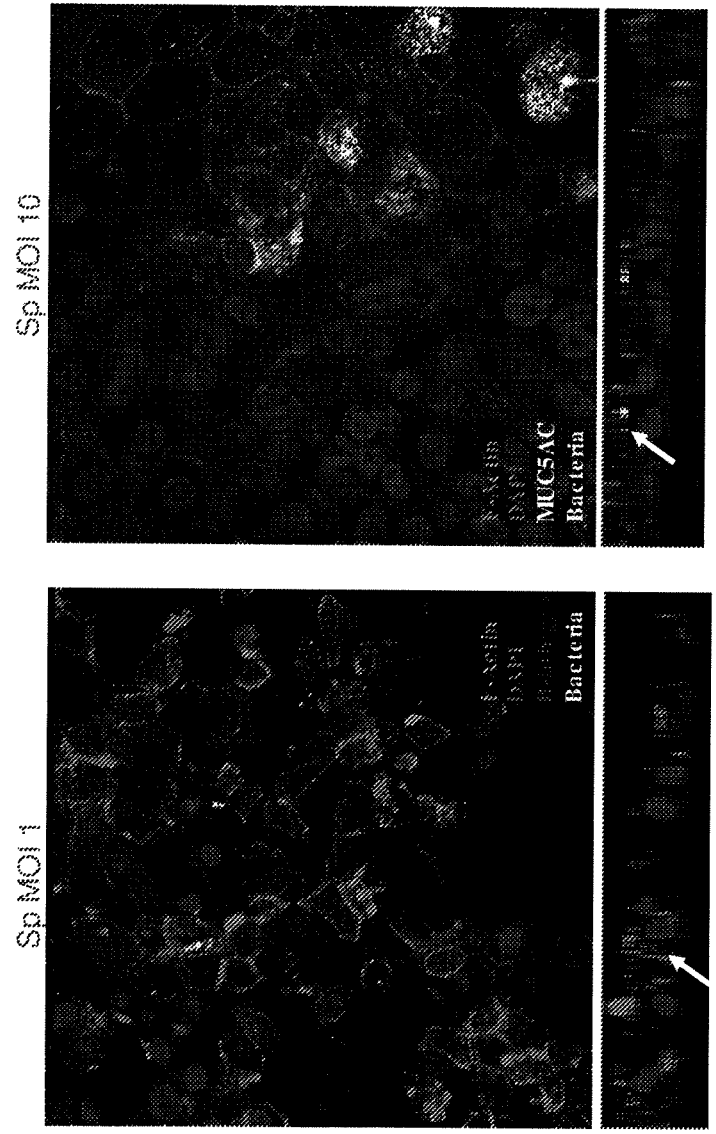
FIGS. 30A-B shows an exemplary embodiment of an airway-chip infected with *S. pneumoniae* serotype 1. Bacteria labeled in green are found intracellularly (arrows) as shown by the orthogonal z-stack section imaging by confocal microscopy.

FIGS. 30A-B shows an exemplary embodiment of an airway-chip infected with *S. pneumoniae* serotype 1. Bacteria labeled in green are found intracellularly (arrows) as shown by the orthogonal z-stack section imaging by confocal microscopy. FIG. 30A shows an exemplary infection of Sp at MOI 1. F-actin immunostain shown in red; B-tubulin immunostain shown in purple; Bacteria immunostain shown in green. Cell nuclei DAPI stained and shown in blue. FIG. 30B shows an exemplary infection of Sp at MOI 10. F-actin immunostain shown in red; MUCSAC immunostain shown in yellow; Bacteria immunostain shown in green. Cell nuclei DAPI stained and shown in blue.

Clinical Relevance of Bacteria Infection Parameters of a Lung on-Chip.

Each clinical strain may adhere to host tissue at different rates due to the variety of adhesins it expresses. Adhesins are virulence factors that allow bacteria to attach to host cells via interaction with host cell receptors e.g. pilus, fimbria, etc. Host specificity and tissue tropism are characteristics exhibited by different bacteria and are determined (at least in part) by the interaction between adhesins and their complementary receptors on host cell surfaces.

Bacterial load in lung tissue from patients with for example pneumonia has been previously quantified from bronchoalveolar lavage (BAL) and in one study reports that the quantification of bacterial counts for *Pseudomonas aeruginosa* was $\geq 10^4$ CFU/ml in BAL fluid cultures corresponding with histological pneumonia in bronchoscopically guided biopsies (Tones et al, Thorax 1996). One study reports that sputum, BAL and protected specimen brush samples from CF patients revealed a bacterial load of $\geq 10^6$/ml *Pseudomonas aeruginosa* in their samples (Aaron et al, European Respiratory Journal 2004 24: 631-637). Therefore, the CFU levels on lung-chip are within the physiologically relevant and clinical range.

For *Streptococcus pneumonia*, up to approximately $10^8$ CFU/mL of bacterial pathogen have been reported to be present in infected human lungs (Rai et al Proc Natl Acad Sci USA. 2015, 112(26): E3421-E3430, Piroth et al Antimictobial Agents and Chemotherapy, 1999, p. 2484-2492).

FIGS. 21A-C shows exemplary immunofluorescence, with Z-stacks or a side view, after infection of one embodiment of an Airway Chip with bacteria *P. aeruginosa* infection on chip. *Pseudomonas* establishes an intracellular niche as well as forming extracellular micro-colonies on the epithelial cell surface. Z-stacks are shown as a bar across the top (to the right of the 24 h label, and the down the right side of the micrographs. The upper (or right side on the side bar) part of the Z-stacks represent apical regions then down through the cells to the basil regions at the bottom of bar (or left side of the side bar). These Z-stacks indicate that bacterium is intracellularly located. FIG. 21A PA 5919-WT. Actin (red); Pa (green); DAPI (blue). FIG. 21B PA 5890-Mutant. Actin (pink); Pa (green); DAPI (blue). Images were acquired 24 hpi. FIG. 21C shows a confocal immunofluorescent micrograph side view of a cell layer infected with P. aeruginosa in a microfluidic airway chip, 24 hours post infection. Actin (pink); Pa (green); DAPI (blue). Bacterial aggregates on apical surface as well as intracellular bacteria are observed.

Observing Changes in Mucociliary Activity, i.e. Readouts.

Exemplary cilia beating frequency assay. *Pseudomonas* infection alters cilia beating frequency and cilia coverage, see, FIGS. 22A-C, FIG. 23 and FIG. 24. Both mutant and wildtype strains induce alterations in mucociliary activity. FIGS. 22A-C and FIG. 23 shows exemplary reduced cilia beating frequency after infection with *Pseudomonas* strains.

Figure 22C:
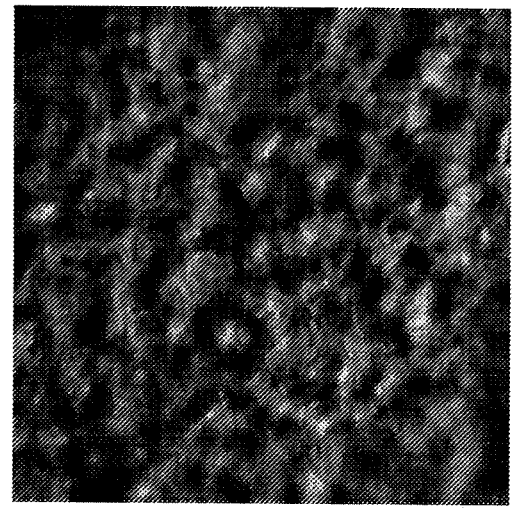
FIGS. 22A-C shows exemplary mucociliary activity photographed in bright field on one embodiment of a *Pseudomonas* infection on chip. Micrographs represent one image from a video of cilia beating on-chip.
Figure 22B:
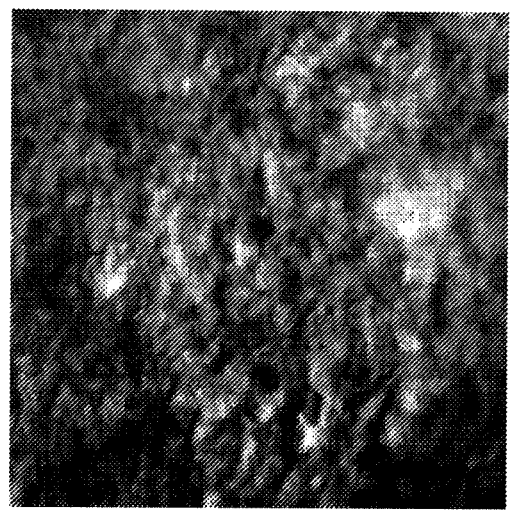
Figure 22A:
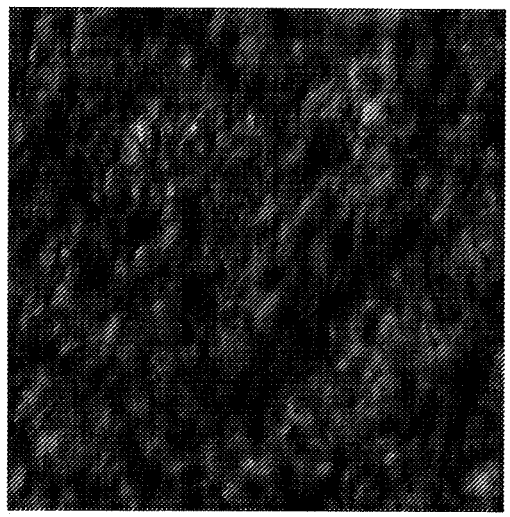

FIGS. 22A-C shows exemplary mucociliary activity photographed in bright field on one embodiment of a *Pseudomonas* infection on chip. FIG. 22A Non-infected control. FIG. 22B Mutant. FIG. 22C WT.

Quantification shows lower cilia coverage, i.e. fewer ciliated cells after infection with *Pseudomonas* strains, see, FIG. 23.

FIG. 23 shows an exemplary comparison of cilia beating frequency (CBF) between *Pseudomonas* strains in one embodiment of a *Pseudomonas* infection on chip. Images from a video of epidermal cells' cilia beating on-chip were quantitatively evaluated showing that both wild type and mutant strains has altered cilia beating frequency compared to controls without added bacteria.

FIG. 24 an exemplary comparison of cellular cilia coverage after infection with *Pseudomonas* strains in one embodiment of a *Pseudomonas* infection on chip. Mutant (increases) and WT (decreases) show significant differences in density compared to controls.

FIG. 25 shows an exemplary Bacterial adherence on chip in one embodiment of a microfluidic airway epithelia. *P. aeruginosa* WT (MB5980) and mutant (MB5919) strains adhere to airway epithelium at similar rates. Unpaired t-tests p=0.0641. N=3.

Treatment of Microfluidic Chip with an Anti-Microbial Compound.

After an exemplary on-chip infection protocol, a test compound is added to the top (apical) and bottom (basal) channels. Exemplary test compound amounts are at least 0.1 µg/ml, up to 50 µg/ml, up to 100 µg/ml, up to 500 µg/ml. In one embodiment, an exemplary test compound is a drug Imipenem.

One embodiment of an Airway on-chip was infected with PA 5919 WT or PA 5890 Mutant as described herein.

Then, Imipenem was added to apical and basolateral fluids (cell media) for treatment with imipenem at 0, 50, 100 and 500 ||g/m1 for 24 hours. At 24 h post treatment, wash cells 3× to remove the test drug, i.e. antibiotic Imipenem. Cells lysed with 1% Triton for 10 minutes. Serially diluted for CFU quantification. N=2

Assay readouts: Viability of extracellular bacteria (apical sampling). Viability of intracellular bacteria (cell lysis and sampling). Two-way ANOVA with Dunnett's post-test <0.05, <0.001 (compared to untreated).

Imipenem treatment has significant bactericidal effect on MB5890 (mutant) strain and MB5919 (WT) growth. Imipenem kills extracellular bacteria but not intracellular bacteria in airway cells. Airway cells are impermeable to imipenem at lower concentrations. *P. aeruginosa* persists in small airway cells over time when treated with 50 µg/ml Imipenem. Thus, there is a clear reduction in bacterial load indicated by the reduction in fluorescent bacteria as shown by live imaging. Imipenem effect is demonstrated by bacterial killing and control of infection.

Figures 26A, 26B:
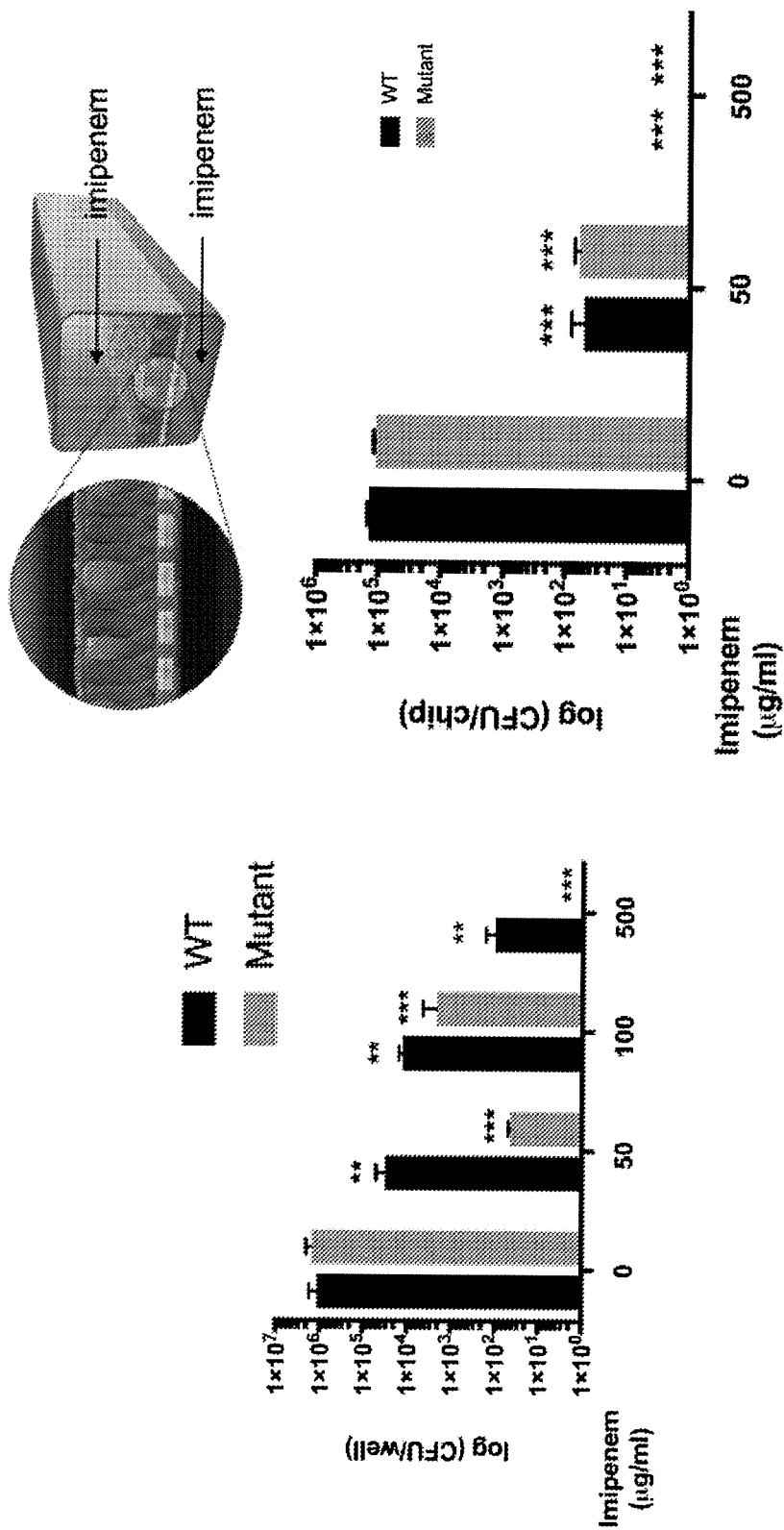
FIGS. 26A-B shows an exemplary Imipenem (Merck compound) effects on *P. aeruginosa* infection compared between Transwell cultures and on-chips.

FIGS. 26A-B shows an exemplary Imipenem (Merck compound) effects on *P. aeruginosa* infection compared between Transwell cultures and on-chips. FIG. 26A shows exemplary Imipenem (Merck compound) effects on *P. aeruginosa* infection in a Transwell culture. FIG. 26B Imipenem treatment reduces total bacterial counts via bacterial killing in one embodiment of a *P. aeruginosa* infection on chip. Two-way ANOVA with Dunnett's post-test <0.05, <0.001 (compared to untreated).

Figures 27A, 27B, 27C:
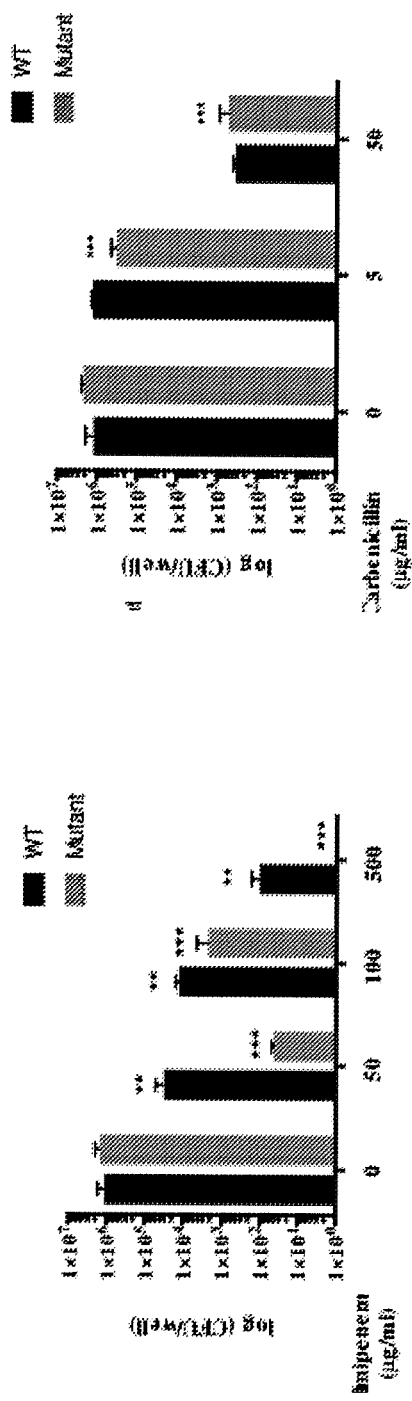
FIGS. 27A-C shows exemplary Imipenem (Merck compound) effects on *P. aeruginosa* infection, WT vs. mutant, on airway cells in Transwells.

FIGS. 27A-C shows exemplary Imipenem (Merck compound) effects on *P. aeruginosa* infection, WT vs. mutant, on airway cells in Transwells. FIG. 27A shows exemplary Imipenem treatment. FIG. 27B shows exemplary Carbenicillin treatment. FIG. 27C shows exemplary Tetracycline treatment. Two-way ANOVA with Dunnett's post-test <0.05, <0.001, ***<0.0001 (compared to untreated).

FIGS. 28A-C shows exemplary real time imaging of Imipenem effects on *P. aeruginosa* infection on one embodiment of a PA 5919 WT *Pseudomonas* infection on chip. *P. aeruginosa* infection shown on chip with WT strain (green). FIG. 28A show an untreated, infected control. FIG. 28B shows infection on-chip treated with 50 µg/ml Imipenem. FIG. 28C shows infection on-chip treated with 500 µg/ml Imipenem for 24 h. There is an obvious reduction in bacterial load indicated by the reduction in fluorescent bacteria as shown by live imaging. Imipenem effect is demonstrated by bacterial killing and control of infection. PA 5919 WT 24 hpi. Left: Alexa fluor 488-anti-*P. aeruginosa* (Pa) antibody. Central: Bright-field. Right: Alexa fluor 488-anti-*P. aeruginosa* (Pa) antibody-Bright-field.

Figures 29A, 29B, 29C:
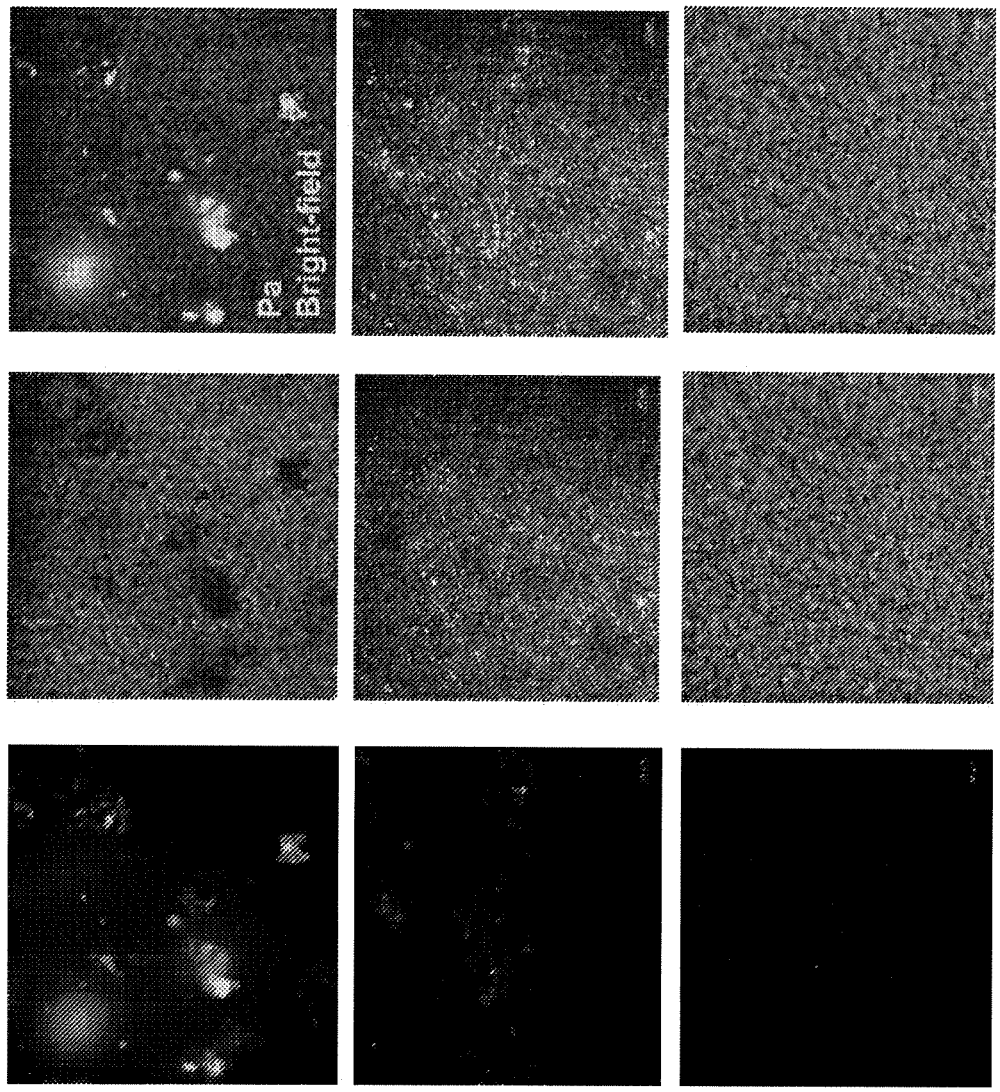
FIGS. 29A-C shows exemplary Real time imaging of Imipenem effects on *P. aeruginosa* infection on one embodiment of a PA 5890 Mutant 24 hpi *Pseudomonas* infection on chip.

FIGS. 29A-C shows exemplary Real time imaging of Imipenem effects on *P. aeruginosa* infection on one embodiment of a PA 5890 Mutant 24 hpi *Pseudomonas* infection on chip. FIG. 29A untreated (noninfected) control. FIG. 29B infection treated with 50 ug/ml imipenem. FIG. 28C infection treated with 500 ug/ml imipenem for 24 h. PA 5890 Mutant 24 hpi. Left: Alexa fluor 488-anti-*P. aeruginosa* (Pa) antibody. Central: Bright-field. Right: Alexa fluor 488-anti-*P. aeruginosa* (Pa) antibody-Bright-field.

Measuring Human β-Defensin 2 Secretion Post-infection.

Defensins in general refer to low molecular weight peptides ranging from 3 to 5 kDa, secreted from epithelia cells which have antimicrobial activity against both gram-positive and gram-negative bacteria, fungi and viruses, in addition to exhibiting pro-inflammatory properties as chemoattractants for memory T-cells, immature dendritic cells, mast cells and neutrophils. However, Beta-defensin 2 (BD-2; hBD-2) also known as skin-antimicrobial peptide 1 (SAP1) refers to an antimicrobial peptide encoded by the DEFB4 (defensin, beta 4) gene in humans which has activity mainly against Gram-negative bacteria, such as *P. aeruginosa*. hBD-2 is expressed in the epithelia of the lung, trachea, tonsils, oral tissue, skin, etc.

Figure 31:
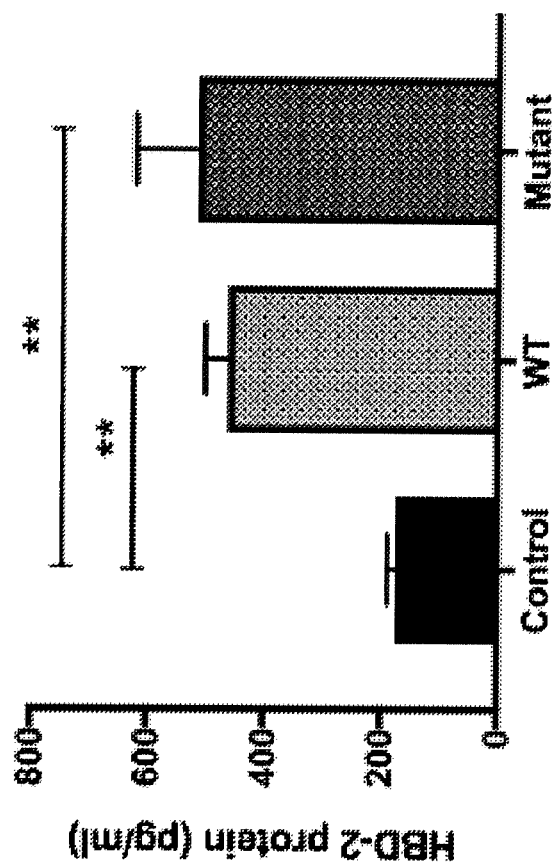
FIG. 31 shows an exemplary secretion of Human β-Defensin 2 post *P. aeruginosa* infection on one embodiment of a microfluidic Airway Chip. For comparison, HBD-2 protein (pg/ml) was measured in control chips; after WT *P. aeruginosa*; and a mutant strain of *P. aeruginosa* were tested for Human β-Defensin 2 secretion in apical wash, 24 hpi. Unpaired t-test, **<0.05. N=2.

Prolonged *P. aeruginosa* infection results in enhancement of HBD-2 protein secretion. FIG. 31: Human beta defensin 2 is detected in apical secretions in *P. aeruginosa* infected airway-chip 24 hpi.

FIG. 31 shows an exemplary secretion of Human β-Defensin 2 post *P. aeruginosa* infection on one embodiment of a microfluidic Airway Chip. For comparison, HBD-2 protein (pg/ml) was measured in control chips; after WT *P. aeruginosa*; and a mutant strain of *P. aeruginosa* were tested for Human β-Defensin 2 secretion in apical wash, 24 hpi. Unpaired t-test, **<0.05.

Induction of Apoptosis During *P. aeruginosa* Infection of an Airway on-Chip.

FIGS. 32A-D shows exemplary apoptosis via TUNEL staining at 24 h post infection. Apoptotic, TUNEL+, (pink); nuclei, DAPI+, (blue). FIG. 32A uninfected; FIG. 32B Pa infected; FIG. 32C staurosporin treatment. Staurosporin refers to an ATP-competitive kinase inhibitor. FIG. 32D DNAse I treatment. DNAse I refers to an endonuclease that nonspecifically cleaves DNA to release di-, tri- and oligonucleotide products with 5'-phosphorylated and 3'-hydroxylated ends. DNase I acts on single- and double-stranded DNA, chromatin and RNA:DNA hybrids.

C. Co-Factors Producing An Asthma-Like Phenotype.

In some embodiments, co-factors are used for inducing an asthma-like phenotype. In some embodiments, co-factors are immuno-modulatory test compounds. For example, IL-13 treatment is an exemplary co-factor and immuno-modulatory test compound. In one embodiment, the present invention contemplates inducing an asthma-like phenotype using IL-13 stimulation of airway epithelial cells. In one embodiment, epithelial cells (e.g. as a layer of cells in the upper channel with an air interface) and endothelial cells (e.g. in the lower channel under media fluid flow conditions) are employed. It was discovered that IL-13 added to this embodiment of Airway-on-Chip effects both the epithelial cell layer in the upper channel with an air interface and the endothelial cells in the lower channel under media flow conditions.

More specifically, IL-13 induced goblet cell hyperplasia. This hyperplasia effect can be inhibited by Tofacitinib, an inhibitor of the JAK/STAT pathway (Janus Kinase (JAK) and Signal Transducer and Activator of Transcription (STAT)). Thus, in one embodiment, the present invention contemplates testing drugs in the microfluidic chip that inhibit or reduce the effects of an asthma-like phenotype.

Induced gene expression for adhesion molecules was also observed after IL-13 treatment. IL-13 induced Selectins (P and E) and ICAM-1 (Intercellular Adhesion Molecule 1) and VCAM-1 (vascular cell adhesion molecule-1). Doerr, "The condition-dependent proteome." Nat Methods. 13(2):117, 2016. Gene expression was correlated with upregulated protein expression observed in fluorescently stained cells. However, it is not intended that the present invention be limited to testing for only these compounds. Other compounds can be tested for, including but not limited to, VE-Cadherin, Interleukin alpha (IL1A), Interleukin beta (IL1B), Interleukin-6 (IL6), Interleukin-8 (IL8), The chemokine (C-C motif) ligand 2 (CCL2), C-C Motif Chemokine Receptor 4 (CCR4), Protein Tyrosine Phosphatase, Receptor Type C (PTPRC), Intercellular Adhesion Molecule 1 (ICAM1), Selectin P (SELP), Selectin E (SELE), Prostaglandin-Endoperoxide Synthase 2 (PTGS2), Transforming Growth Factor Beta 1 (TGFB1), SMAD Family Member 7 (SMAD7), Complement C3 (C3), Angiotensin I Converting Enzyme (ACE), cluster of differentiation 34: CD34 antigen: CD34 molecule (CD34) and Nuclear Factor Of Activated T-Cells 4 (NFATC4).

Thus, in some embodiments, a set of changes in gene expression in a microfluidic device of the present inventions in vitro (e.g. readout) may represent at least one sub-type of asthma in vivo in a patient.

III. Immune Cells and Inflammation: Pharmacological Compounds For Reducing Asthma Associated Symptoms Induced by Viral Infections of Microfluidic Airway-on-Chips.

To recapitulate viral-induced asthma exacerbation and model molecular responses observed in severe asthma, IL-13 (as a co-factor) was used (in some embodiments) to pre-treat respiratory cells in a Severe Asthma-on-Chip followed by infection with a respiratory virus such as HRV. In one embodiment of a microfluidic Airway-On-Chip as a Severe Asthma-on-Chip, respiratory cells (e.g. lung epithelial cells) are infected with a respiratory virus affecting the bronchial system, e.g. a human Rhinovirus (HRV), before or after the cells were stimulated with IL-13.

In one embodiment, stimulation of the chip with IL-13 induced airway remodeling but does not sensitize the epithelium to rhinovirus infection (e.g. did not increase viral titers). In other embodiments, IL-13 reduced HRV16-induced interferon response and inhibits IL-6 secretion following HRV16 infection.

In some embodiments, additional cells can be included such as endothelial cells, immune cells and/or blood cells, e.g. human neutrophils for modeling inflammation in acute asthma exacerbation. In one embodiment of the Asthma-on-Chip system and method, it is contemplated that infection induced human neutrophil (PMN) cells attach and migrate into and through (across) the respiratory cells, e.g. cells providing a simulated endothelial barrier, then into the simulated epithelium lumen. Such migration models neutrophil recruitment and extravasation into the bronchial epithelial system.

IL-13 pre-treated cultures resulted in higher numbers of neutrophil recruitment (as measured by the numbers of neutrophils in the bronchial epithelial cell layer, when compared with either IL-13 stimulation or HRV infection, alone.

Further, a pharmacological compound, e.g. CXCR2 inhibitor, was added for identifying effects on neutrophils, with and without IL-13 treatment of infected cells. Relevant physiological responses, as described in examples herein, were pharmacologically inhibited, by greater than 90%, using an exemplary physiological compound, i.e. a CXCR2 antagonist (10 µM).

Microfluidic Severe Asthma-on-Chip Emulates Acute Asthma Exacerbation and Inflammation Demonstrating the Effect of a CXCR2 Antagonist on Neutrophils In one embodiment, an exemplary respiratory virus, e.g., Rhinovirus, was added to the upper channel of a microfluidic chip, IL-13 was used to stimulate cells, and neutrophils were added to the lower channel.

Neutrophils were used as immune cells in part, because neutrophils are the predominant cell type recovered from sputum during acute asthma exacerbations (Fahy, el al., "Prominent neutrophilic inflammation in sputum from subjects with asthma exacerbation." Allergy Clin Immunol. 1995; 95:843-52). However, the present invention contemplates the use of other immune cells as well.

In one embodiment, the present invention contemplates observing and/or measuring changes in immune cell behavior and characteristics as a result of infection of respiratory cells with a respiratory virus. In one embodiment, the present invention contemplates detecting and/or measuring changes in neutrophil adhesion, crawling and extravasation induced by HRV-16 infection, with and without IL-13 stimulation, that is reduced by the use of a C-X-C motif chemokine receptor 2 (CXCR2) inhibitor (in). Thus, the present invention provides a microfluidic model for testing drugs that will inhibit or reduce the changes induced in immune cells due to respiratory virus infection of respiratory cells in the chip. For example, it has been observed that HRV-16 infection resulted in an increase in neutrophil attachment in the lower channel, which was increased in cells stimulated with IL-3. While, the addition of a CXCR2 inhibitor to cells stimulated with IL-13 alone, actually increased attachment, CXCR2 inhibitor reduced neutrophil attachment for HRV-16 infections, with or without IL-13 stimulation. In another embodiment, 10 microliters of CXCR2 inhibitor (i.e. a CXCR2 antagonist) added to the lower channel reduced adhesion of neutrophil cells on endothelial cell surfaces as compared to no treatment.

In one embodiment, the present invention contemplates detecting and/or measuring movement of immune cells. For example, once recruited to the endothelium, neutrophil movement can be recorded and extravasation monitored as N (number) of spots vs. time (e.g. up to 300-600 seconds). Thus, migratory cell potential, as extravasation, can be detected and measured. For HRV-16 infection alone, the number of cells decreases as the cells move into the cell layer. When treated with a CXCR2 inhibitor, the number of cells remains about the same because the neutrophils that are attached are not moving into the cell layer. Extravasation in general refers to the movement of immune cells, such as white blood cells, into the tissues surrounding them (e.g. leukocyte extravasation), also known as diapedesis. In one embodiment, drugs can be tested in the microfluidic device (e.g. a CXCR2 antagonist) that reduce neutrophil mobility and limit trans-migration.

In one embodiment of an Airway-on-Chip, the present invention contemplates emulating acute asthma exacerbation by combining Rhinovirus infection with IL-13 stimulation in the presence of an exemplary immuno-modulatory compound. In one embodiment, comparisons can be made between treated and untreated cells, e.g. PMN (neutrophil) cells counts as % of untreated cells and cells treated with combinations shown for IL-13, HRV, and CXCR2 (in) treatments.

Thus as one embodiment, immune cells are added to the microfluidic chip in the vascular microchannel for observing changes in activation/behavior of these cells, in addition to changes in endothelial cells, epithelial cells, other immune cell types, etc. In other embodiments, primary epithelial cells derived directly from asthmatic patients are added to a microfluidic Severe Asthma-on-Chip. In some embodiments, cells are stimulated with an agent, e.g. cytokine or chemokine, such as IL-13, prior to addition to the chip. In some embodiments, cells are stimulated with an agent, e.g. cytokine or chemokine, such as IL-13, after addition to the chip. In some embodiments, instead of stimulating cells with a cytokine, primary cells derived directly from asthmatic patients are added to a microfluidic Severe Asthma-on-Chip, e.g. epithelial cells.

Immune cells, such as neutrophils, eosinophils, monocytes, macrophages, innate immune cells, lymphocytes, etc. may be added. In some embodiments, immune cells isolated from blood, i.e. buffy coats may be added as a white blood cell population or isolated into subpopulations. In some embodiments, immune cells are isolated from asthma patient blood, e.g. during asymptomatic episodes or symptomatic episodes, including severe asthma episodes, such that asthmatic patient derived immune cells are used in a microfluidic Severe Asthma-on-Chip.

Thus, a human microfluidic Severe Asthma-on-Chip provides a unique model for identifying co-factors and treatments for reducing or inhibiting severe asthma. Specifically, this physiological relevant microfluidic chip containing a 3D human airway having a 3D tissue structure and function enables the observation (and measurement) of immune cell interactions with endothelial layer (cells) and airway resident cells in real time.

Therefore, this new platform provides unique insights into asthma exacerbation co-factors and mechanisms for identification of new therapeutic target opportunities for an unmet medical need with serious implications in children and the elderly population.

IV. Exemplary Combinations of Cells, Infectious Contributions and Readouts for Generating Disease Models and Identifying Test Therapeutics.

In particular, the microfluidic device for providing a disease model comprising cells and/or tissues is generated in at least three ways, including but not limited to: a) By incorporating cells that are already diseased (e.g. cells or tissue derived from a diseased patient, e.g. patients having COPD, or cells that were exposed to a known allergen in vivo, or suspected of exposure to an allergen in vivo (i.e. for diagnostic use for identifying an allergen) or known to be already infected in vivo with a known pathogen or suspected of having an infection in vivo (i.e. for diagnostic use for identifying an infectious pathogen), b) By stimulating cells outside of the device prior to addition to the device or as the cells are being added to the device (e.g. IL-13, IL-4, IL-6, IFN, etc.), and c) By stimulating cells within the device (e.g. IL-13 induced asthma phenotype, IL-6, IFN, etc.). In some embodiments, cells stimulated outside of the device may be derived from a patient having any one or more of the following: a healthy phenotype; a particular genetic background, i.e. familial susceptibility or having a known gene sequence for a chosen gene of interest; or cells may be a cell line; a derived cell line; an immortalized cell line; etc. In some embodiments, cells derived from diseased patients are considered stimulated in vivo. In some embodiments, cells derived from diseased patients are further stimulated in vitro, as described, either outside of the device, while being added to the device or after seeding cells in the device.

Further stimulation of cells for producing a disease phenotype (non-limiting examples as described herein, e.g. stimulation with an allergen (e.g. pollen, smoke, etc.,) or microorganism (e.g. virus, bacteria, fungi, etc., as pathogenic or nonpathogenic microorganisms)) is generated in a microfluidic device in at least two additional ways, including but not limited to: a) By stimulating cells outside of the device prior to addition to the device (i.e. exposing cells before adding the cells to the microfluidic device to an allergen and/or infecting cells in the device with a microorganism), and b) By stimulating cells within the device (i.e. exposing cells in the device to an allergen and/or infecting cells in the device with a microorganism).

Evaluation of a microfluidic device, such as devices in any combination as described herein, including any combination described in the previous two paragraphs, may have one or more readouts, including but not limited to evaluating: microscopic observation (e.g. cell morphology), neutrophil recruitment (attachment to cells in vascular channel), neutrophil transmigration (presence of neutrophils in epithelial channel), mucociliary transport, frequency of cilia beating, metaplasia (e.g. percentage of goblet cells), cytokine section (e.g. IL-6), chemokine section (e.g. CCL2, IL-8), cytokine and chemokine receptor expression (e.g. CCR4, gp130), adhesion protein expression (e.g. ICAM-1), growth factor secretion (e.g. TGFB1), growth factor receptor expression (e.g. TGFR-1, ALK-1), enzyme production (e.g. ACE), cell surface receptor expression (e.g. CD34), nuclear factor expression (e.g. NFATC4), microorganism reproduction, etc.

As exemplary embodiments, a device may simulate a disease, e.g. an asthma phenotype, a COPD phonotype, etc., for readouts such as those described herein. For comparison of one more readouts, a device may be a healthy device, a device may be a disease phenotype, a device may be an exacerbation of that disease phenotype, such as an asthma device compared to an asthma exacerbation device, i.e. asthma vs. severe asthma. In some examples, a device as described herein, may be stimulated by infection with a microorganism, such as a pathogen, for a comparative readout to a duplicate device infected with a corresponding nonpathogenic strain of that pathogen. In some examples, a device as described herein, may by any of the devices described herein and described in embodiments in the two paragraphs above describing generation of stimulated devices in combination with any of the readouts described herein and in the paragraph above describing evaluation of a microfluidic device.

For examples, readouts for an asthma-on-chip may include but not be limited to mucociliary transport, frequency of cilia beating, metaplasia (e.g. percentage of goblet cells), cytokine section (e.g. IL-4, IL-6, IFNs), receptor expression (e.g. gp130, IL-4), adhesion protein expression (e.g. ICAM-1), growth factor secretion (e.g. GMCSF), growth factor receptor expression (e.g. TGFR-1, ALK-1), enzyme production (e.g. creatine kinase (CK) enzyme), cell surface receptor expression (e.g. CD34), nuclear factor expression (e.g. NFATC4), microorganism reproduction, etc.

For additional examples, readouts from microfluidic devices infected with microorganisms, pathogenic and non-pathogenic, in combination with any of the readouts described herein and in the paragraph above describing evaluation of a microfluidic device. Such infected microfluidic devices, in some embodiments do not contain an asthmatic phenotype, i.e. are without an asthmatic phenotype, or COPD phenotype, i.e. are without a COPD phenotype.

Furthermore, readouts for an infected microfluidic chip, in particular for embodiments of bacterial infection of small airway chips, include but are not limited to: Real time imaging; Mucociliary activity; Immunofluorescence; Bacterial adherence; Drug effects; etc. Even further, readouts for bacterial infection of small airway chip in the context of disease models (such as CF and COPD), include but are not limited to: 1) Colonization and time-course infection with multiple pathogens (e.g. *Moraxella catarrhalis, Pseudomonas aeruginosa, Streptococcus pneumonia,* etc.); 2) Bacterial adherence to epithelial surface and quantification of % adherence and how this may differ between different bacterial strains in terms of colony forming units (CFUs); 3) Biofilm formation (including biofilm-like structures and microcolonies) on airway epithelia; 4) Intracellular localization and intracellular survival of bacteria over time in epithelia (microscopy, CFU counting, etc.); 5) Effect of bacterial infection on ciliary beating frequency; 6) Effects of antimicrobial small compounds on bacterial killing and resolution of infection during airway infection; 7) Induction of antimicrobial peptide secretion in airway epithelia during infection, etc.

Thus as one example, in one embodiment, CFU measurements are made comparing infected microfluidic chips versus antibiotic-treated infected microfluidic chips, in part for determining effectiveness of the antibiotic under the test conditions.

Additional examples of readout embodiments are shown in the following Table 2.

TABLE 2 showing embodiments of exemplary readouts as Biomarkers for use as a guide for identifying a severe phenotype:

| Assay readout | Severe phenotype |
| --- | --- |
| Colony forming units counts | Multiplication of bacteria on tissue/increase in CFU |
| Localization of bacteria in tissue | Tissue invasion/intracellular localization of bacteria |
| Goblet cell numbers/mucus secretion | Goblet cell hyperplasia/increased mucus secretion |
| Ciliary beating frequency (CBF) | Decrease in CBF |
| Cilia coverage | Decrease in cilia coverage |
| Antimicrobial peptide (AMP) production | Increase in tissue AMP secretion |

DETAILED DESCRIPTION OF PREFERRED EMBODIMENTS

I. Respiratory Cells.

Airway cell types contributing to asthma pathogenesis include but are not limited to epithelial cells, endothelial cells, gland cells, immune cells, stromal cells, smooth muscle cells, neuronal cells, etc. Airway epithelial linings are a cellular line of defense against inhaled pathogens and particles. Thus cells in this layer include resident immune cells and immune cells recruited into airway linings, including but not limited to circulating immune cells, which initiate airway inflammation and increasing (swelling) these linings to narrow airways. Gland cells, e.g. goblet cells, produce excess mucus, also contributing to airway obstruction. Another contributory factor to airway obstruction is contraction of airway smooth muscle causing narrowing of airways and spasms. Stromal cells may also contribute with long term changes in elastic and supporting fibers. Smooth muscle cells and/or neuronal cells may also contribute with acute or long term changes, for example, hypersensitivity to inducton of spasms.

In a preferred embodiment, Severe Asthma-on-Chip comprises a fully differentiated mucociliary bronchiolar airway epithelium. In another preferred embodiment, the fully differentiated mucociliary bronchiolar airway epithelium is cultured within the microfluidic chip at an air-liquid interface. In other embodiments, Severe Asthma-on-Chip further comprises a microvascular endothelium. In some embodiment, the microvascular endothelium is grown within a fluid flow of the microchannel within the microfluidic Severe Asthma-on-Chip. In part due to spasmatic movements of airways during asthma attacks, microfluidic Severe Asthma-on-Chips are contemplated to undergo movement simulating bronchial spasms.

More specifically, the invention relates to a microfluidic Severe Asthma-on-Chip system for testing responses of cell culture systems in microfluidic devices to shear stress and various agents (including triggers and/or pharmaceutical compounds for counteracting asthmatic symptoms, etc.) introduced into the fluidic systems and/or air-liquid interface.

A. Cells for use with Microfluidic Severe Asthma-on-Chip.

In brief, a human respiratory tract includes nose/mouth, throat (pharynx) and voice box (larynx) after which inhaled air enters the windpipe (trachea). The trachea divides into two parts, a right main bronchus which supplies air to the right lung; while the left main bronchus supplies air to the left lung. These bronchi divide into smaller bronchi, of which the smallest diameter tubes are known as bronchioles. Cells from one or more of these regions of the respiratory tract can be used in a microfluidic device to mimic in vivo conditions. This system of air tubes can be referred to as an upside down tree, with the trachea being the main trunk and the bronchi and bronchioles being the branches. Alveoli are located at the end of the smallest bronchioles, i.e. respiratory bronchioles. Diverse cell types line the airways, including the alveoli, synthesize and secrete an abundance of fluids, antimicrobial proteins and mucins, and their numbers and secretory activity are influenced by injury and infection.

The human trachea, bronchi and bronchioles are lined mainly by pseudostratified epithelium whose apical cell surface lining the airway is dominated by cilia. Secretory cells, including serous, club, neuroendocrine and goblet cells, are found in relatively low numbers in normal airways. Submucosal glands secrete fluids, mucins and other host-defense proteins to cover the ciliated surface of the epithelial cells. Submucosal glands are also lined by many cell types, including myoepithelial, serous, goblet, basal and ciliated cells, that together secrete fluids and other host-defense proteins onto the airway surface, at baseline and in response to environmental stimuli.

Alveoli are lined by a thin layer of cells comprising at least two cell types. Squamous type I alveolar cells cover approximately 90% of the alveolar surface in the adult lungs and interact closely with endothelial cells of pulmonary capillaries. Other cells that line the alveoli are cuboidal type II epithelial cells. These type II cells are readily recognized histologically by their abundance of lipid-rich lamellar bodies, microvilli on their apical surfaces.

Respiratory epithelial cells create multiple barriers mediated by their secretory products, surface glycocalyces and membranes, and inter-cellular junctional proteins, the last mediated by claudins, connexins, paranexins, adhesions and zonula occludins that are linked to the actin cytoskeleton and provide structural integrity to the respiratory epithelium. Apical junctional complexes are formed by tight and adherens junctions created in part by homotypic and heterotypic binding among the many claudins expressed in pulmonary cells. As one example, loss of claudins, e.g., Cld3 and Cld4 in alveolar epithelial cells, increases alveolar-capillary permeability and inhibits fluid clearance.

Disruption of tight junctional complexes increases epithelial permeability and inflammation in both conducting airways and alveoli, which contributes to the pathogenesis of several types of respiratory diseases, including for example, asthma, acute respiratory distress syndrome, etc.

Thus, by way of example, and without limitation, a cell layer can include human airway epithelial cells (e.g., bronchiolar cells, bronchial cells, tracheal cells, etc.). Specifically, a cell layer within the microchannel can include differentiated (pseudostratified ciliated) epithelial cells. A cell layer within a microchannel can include other airway cell types, such as endothelium, fibroblasts, stromal cells, immune cells, including but not limited to neutrophils, eosinophils, macrophages, and/or other immune cells. Accordingly, the cells can be cells from one or more parts of the airways or respiratory system, including from the lungs (and the various scales of the airway tubes within the lungs, including the alveoli), the windpipe, and the nasal canal.

B. Conditions for Establishing Cells on Microfluidic Severe Asthma-on-Chip.

Epithelial surfaces of the lungs are in direct contact with the environment and are subjected to dynamic physical forces as airway tubes and alveoli are stretched and compressed during ventilation. Mucociliary clearance in conducting airways, reduction of surface tension in the alveoli, and maintenance of near sterility at these interfaces between air and epithelial cells are supported by a multi-tiered innate host-defense immune system. The biophysical nature of pulmonary host defenses are integrated with the ability of respiratory epithelial cells to respond to and 'instruct' the professional immune system to protect the airway epithelium and lungs from infection and injury.

In some embodiments, the respiratory epithelial cells are exposed on the microfluidic device to an air interface in order to mimic the conditions of the surface of the lungs in vivo. In some embodiment, the respiratory epithelial cells on the microfluidic device are subjected to stretching forces that mimic the dynamic physical forces of in vivo conditions.

C. Introduction of Agents for Providing Responses of Cells on Microfluidic Severe Asthma-on-Chip.

In addition to air, particles, (including smoke particles), microbes, chemicals, toxicants, etc., are also brought into the stimulated on-chip respiratory tract to interact with respiratory epithelial cells and host immune cells, including resident immune cells and inflammatory immune cells.

Agents may be introduced through the inlet of the epithelial or vascular channels. Cell responses to these agents may be monitored in one or more ways, including but not limited to microscopy, by measuring secreted proteins in the chip effluent, by analyzing RNA of cells, etc.

D. Exemplary Exacerbation Agents: for use with Asthma and Other Disease (Medical Condition) Chips Having Underlying Phenotypes Exacerbation of a disease or medical condition may be induced, i.e. triggered or stimulated, on-chip by the addition (exposure on-chip) of any one or more exacerbation agents, e.g. a severe asthma stimulation agent. Exposure may be short term, e.g. ranging from a few seconds, a minute, a few minutes, up to 30 minutes, up to 24 hours. Further, an induced disease phenotype, such as asthma, may be maintained by continued exposure, e.g. long term, to an exacerbation agent, e.g. more than 24 hours on-chip. Exposure may vary, such as a one-time dose (addition) of an exacerbation agent, additions of more than one dose of an exacerbation agent may be over regular intervals or by sporadic additions of more than one dose of an exacerbation agent. In embodiments comprising more than one dose, dose amounts may be equal to each other or dose amounts may be different from each other. An exacerbation agent is not limited to asthma exacerbation. Indeed, an exacerbation agent may induce at least one symptom of another respiratory condition, such as COPD, CF etc., or exacerbate symptoms of respiratory conditions, such as COPD, CF etc., e.g. using a chip comprising cells obtained from a patient having a respiratory condition, or a patient having a genetic predisposition of a respiratory condition. In other words, chips for use in exacerbation of an underlying condition, such as asthma, COPD, CF, etc., by treatment with one or more of the exacerbation agents described herein, may comprise cells harvested from patients having, or cadavers that had, one or more of asthma (i.e. asthmatics), COPD, CF, etc.; cells harvested from patients asymptomatic for, and not known to have a genetically susceptibly for, a chosen condition up until the time of biopsy, i.e. healthy cells. Such cells on-chips may be treated to induce a specific underlying phenotype, e.g. IL-13 added to a chip for inducing an inflammatory cell layer, such as inflammatory cell phenotypes observed in biopsies from asthma patients; cigarette smoke extract exposure to cells on-chip for inducing COPD like cells on-chip; etc.

Examples of exacerbation (stimulation) agents include aerosolized allergens, such as pollen; tobacco/cigarette smoke, etc., and allergens encapsulated in fluid droplets, such as by atomizers for spraying spores, virus, etc., into on-chip microenvironments. It is not meant to limit such stimulation to initial events, such that an asthma or severe asthma phenotype may be maintained by regular or sporadic addition of any one or more exacerbation agent over an extended time frame.

In some embodiments, exacerbation agents may be aerosolized as a powder for adding to the airway channel, for a non-limiting example, exposure to fine airborne particles, smoke, etc.. In some embodiments, exacerbation agents may be aerosolized in liquid droplets for adding to the airway channel, e.g. in an atomizer as a spray, for adding to the airway channel, for a non-limiting example, exposure to an insecticide, etc. In some embodiments, exacerbation agents may be added as a liquid onto the surface of airway cells. In some embodiments, exacerbation agents may be added as a liquid into the vascular channel. In some embodiments, exacerbation agents may be in a solution added to the airway channel, etc, an infectious microorganism. In some embodiments, where exacerbation agents are added as a liquid into the vascular channel, the readout includes changes from the actual exacerbation agent, e.g. insecticide, etc. In some embodiments, where exacerbation agents are added as a liquid into the vascular channel, the readout includes changes from metabolites of the exacerbation agent, e.g. medicant, such as aspirin, etc.

In some embodiments, exacerbation agents may be air samples, such as air samples containing suspected VOCs, air samples containing one or more agents described herein for testing in microfluidic chips. In some embodiments, an exacerbation agent is an actual air sample. In some embodiments, exacerbation agents may be isolated from air samples for providing more specific agents, such as VOCs from an air sample, or large or small particles, for testing in microfluidic chips. It is not meant to limit sources of exacerbation agents, such that in some embodiments sources of exacerbation agents may be commercial products, such as chemical formulations, e.g. pesticides. In some embodiments sources of exacerbation agents may mimic air conditions, such as providing a particular ozone concentration or type of particulate or concentration in the air channel of a microfluidic chip.

It is not meant that each example provided herein is a separate exacerbation agent, such that overlaps of agents, such as between fumes, gases and odors, overlaps between the types of particles emitted by burning organic matter, such as wood, etc., between volatile organic compounds (VOCs) and paint odor, may be present.

Exacerbation agents include but are not limited to infections by microorganisms or exposure to microorganisms, such as virus, e.g. respiratory virus; bacteria, such as *Aspergillus* spp., including but not limited to bronchopulmonary aspergillosis (ABPA), Proteobacteria phylum, in particular, *Haemophilus* spp., *Streptococcus* spp., *Neisseria* spp., and

*Moraxella* spp. such as *Moraxella catarrhalis, Chlamydia pneumoniae*; fungi (molds), such as spores of filamentous species within the genera of *Aspergillus, Alternaria, Cladosporius, Penicillium*, and *Didymella* (phylum *Ascomycota*), including molds found in barns, hay, released during raking leaves, mowing grass, and indoor air conditioned air; amoeboids, such as found in air conditioned air, Acanthamoeba, etc.

Exacerbation agents include but are not limited to organic sources, including but not limited to pollen (e.g. trees, e.g. alder, ash, coprosma, cypress, elm, liquidambar, maple, mulberry and plane trees; shrubs, grasses, weeds, such as ragweed, flower pollens, such as flowers in the Asteraceae family, including but not limited to daisies, marigolds, and chrysanthemums); freshly cut grass; strongly scented plants; animal dander (skin flakes), including but not limited to pets with fur or hair or feathers, e.g. cat, dog, birds, indoor birds, rabbits, chickens, guinea pigs, rats, mice, etc.; dust mites and house dust mites, including but not limited to mite feces, which are coated with enzymes that contain a powerful allergen, cast-off material from bed bugs, insect droppings, (e.g. cockroach droppings, i.e. feces); dusts from organic sources such as plants, e.g. flour; animals, e.g. dander, feather particles, saliva, feces and urine; insects, e.g. cockroach feces, cockroach saliva, etc.. Dusts may be homogenous particles or a combination of sources as dust, such as household dust combined with one or more of feather particles, bird droppings, mouse urine, mouse dander, etc. Dust may also be considered particles, as described herein.

Exacerbation agents include but are not limited to organic gases and fumes, e.g. stomach acid fumes, such as found in GERD patients.

Exacerbation agents include but are not limited to Polycyclic Aromatic Hydrocarbons (PAH), referring to a group of organic contaminants that form from the incomplete combustion of hydrocarbons, such as coal and gasoline; byproducts of petroleum processing or combustion; smoke and gases from the burning of coal refuse banks, coke production, automobiles, commercial incinerators, and wood gasifers; also formed from natural sources, including: forest fires, volcanic eruptions, and decomposition.

Exacerbation agents include but are not limited to combinations of organic and inorganic compounds, including but not limited to cosmetics, perfumes and hair sprays.

Exacerbation agents include but are not limited to inorganic gases, e.g. radon, ozone, nitrogen oxides (NOx), referring to a family of gases including but not limited to nitrogen dioxide (NO2), such as released by gas ovens, and Nitric oxide (nitrogen oxide, nitrogen monoxide), etc. NOx react with ammonia, moisture, and other compounds to form small particles, such as in the operation of motor vehicles.

Exacerbation agents include but are not limited to natural sources, such as biological decay, processes and airborne NOx produced by lightening, in part because nearby lightening may be a trigger for asthma exacerbation, and produced by burning fossil fuels like wood or natural gas, as part of wood smoke, home heaters and gas stoves, or emitted from a gas or wood stove or oven. $NO_2$ is formed indoors when $NO_2$ mixes with outdoor air to form particle pollution and ozone.

Exacerbation agents include but are not limited to chemical sprays, such as in particular, pesticide (insecticide) sprays, herbicide sprays, etc.. Thus, exacerbation agents include but are not limited to certain pesticides (insecticides); herbicides and fungicides, and their formulations, associated with triggering severe asthma. As non-limiting examples, exacerbation agents include insecticidal compounds, such as pyrethrum and pyrethrins, in the chrysanthemum family, made from crude extracts from plants or synthetic copies of these compounds or related synthetic compounds (e.g. synthetic pyrethroids, such as Permethrin, Cypermethrin, Cyfluthrin, Sumithrin, Resmethrin); cholinesterase inhibitors, such as Organophosphates (e.g. Chlorpyrifos, Diazinon, Malathion, Methyl Parathion); Carbamates, such as Carbaryl, Bendiocarb, Aldicarb, Carbofuran), e.g. Carbaryl (Sevin) carbamate, alone or in combination. As nonlimiting examples, exacerbation agents include but are not limited to certain herbicidical compounds, such as glyphosate and inert ingredients from glyphosate containing herbicide formulations; Chlorophenoxy Herbicides, e.g. 2,4-D; mecoprop and dicamba; and atrazine, alone or in combination. As non-limiting examples, exacerbation agents include certain fungicidal compounds, including but not limited to fungicides, such as chlorothalonil, fluazinam, and captafol. As non-limiting examples, exacerbation agents include certain impurities found in insecticidal formulations, which form complexes with the—cidal chemical. As non-limiting examples, exacerbation agents include certain chemicals alone, or used in cidal formulations, such as piperonyl butoxide (PBO). As non-limiting examples, exacerbation agents include combinations of agents, e.g. insect dust exacerbation agent, i.e. dust mite, cockroach, in combination with a pesticide exacerbation agent.

In some embodiments, a pesticide or related compound, such as an inert ingredient complexed with a pesticide, may be a sensitizer or irritant capable of directly damaging the bronchial mucosa, inducing a hyper-responsive mucosa, or inducing inflammation (e.g. without the use of IL-13), thus making the airway sensitive to an exacerbation agent, including but not limited to viral infection, pollen, dust mite, particles, etc.

Exacerbation agents include but are not limited to powders, dusts, emulsions, encapsulated chemicals as described herein, including but not limited to pesticides, herbicides and fungicides.

As non-limiting examples, exacerbation agents include but are not limited to fuel-burning sources (e.g. wood-burning stove); smoke from cooking, smoke from a non soy containing burning candle, smoke from a fireplace; smoke from tobacco or a tobacco product. As non-limiting examples, exacerbation agents include but are not limited to household cleaners and air-freshening sprays or devices. As non-limiting examples, exacerbation agents include but are not limited to fumes or orders, such as toxic fumes that are "off-gassing" from new products (new furniture and new carpet); building and paint products (e.g. paints, adhesives, solvents); odors (such as paint, perfumes and scented soaps. As non-limiting examples, exacerbation agents include but are not limited to volatile organic compounds (VOCs), such as VOCs emitted by the oil and gas industry, cars, trains, airplanes, ships, industrial processes, household wood fires, and incineration, as well as by plants and forests; emitted by a wide array of household consumer products such as paints and lacquers, paint strippers, cleaning supplies, pesticides, building materials and furnishings, office equipment such as copiers and printers, correction fluids and carbonless copy paper, graphics and craft materials, including but not limited to glues and adhesives, permanent markers, and photographic solutions; fumes from water-based paints and solvents.

As non-limiting examples, exacerbation agents include but are not limited to inorganic gas, such as ozone, e.g.

ground ozone, and fumes, such as formaldehyde, e.g. found in paints, wall boards, medium-density fibreboard (MDF), adhesives and more.

As non-limiting examples, exacerbation agents include but are not limited to airborne particles, such as found in haze, smoke and airborne dust, e.g. one or more compounds comprising a dust, including but not limited to particulate matter such as a dust of asbestos, pollens, molds, dirt, soil, ashes, soot, volcanic ash.

As non-limiting examples, exacerbation agents include but are not limited to airborne particles (PM), especially fine particles, containing microscopic solids or liquid droplets that are so small that they can get deep into the lungs and cause serious health problems. Sources of PM emissions include: cars, trucks, power plants, fires, agriculture, dust, industrial processes. In some embodiments, "Inhalable coarse particles," such as those found near roadways and dusty industries, refer to particles that are larger than 2.5 micrometers and smaller than 10 micrometers in diameter. In some embodiments, "Fine particles," such as those found in smoke and haze, refer to particles that are 2.5 micrometers in diameter and smaller. Fine particles are directly emitted from sources such as forest fires, or they can form when gases emitted from power plants, industries and automobiles react in the air.

As non-limiting examples, exacerbation agents include but are not limited to chemicals in the air emitted from, as non-limiting examples, factories, e.g. fossil fuel and motor-vehicle gas emissions such as sulfur dioxide, nitrogen oxides ozone and particulate matter; diesel exhaust, collectively diesel exhaust components are known as diesel exhaust particles (DEPs), referring to a mixture of fine particles and gases with chemical components including but not limited to nitrogen compounds, sulfur compounds, Polycyclic aromatic hydrocarbons (PAHs) referring to and including over 100 different chemicals that are released from burning coal, oil, gasoline, trash, tobacco, wood, or other organic substances such as charcoal-broiled meat, benzene, carbon monoxide, and PM2.5. DEPs are emitted by diesel engine powered trucks, school buses, trains, ships, harbor craft, off-road vehicles, cargo-handling and industrial equipment. PAH particulates are capable of being inhaled, they are referred to as PAH chemicals in particulate matter (PM), such as PM10 and PM2.5 in ambient air. PM10 refers to particles with a diameter of 10 micrometers or less (0.0004 inches or one-seventh the width of a human hair). PM10 includes fine particle pollution (PM2.5). Sources of PM10 emissions include: motor vehicles, wood burning stoves and fireplaces, dust from construction, landfills, and agriculture, wildfires and brush/waste burning, industrial sources, and windblown dust from open lands. Fine particle pollution can be emitted directly or formed secondarily in the atmosphere. There are different types of PM2.5. Sulfates are a type of secondary particle formed from sulfur dioxide emissions from power plants and industrial facilities. Nitrates, another type of fine particle, are formed from emissions of nitrogen oxides from power plants, automobiles, and other combustion sources.

As non-limiting examples, exacerbation agents include but are not limited to elevated levels of fine particle pollutants, such as flour, dusts, smoke, and water molecules as found in moist air, etc.

As non-limiting examples, exacerbation agents include but are not limited to ozone ($O_3$) in air. Ozone refers to a common air pollutant that exacerbates asthma in people breathing air comprising ozone. Ozone is created by the chemical interaction between nitrogen oxides (NOx) and volatile organic compounds (VOCs), in the presence of heat and sunlight. Ozone in air is measured by an Air Quality Index (AQI) developed EPA for announcing air quality (i.e. smog) alerts, such as when ozone is a health risk in both short-term exposure to ozone (based on 1-hr averaged concentrations) and longer-term exposure to ozone (based on 8-hr average concentrations). Thus, shorter and longer-term exposure to ambient ozone concentrations, in parts per billion (ppb), may provide an exacerbation asthma risk. Exemplary Air Quality Descriptors: Moderately unhealthy at Air Quality Index Values: 51-100 (60-75 ppb); Unhealthy for Sensitive Groups at 101-150 (76-95 ppb); Unhealthy at 51-200 (96-115 ppb); and Very Unhealthy 201-300 (116-374 ppb) and over (in levels found in air at ground level). Thus, in some embodiments, air entering the air channel of a microfluidic chip may contain a comparable ozone concentration as found in outside air within one of the EPA descriptors for inducing asthma exacerbation.

As non-limiting examples, exacerbation agents include but are not limited to chemical fumes, i.e. airborne chemicals, including but not limited to bleach (such as used in cleaning homes and schools), glass cleaner, detergents, ammonia, including anhydrous ammonia, hydrochloric acid (found in cleaning products), ammonium quaternary compounds, furniture polish, chlorine (such as found in swimming pools), isocyanates, chalk dust, insect spray, cleaning products, paints, or perfume, scents; such as found in polyurethane manufacturing and automobile spray painters), fumes released by new carpets, fumes released from microwave popcorn, e.g. airborne diacetyl; odors, such as air fresheners, perfume, etc.

Exacerbation agents include but are not limited to commercial products, such as chalk dust, talcum powder, powdered proteins from the inner lining of latex gloves.

Exacerbation agents include but are not limited to changes in air quality, e.g. sudden air temperature changes, such as cold, i.e. changing from 37° C. to below 20° C. down to 0° C., down to −10° C., down to −30° C.; or alternatively becoming hot, such as by changing from 37° C. up to 40° C., up to 50° C. In other embodiments, exacerbation agents include but are not limited to changes in air humidity conditions, i.e. increasing humidity, such as up to 60-100% humidity, or alternatively dryer, such as below 40%, down to 5% or less. In some embodiments, air quality is set to mimic some asthma exacerbation air quality conditions, e.g. cold-dry air or hot-moist air.

In one embodiment, in particular for use in personalized medicine, collections of particle samples from a high-efficiency particulate air (HEPA) filter (which can capture ultrafine particles) from a patient's house is added on-chip for testing for induction of severe asthma symptoms. In one embodiment, in particular for use in testing building air circulation systems, e.g., a school building, collections of particle samples from a high-efficiency particulate air (HEPA) filter are tested in a microfluidic chip for exacerbation of asthma or other respiratory disease.

Chemicals in solution and their metabolic byproducts are contemplated as exacerbation agents, including but not limited to food products, such as food preservatives, food colorings, and flavoring agents (e.g. Sodium bisulfite, potassium bisulfite, sodium metabisulfite, potassium metabisulfite, and sodium sulfite), nitrites (as in deli and sausage products), monosodium glutamate (MSG), yellow food coloring containing tartrazine); alcohol and compounds mixed with alcoholic drinks, including tainted alcohol; nicotine and related nicotine products, such as chewing tobacco, insecticides; and medicants, such as over the counter drugs, such as aspirin, prescription drugs such as Prednisone, and illegal drugs, such as heroin, and drugs such as marijuana, alone or in combination, including but not limited to aspirin, acetylsalicylic acid, salicylates; a non-steroidal anti-inflammatory drug (NSAID), such as ibuprofen, Ibruprofen (Brufen, Nurofen, Anafen, Motrin. Panafen); Naproxen (Naprosyn, Synflex, Naxen, Noflam); Keptoprofen (Orudis, Kefen, Oruvail); Indomethacin (Indocid, Arthrexin, Rheumacin); Sulinac (Clinoril, Daclin); Diclofenac (Voltaren, Apo-Diclofenac, Affenax, Diclax, Cataflam, Flameril); Mefenamic Acid (Ponstan); Piroxicam (Feldene, Candyl-D, Apo-Piroxicam, Piram-D); Diflunisal (Ansal); Tenoxicam (Tilcotil); Tiaprofenic Acid (Surgam); Flurbiprofen (Froben); acetaminophen, naproxen; Beta Blockers. Nonlimiting examples of Beta Blockers which may have an effect on asthma include but are not limited to Acebutolol (ACB); Atenolol (Lo-ten, Tenormin, Anselol, Apo Atenolol, Globel Atenolol); Celiprolol (Selectol, Celol); Labetalol (Hybloc, Trandate); Metoprolol (Betaloc, Lopressor, Slow-Lopressor); Nadolol (Apo-Nadolol); Oxprenolol (Transicor, Captol); Pindolol (Pindol, Apo-Pindolol); Propanolol (Angilol, Cardinol); Sotalol (Sotacor); Timolol (Blocadren, Hypermol); and Beta blockers administered with a diuretic: Tenoret, Tenoretic, Viskaldix.

Exacerbation agents include but are not limited to simulating hyperventilation or laughing, e.g. by increasing the frequency and/or strength of membrane stretch.

An exacerbation agent includes but is not limited to simulating a low $O_2$ condition in the airway channel of a microfluidic chip.

II. Microfluidic Chips.

According to aspects of the present inventions, a microfluidic chip system is provided for determining a response of cells.

A. Small Airway Chip

As described herein, a small airway chip recapitulates the physiology and function of the human airway epithelium. The use of a prestimulatory agent, such as IL-13, in addition of respiratory viruses, bacteria or fungi may trigger a severe asthma response in a small airway microfluidic chip. In other embodiments, the use of epithelial cells and other cells mimicking airway conditions such as CF, COPD, etc., may also be used in combination with respiratory microbial infections. The following are additional descriptions of chips and chip components.

1. Types of Cells.

Cells that may find use in microfluidic chips described herein, including but not limited to respiratory cells, bronchial and bronchiole epithelial cells, endothelium, etc., that may be obtained from cells that were cultured, immortal, primary, derived from healthy patients, cadaver, asthmatic patients, cadavers of asthmatic patients, resident cell.

It is not intended that the present invention be limited to the source of type of cells, including but not limited to generating and/or using healthy airways, diseased airways, such as CF, COPD, such as described herein. However, in one embodiment, said population of cells of step a) is selected from the group consisting of organ-restricted adult stem cells (aSCs), embryonic stem cells (ESCs), pluripotentent stem cells (PSCs), induced pluripotentent stem cells (iPSCs), organoids and stem cells isolated from lung parenchyma biopsies (or cells derived from one of these sources). In one embodiment, the cells are mammalian stem cells, e.g. human stem cells.

In one embodiment, the cells are in or from an organoid. In one embodiment, said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere, a bronchosphere, and an alveolosphere. In one embodiment, said population of cells of step a) are partially differentiated into progenitor cells.

Thus, a variety of cell sources for providing stem cells for use as described herein, include but are not limited to stem cells obtained from respiratory tissue biopsies, lung biopsies, respiratory system biopsies, embryonic stem cells (ESCs), pluripotentent stem cells, induced pluripotentent stem cells (iPSCs), organ-restricted adult stem cells (aSCs), organoids derived from primary cells, organoids derived from stem cells and organoids derived from iPS cells, in addition to other types of stem cells as described herein. Stem cell sources further include but are not limited to organoids derived from one or more cell types, (i.e. created using) including but not limited to primary cells; primary respiratory tissues; primary lung tissues; stem cells; embryonic stem cells (ESCs); or induced pluripotent stem cells (iPS cells). iPSC derived specialized organoids, may be known as tracheospheres, bronchospheres, and pneumospheres (or alveolospheres), etc. For descriptions and examples of methods that may find use for providing lung organoids, such as organoids representing the distal airways ("alveolospheres") containing both cell types in the same organoid, derived from single type 1 as well as type 2 alveolar cells, including co-culture with non-epithelial cells (e.g., mouse lung fibroblasts); early bronchiolar lung organoid culture protocol, involving Matrigel supplemented with EGF, e.g. Single basal cells isolated from the trachea grew into "tracheospheres" consisting of a pseudostratified epithelium with basal cells and ciliated luminal cells, see Clevers "Modeling Development and Disease with Organoids." *Cell,* 165(7):1586-1597 (2016).

When using transformed cells, cells may be transformed off chip prior to use. In some embodiments, cells may be transformed on-chip.

EXAMPLE A—Differentiating Stem Cells into Lung Cells on-Chip

Exemplary stem cells for use in seeding chips include but are not limited to stem cell sources described herein, including organoids derived (i.e. created) starting from one or more cell types, including but not limited to primary lung tissues, primary cells; stem cells; embryonic stem cells (ESCs); or induced pluripotent stem cells (iPS cells), or other cells as described herein. iPSC organoids may be known as tracheospheres, bronchospheres, and pneumospheres (or alveolospheres), etc., according to the lung or respiratory tissue they most closely represent.

As another example, a microfluidic chip as described herein, may be seeded by cells that were partially differentiated, i.e. not yet tenninally differentiated, e.g. as one or more populations comprising SOX17+/FOXA2+, SOX2+/FOXA2+, NKX2-1+, SOX9+ distal progenitor cells, etc., for undergoing further differentiation stages on-chip, resulting in terminally differentiated stem cell based alveolar lung-on-chip. As another example, a microfluidic chip as described herein, may be seeded by cells that were partially differentiated, i.e. not yet terminally differentiated, e.g. as one or more cell populations comprising SOX17+/FOXA2+ cells, SOX2+/FOXA2+ cells, NKX2-1+ cells, SOX2+ proximal progenitor cells, etc., for undergoing further differentiation stages on-chip, resulting in terminally differentiated stem cell based small-airway-on-chip. Such stem cell based small-airway-on-chip may included basal cells; club cells; ciliated cells; goblet cells, etc.

As another example, a microfluidic chip as described herein, may be seeded with a population of stem cells, such as any one or more populations described herein, e.g. iPS cells, EPS cells, etc. As an exemplary protocol, such stem cells may be treated with factors for inducing SOX17+/FOXA2+ cells, SOX2+/FOXA2+ cells, NKX2-1+ cells, then either inducing a predominant distal progenitor cells, e.g. SOX9+ or proximal progenitor cells, e.g. SOX2+ for undergoing terminal differentiation into alveolar cells or bronchial/tracheal cells, respectively.

As another example, a microfluidic chip as described herein and in cited publications herein incorporated by reference, may be seeded with organoids capable of differentiating into respiratory cells, lung cells, etc. In one contemplative embodiment, organoids seeded into chips may be whole, e.g. as lifted off of the tissue culture surface. In another contemplative embodiment, organoids seeded into chips may be partial, e.g. lifted off of the tissue culture surface then mechanically disrupted (e.g. vortexed), for seeding organoids as pieces. In yet other embodiments, organoids may be disrupted or sorted into single cells suspensions, e.g. filtering, flow cytometry sorting for specific markers, such as one or more of SOX2+/FOXA2+ cells, NKX2-1+ cells, SOX2+ proximal progenitor cells, etc., for seeding onto stein cell based microfluidic lung chips.

In yet other embodiments, a microfluidic chip as described herein and in cited publications herein incorporated by reference, may be used to generate lung organoids for use herein either to further differentiate on-chip or for harvesting for use in seeding a a microfluidic chip as described herein for providing a stem cell based lung-on-chip. In particular, in some embodiments, lung organoids derived from starting iPS cells involved a last stage air-liquid interphase culture that may be induced on-chip (for an example of one protocol that may used on-chip (for e.g see, Wong, A. P., Bear, C. E., Chin, S., Pasceri, P., Thompson, T. O., Huan, L. J., Ratjen, F., Ellis, J., and Rossant, J. (2012). "Directed differentiation of human pluripotent stem cells into mature airway epithelia expressing functional CFTR protein." Nat. Biotechnol. 30, 876-882), herein incorporated by reference.

In yet other embodiments, such microfluidic organoid cultures on-chips may be used for assays to screen for factors controlling generation of a particular cell type, such as alveolar type 1 vs. type II, multiciliated cells vs. percentages of secretory and basal cells.

In some embodiments, human ESC are treated with Activin A and WNT3a for 4 days then seeded onto collagen Type IV matrix in tissue culture plates. This method is known to generate table and reproducible definitive endoderm progenitor cells with >85% of the cells co-expressing CXCR4 and CD117 (cKit). The majority of the cells also co-stained for SOX17 and FOXA2. See, Wong, et al 2012. In some embodiments, cells generated with this method may instead be transferred to microfluidic devices as described herein, for subsequent additions of differentiation and maturation agents on-chips having collagen Type IV matrix coated membranes.

In some embodiments, adding high levels of FGF2 coupled with adding SHH for an additional 5 days may be used to induce definitive endoderm cells (such as SOX17+ cells) into lung progenitor (NKX2.1-expressing) cell fate. In some embodiments, after addition of FGF2 and SHH, expression of definitive endoderm marker SOX17 was down-regulated. In some embodiments, after addition of FGF2 and SHH, there may be up-regulation of anterior foregut endoderm transcription factors SOX2 and NKX2.1+. In some embodiments, progenitor cells express NKX2.1+ FOXA2+ and EpCAM. Progenitor cells obtained with this method are referred to as embryonic lung progenitors.

In some embodiments, adding FGF7 (50 ng/ml) and FGF10 (50 ng/ml) may increase expression of lung endoderm NKX2.1 and FOXA2 gene expression from embryonic lung progenitors.

Immune cells may be obtained from any one of more sources such as: resident (patient derived), isolated from blood samples (i.e. healthy people and asthmatic patients), primary, cultured, immortal, derived from differentiation procedures, including but not limited to neutrophils, eosinophils, macrophages, monocytes, lymphocytes, innate immune cells, etc.

For non-limiting examples, neutrophil and/or eosinophils are isolated from fresh human blood in one or more ways, for non-limiting examples, using different kits or differential methods of blood separation. In some methods neutrophils/eosinophils are isolated in solution by separating them from the rest of cells by using antibodies specific to certain markers for the unwanted cells that do not exist on neutrophil/eosinophils (i.e. negative selection). As one example, blood cell types are separated from each other by using a gradient of sucrose and thus cells are isolated based on their differences in density.

B. Types of Microfluidic Chips:

Several types of microfluidic chips may be used for modeling. Severe Asthma on Chips, in addition to other respiratory disorders such as CF and COPD, as described herein. These exemplary chips may have alternative options, such as closed chips, open to chips, etc., as briefly described below. While exemplary chips are described herein, additional types of chips, such as low shear chips, are contemplated for use.

1. Closed Chips.

FIG. 1A illustrates a perspective view of one embodiment of a microfluidic device with enclosed microfluidic channels (upper) with one embodiment of a microfluidic device as a CAD image (lower).

FIG. 1B illustrates an exploded view of one embodiment of a microfluidic device-showing a microfluidic channel in a top piece and a microfluidic channel in a bottom piece, separated by a membrane.

2. Open Top Chips.

FIG. 2 shows an exemplary schematic of a microfluidic device with the lid removed ("open top") comprising two chambers with microfluidics underneath.

3. Chips with Air-Liquid Interfaces and with Flow in a Lower Microchannel.

In some preferred embodiments, a 5um pore size membrane separates one microfluidic channel from another microfluidic channel. In one embodiment, a device comprising a 3 um pore size membrane supports full differentiation of human airway epithelial cells and enables recruitment and transmigration of human neutrophils. In one embodiment, viral-induced exacerbation on-chip induces neutrophil transmigration FIG. 3F shows an exemplary schematic diagram of a cross section through the Airway Chip showing its two hollow linear channels separated by a porous membrane which supports growth and differentiation of human primary airway epithelial cells on its upper surface and human pulmonary microvascular endothelial cells underneath.

III. Additional Types of Microfluidic Chips with Aerosol Delivery of Test Agents.

In one embodiment, and aerosol delivery chip model is contemplated for delivery of aerosolized agents to the air channel of microfluidic chips described herein. For example, a port specifically designed for exposing the air channel to an agent, such as smoke for inducing COPD, may be incorporated into the chip.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof. Thus, other modifications that can be employed can be within the scope of the invention.

It is to be understood that the embodiments of the invention disclosed herein are illustrative of the principles of the present invention. While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein. It is also contemplated that additional embodiments according to aspects of the present invention may remove any number of features from any of the embodiments described herein. Thus, by way of example, but not of limitation, alternative configurations of the present invention can be utilized in accordance with the teachings herein. Accordingly, embodiments of the present invention are not limited to that precisely as shown and described.

EXAMPLES

The following examples are offered to illustrate various embodiments of the invention, but should not be viewed as limiting the scope of the invention.

In one embodiment of an airway chip model, primary small airway epithelial cells (purchased from Lonza) were used. During a 3-week differentiation protocol, this embodiment of a small airway chip presents with mucus secreting goblet cells and ciliated cells with mucociliary clearance activity. There were no endothelial cells added in this embodiment. In other embodiments, primary endothelial cells will be added to this model in addition to white blood cells, e.g. neutrophils, for use in immune cell recruitment assays.

Example 1

A Microfluidic Airway-on-Chip Enables Physiological Differentiation of Human Airway Epithelial Cells.

One embodiment of an Airway-Chip was designed to study human respiratory diseases where the epithelium plays a central role (e.g., Chronic Obstructive Pulmonary Disease (COPD)). One embodiment of a microfluidic Airway-on-Chip, described herein, enables physiologically relevant differentiation of human airway epithelial cells. For one example, human primary airway cells cultured in a microfluidic Airway-on-Chip differentiate into epithelium, and in cell compositional ranges similar to in vivo airways, e.g. ciliated epithelial cells (approximately 20-30%), Goblet cells (approximately 10-20%) and basal cells (approximately 20%). In general, goblet cells refer to column-shaped cell, found in the respiratory and intestinal tracts, which secrete gel-forming mucins, as major components of mucus. In general, basal cells refer to a type of cell in the innermost layer of an epithelial tissue.

Ciliated cells in the chip are similar to those in vivo as they show similar cilia structure, e.g. length, parts, (i.e. axonemes, referring to the central strand of a cilium or flagellum, composed of an array of microtubules, typically in nine pairs around two single central microtubules) and function, (i.e. beating at frequency rates estimated as similar to cilia movements in vivo). See Tables 1A-1B.

Moreover, Goblet cells produce mucus that moves over the surface of the epithelium as part of mucociliary transport. For example, mucociliary velocity in the Airway-on-Chip is 40-100 µm/sec., within the range of velocity measured in humans. See FIG. 3A-H.

Thus a microfluidic Airway-on-Chip provides a model for studying infectious disease effects on human airway cells in vitro, such as their effects on developing respiratory conditions, such as pre-asthma, pre-COPD, etc., for effects on pre-existing respiratory conditions (e.g. asthma, COPD, etc.), for effects on respiratory conditions (e.g. asthma, COPD, etc.), and further for infectious disease effects on exacerbating respiratory conditions, e.g. severe asthma.

FIG. 3A-H shows an example of human primary airway cells cultured in a microfluidic Airway-on-Chip. FIG. 3A is a schematic representation of one embodiment of an Airway-on-Chip where cells seeded in the upper channel and grown with an air interface (blue), on top of a lower channel under media flow (red). FIG. 3B shows a colored scanning electron micrograph of ciliated cells, where cilia are artificially colored blue with gobs of mucus artificially colored brown. FIG. 3C shows a still shot (video frame) of cilia beating (blurry cilia). FIG. 3D shows an immunofluorescent micrograph of Goblet cells (red stained muccal proteins with blue colored nuclei). FIG. 3E shows a still shot from a video micrograph of mucociliary transport where the white dots are mucus globs moving across the upper surface of the epithelium. The Airway Chip described herein, recapitulates the physiology and function of the airway epithelium that conduct inhaled air to the alveolar air sacs. FIG. 3F illustrates a perspective view of one embodiment of a cross section through the Airway Chip microfluidic device with showing its two hollow linear channels (air channel above; blood channel below) separated by a porous membrane which supports growth and differentiation of human primary airway epithelial cells on its upper surface and human pulmonary microvascular endothelial cells underneath. FIG. 3G shows an exemplary scanning confocal electron micrograph of cilia forming on the differentiated airway epithelium formed on-chip (3D reconstruction showing fully differentiated, pseudostratified, airway epithelium (green, F-actin) underlined by human pulmonary endothelial cells (red, F-Actin)). FIG. 3H shows an exemplary differentiated human airway epithelium exhibiting continuous tight junctional connections on-chip, as evidenced by ZO1 staining in red enclosing the cells in black.

Example 2

Human Rhinovirus Replicates and Induces Damages to the Epithelium in the Microfluidic Airway-on-Chip.

This example shows the results of an exemplary respiratory viral infection damaging airway cells in one embodiment of a microfluidic Airway-on-Chip.

An exemplary virus, Human rhinovirus 16 (HRV16: A16 or type 16, referring to a single stranded RNA virus), in capsid form, was added at a multiplicity of infection of 2 to the upper channel and incubated at 33° C. for 3 hours. Infected chips (n=3) were washed apically (upper channel) daily and replicating virus in the wash fluid was quantified. HRV16 Titer (Log 10 TCID 50/mL) vs time post infection (hours). TCID50 refers to a tissue culture infectious dose, which will infect 50% if the cells in a monolayer challenged with the viral inoculum.

The majority of virions produced by infected cells were released from the cells over 6 days, with high amounts of virions released by infected cells within 24 hours. See, FIG. 4A. Visually, phase contrast micrographs compare a non infected cell layer of healthy cells, at 24 hours after a duplicate chip was infected, to rounded infected cells lifting off of the surface of the chip membrane, see, FIGS. 4B and 4C. In order to identify whether the virus preferred infecting a particular cell type, infected cells were stained for cilia and HRV-16 with cell nuclei stained for identifying individual cells. As shown in FIG. 4D, at 24 post-infection (24-hpi), the majority of ciliated cells (green) contain virus (red), an example is shown by the thick white arrow, while other cell types may also be infected, see an example shown by the thin white arrow. A blue arrow points to a rounded cell filled with virus located in the cell cytoplasm, see, FIG. 4D.

Further, cells were tested for apoptotic death by immunostaining for TUNEL reactivity. Terminal deoxynucleotidyl transferase (TdT) dUTP Nick-End Labeling (TUNEL) assay was designed to detect apoptotic cells undergoing DNA degradation during apoptosis. The method is based on the ability of TdT to label blunt ends of double-stranded DNA breaks, e.g. 3'-hydroxyl termini, then in some embodiments, the TdT labeling is detected by immunostaining, including immunofluorescent staining then visualized by florescence microscopy, flow cytometry, etc. When the cells present in an apical wash were immunostained for TUNEL reactivity, numerous apoptotic cells were identified as shown in an exemplary micrograph in FIG. 4F, where bright green or white spots indicate TUNEL positive cells, nuclei were stained by DAPI as colored blue. Results showed that rhinovirus infection induces apical sloughing of ciliated cells and apoptosis. Thus, human rhinovirus induced detachment and apoptosis of ciliated cells.

FIGS. 4A-E shows an example of human Rhinovirus replicating in one embodiment of the microfluidic Airway-on-Chip. FIG. 4A is an exemplary graph of a growth curve of the virus showing replication inside of the microfluidic Airway-on-Chip over a period of 6 days, with high amounts of virus released from cells (and by disintegrating dying cells) within 24 hours. Infected chips (n=3) were washed apically daily and replicating virus was quantified. HRV 16 Titer (Log 10 TCID 50/mL) vs Time post infection (hours); FIG. 4B shows phase contrast images of Non-infected (control) cells observed at the same time as the post 24 infected cells (i.e. Non infected-24 hpi). Infected chips display high apical cell sloughing; FIG. 4C shows rhinovirus-infected HRV-16 cells in an Airway-on-Chip. Note the rounded cells sloughing off the epithelium in the infected cultures, example shown at the white arrow head (HRV-16- 24 hpi); FIG. 4D shows identification of dying cells in the chip. The vast majority of cells shown here damaged by the infection are ciliated (green staining). Most of these ciliated cells are also infected with HRV-16 (red staining) e.g. cell identified by a thick white arrow while an e.g. of another cell type is identified by a thin white arrow. Nuclei are shown in blue. (24 hpi). A blue arrow points to a rounded cell filled with virus located in the cell cytoplasm; FIG. 4E shows exemplary confocal imaging of detached apical cells (from washing the apical surface) showing that most detached cells are HRV-infected ciliated cells, suggesting that HRV primarily infects multiciliated cells and FIG. 4F shows HRV-16 infection induced cytopathic effects in one embodiment of an Airway Chip. Immunofluorescence staining shows TUNEL positive (apoptotic) cells in apical washes of HRV-infected chips.

Example 3

Human Rhinovirus Specifically Damages Ciliated Cells.

This example shows the results of exemplary damage to ciliated cells.

In particular, after 6 days of Rhinovirus infection large amounts of cilia are gone, FIG. 5A, left panel, as supported by an exemplary graph in FIG. 5B showing significant loss of ciliated areas and significant loss in length of remaining cilia, see FIG. 5C. White arrows point to exemplary ciliated cells. Thus, in one example, at 6 days post infection (dpi), ciliated cells have almost completely disappeared from the epithelial surface.

FIG. 5 shows an example of human Rhinovirus specifically damaging ciliated cells. FIG. 5A is a micrograph of fluorescent imaging of ciliated cells (stained cilia are shown in green with stained cell nuclei shown in blue) before (left) and after Rhinovirus infection (right) 6 days after infection (6d: 6 dpi). Note the large amounts of cilia in the left panel as opposed to the almost total destruction of ciliated cells at the end point of the infection in the right panel. Examples of ciliated cells are identified by white arrows. FIG. 5B shows graphical of the area covered by ciliated cells before and after infection. Ciliated cells (% total area) comparing non infected to HRV-16 infected chips. FIG. 5C shows graphical quantification of the length of cilia before and after infection. Note that after infection cilia are very small compared with before infection. This graph shows cilia length in pixels comparing non infected to HRV-16 infected cells. FIG. 5D shows Rhinovirus infecting ciliated cells (24 hours pi) but not detected in mucus producing cells. In fact, infected ciliated cells were observed to protrude from the epithelial surface while cilia beating frequency was reduced following infection. Upper left image shows bright green (white) labeling of beta-tubulin in ciliated cells having co-localized monoclonal (m) antibody (Ab) J2 (mabJ2) staining in red (darker areas) show locations of double-strand RNA indicative of viral replication in infected ciliated cells. DAPI stained and blue colored nuclei show in the darkest staining. Upper left image shows bright green (white) labeling of MUC5AC in goblet cells that do not appear to be co-localized with monoclonal (m) antibody (Ab) J2 (mabJ2) staining in red (darker areas) showing locations of double-strand RNA indicative of viral replication. DAPI stained and blue colored nuclei show in the darkest staining. Below each image is a cross-sectional fluorescent image of the epithelial cell layer showing (left) the presence of virus in a ciliated cell as staining positive for beta-tubulin, see white arrow, while the right lower image shows viral staining, red, that is not associated with the MUC5AC staining of goblet cells. FIG. 5E shows an exemplary result of cilia beating frequency (Hz) significantly reduced following infection.

Example 4

Human Rhinovirus Infection Changes Cell Morphology of Ciliated Cells.

This example shows the results of exemplary changes in cell morphology of ciliated cells.

In particular, after 24 hours (h) of Rhinovirus infection ciliated cells shown, in a phase contrast micrograph, are rounded, see, FIG. 6A. Pink arrows point to exemplary rounded cells. This observation is supported by an exemplary graph in FIG. 6B comparatively measuring reduced cilia beating frequency in HRV-16 infected cells as opposed to non-infected controls.

FIGS. 6A-B show an example of human Rhinovirus induces ciliated cells rounding and reduces cilia beating frequency. FIG. 6A shows cells at 24 h post infection: Pink arrows point to examples of rounded ciliated cells. Note the rounded cells moving (blurry) due to cilia beating. These cells are predicted to detach from the epithelium layer/membrane. FIG. 6B shows quantification of cilia beat frequency between non-infected and HRV-16 infected chips. Cilia beating frequency (Hertz: Hz) comparing frequency measured in non-infected to infected chips.

FIGS. 7A-7B shows embodiments for modeling asthma exacerbation on chip by measuring cilia beating frequency and mucociliary transport on-chip for modeling changes in function of Human Airway Epithelium. Although IL-13 stimulation also reduces cilia beating frequency but do not sensitize the epithelium to rhinovirus. FIG. 7A shows a panel of micrographs along with a CBF (cilia beating frequency) (HZ) colorized scale demonstrating cilia beating in FIG. 7A1, a colorized cilia beating frequency micrograph FIG. 7A2 using a CBF scale shown in FIG. 7A3. FIG. 7A4 shows a still shot from a video micrograph of mucociliary transport (i.e. mucociliary escalator) where the white dots are fluorescent microbeads moving across the upper surface of the epithelium. FIG. 7B1-7B2 shows a panel of micrographs demonstrating cilia beating frequency in colorized micrographs a CBF scale shown in FIG. 7B3. FIG. 7B4 shows a chart of cilia beating frequency (Hz). FIG. 7B5 shows comparative HRV-16 viral titers (Log10 TCID50/ml) showing little difference in amount of virus produced in IL-13 co-treatments.

Example 5

Human Rhinovirus Induced Metaplasia in the Upper Cell Layer of the Microfluidic Airway-on-Chip.

This example demonstrates observed exemplary metaplasia of the cell layer in the upper channel of the infected Airway-on-Chip. Metaplasia in general refers to an abnormal change in the nature of a tissue.

One example of metaplasia, shown here, refers to a reversible replacement of one differentiated cell type with another mature differentiated cell type. The change from one type of cell to another may generally be a part of normal maturation process or caused by some sort of abnormal stimulus. However, as supported by the data shown here, metaplasia is induced by the abnormal stimulus of the HRV-16 infection. Thus, after 6 days of Rhinovirus infection, in addition to the loss of cilia staining, an increased number of goblet cell staining was observed in immunofluorescent micrographs of cells in the layer of the upper channel of an infected chip stained with a goblet cell marker, see FIG. 8A, left panel compared to staining of goblet in a non infected chip, infected chip shown in right panel of FIG. 8A. The observed increase goblet cells by mucin staining (red) inside of these cells, is supported by an exemplary graph in FIG. 8B showing significant increase in goblet cells as a percentage of total area. White arrows point to exemplary ciliated cells.

FIG. 8A-B shows an example of human Rhinovirus induced goblet cells metaplasia and induced secretion of pro-inflammatory chemokines. FIG. 8A is a micrograph showing fluorescent imaging of mucus producing cells (Goblet cells (MUCSAC+)-red) before (left) or after 6 days from infection (right). Note that after infection almost all the cells are goblet cells, typical of a goblet cell hyperplasia/metaplasia. MUCSAC staining also suggests increase of apical mucus secretion. Nuclei are shown in blue. FIG. 8B shows quantification of the goblet cells hyperplasia/metaplasia after infection (6 days). Goblet cells (% total area) vs. comparing non infected to HRV-16 infected chips.

Example 6

Human Rhinovirus Secretion of Pro-Inflammatory Chemokines.

This example shows the results of exemplary secretion of cytokines considered pro-inflammatory in this model.

In particular, after 6 days of Rhinovirus infection, amounts of chemokines were measured in fluid collected from the upper and/or lower channel following 24 and 48 hours post-infection with HRV-16. C-X-C Motif Chemokine Ligand 10 (CXCL10) protein is typically secreted upon Interferon-gamma stimulation and found here to be secreted by HRV-16 infected cells but not non infected cells. Secretion of MIP-1 alpha (macrophage inflammatory protein 1 alpha: a member of the CC chemokine family) and MCP-1 (Monocyte chemoattractant protein-1 (MCP-1/CCL2)) was also induced by HRV-16 infection. Both of these chemokines are known chemoattractants for neutrophils. CXCL10 (pg/mL) MIP-1α (pg/mL) MCP-1 (pg/mL). comparing non infected to HRV-16 infected chips at 24 hpi and 48 hpi. See, FIG. 8C.

FIG. 8C shows pro-inflammatory chemokines secreted following HRV-16 infection. CXCL10 is secreted upon Interferon stimulation. MIP-1a and MCP-1 are chemoattractants for neutrophils. CXCL10 (pg/mL) MIP-la (pg/mL) MCP-1 (pg/mL). Comparing non-infected to HRV-16 infected chips at 24 hpi (hours post infection) and 48 hpi. FIG. 8D demonstrates exemplary immunofluorescence staining showing chromatin condensation in nuclei of HRV-infected cells. HRV-16 virions are shown in red. Nuclei stained with DAPI are shown in blue.

Secretory Phases of Inflammatory Cytokines.

HRV-16-induced interferons, chemokines and pro-inflammatory cytokines profile is altered by IL-13 treatment in the severe asthma chip as shown by high resolution, kinetic profiles of cytokine secretion. These graphs (FIG. 17A-C) show results using a method for identifying secretory phases (i.e. I, II, III, and IV) of essential inflammatory cytokines. Here we see that IL-13 treatment inhibits secretion of IFN Lambda 1, CXCL10 and IL-6 (pg/ml) over a period of 3 days (72 hours) while infection with IL-13 results in an increase then decrease of these cytokines.

FIG. 17A-C HRV-16-induced interferons, chemokines and pro-inflammatory cytokines profile is altered by IL-13 treatment in one embodiment of a severe asthma on-chip. These exemplary graphs show results from high resolution, kinetic profiles of an IFN Lambda 1 response FIG. 17A; IP-10/CXCL10 FIG. 17B; IL-6 response FIG. 17C; following HRV16 infection. A severe asthma on-chip was stimulated with IL-13 (lower red line and squares) while a duplicate chip was not stimulated with IL-13 (upper blue line and circles). IL-13 treatment was over 72 hours post infection. Data represent mean±SEM of cells from three to four different donors, with one or two biological replicates (chips) per donor.

Example 7

Inducing an Asthma-Like Phenotype using Exemplary IL-13 Stimulation of Microfluidic Airway-on-Chip.

This example shows an example of one embodiment of an Airway-on-Chip that enables testing of immuno-modulatory compounds e.g. compounds are related to neutrophil recruitment, in a model of acute asthma exacerbation, i.e. severe asthma.

As an exemplary immuno-modulatory compound, addition of IL-13 to an Airway-on-Chip induced changes in epithelial cell layers in the upper channel with an air interface and endothelial cells in the lower channel under media fluid flow conditions are shown. It was discovered that IL-13 added to this embodiment of Airway-on-Chip effects both the epithelial cell layer in the upper channel with an air interface and the endothelial cells in the lower channel under media flow conditions. FIG. 9A is a schematic illustration showing IL-13 in the context of an Airway-on-Chip, where IL-13 effects both epithelial cells in the upper channel with an air interface and endothelial cells in the lower channel under flow (left). Another schematic (right) shows additional detail of a mucociliary airway epithelium (ciliated blue cells and pink large goblet cells) in the process of being contacted (infected) with an exemplary respiratory virus at an MOI of 1 (green dots) in the epithelial channel, where a membrane separates the epithelial channel from the endothelial cells in the vascular channel. IL-13 is added to the endothelial channel at an exemplary 100 ng/ml for an exemplary 7 days.

IL-13 induced goblet cell hyperplasia, see, FIG. 9B, where goblet cells are identified using a marker for Mucin SAC (Mucin 5AC, Oligomeric Mucus/Gel-Forming). This hyperplasia effect can be inhibited by Tofacitinib, an inhibitor of the JAK/STAT pathway (Janus Kinase (JAK) and Signal Transducer and Activator of Transcription (STAT)).

Induced gene expression for adhesion molecules was also observed after IL-13 treatment, FIG. 9C. Examples of IL-13 induced Selectins (P and E) and ICAM-1 (Intercellular Adhesion Molecule 1) and VCAM-1 (vascular cell adhesion molecule-1). Doerr, "The condition-dependent proteome." Nat Methods. 2016 Febuary; 13(2):117. Gene expression in FIG. 9C was correlated with upregulated protein expression observed in fluorescently stained cells shown in FIG. 13B for ICAM1, Vascular cell adhesion molecule 1 (VCAM1) and Vascular endothelial (VE)-cadherin (VE-Cadherin).

FIG. 9C shows effects of IL-13 on endothelial cells: a graphical measurement of gene expression over time compared to non-treated cells shows that IL-13 up regulates adhesion proteins such as Selectins (P and E) and ICAM-1 and VCAM-1 graphed as IL-13-induced gene expression changes (Fold over non-treated vs. agent added to chip). Other compounds tested included Interleukin alpha (IL1A), Interleukin beta (IL1B), Interleukin-6 (IL6), Interleukin-8 (IL8), The chemokine (C-C motif) ligand 2 (CCL2), C-C Motif Chemokine Receptor 4 (CCR4), Protein Tyrosine Phosphatase, Receptor Type C (PTPRC), Intercellular Adhesion Molecule 1 (ICAM1), Selectin P (SELP), Selectin E (SELE), Prostaglandin-Endoperoxide Synthase 2 (PTGS2), Transforming Growth Factor Beta 1 (TGFB1), SMAD Family Member 7 (SMAD7), Complement C3 (C3), Angiotensin I Converting Enzyme (ACE), cluster of differentiation 34: CD34 antigen: CD34 molecule (CD34) and Nuclear Factor Of Activated T-Cells 4 (NFATC4).

FIGS. 13A-C shows exemplary inflammatory response in an Airway-on-Chip model of asthma. In one embodiment, an asthma phenotype was generated using IL-13 stimulation. This stimulation led to the activation of human endothelium at 48 hours of treatment. IL-13 induces vessel (endothelial cell) wall priming as part of recruitment of immune cells. FIG. 13A demonstrates log10 significance differences including p values, at horizontal dotted lines, after staining for endothelial cell proteins vs. differences on a Log2 basis between IL-13 induced cells and a control without treatment with IL-13. FIG. 13B shows effects of IL-13 on endothelial cells: as shown in micrographs of immunostained cells: increased adhesion molecule expression was observed. IL-13 100 ng/mL (right panels) vs. no treatment controls (left panels) VE-Cadherin (red), ICAM-1 (green) in the upper panels. VCAM-1 (red) VE-Cadherin (green). Cell nuclei are stained with DAPI (4′,6-diamidino-2-phenylindole) as shown in blue. FIG. 13C shows quantitative charts of comparative ICAM-1 (upper chart) and VCAM-1 (lower chart) significant induction vs. controls.

Example 8

Inducing a Severe Disease Phenotype, e.g. Stimulating an Asthma-Like Phenotype Combined with Infectious Stimulation, e.g. Viral Infection.

One example of a severe disease phenotype modeled on a microfluidic device of the present inventions is described in this example. Exemplary comparative readouts are also described in this example, however it is not intended to limit the experimental variables to those used in this examples nor limit the types of readouts.

FIGS. 9A-B shows an example of one embodiment of an Airway-on-Chip inducing an asthma-like phenotype using IL-13 stimulation. Creation of a Th2 microenvironment through IL-13 stimulation induces an asthma-like phenotype in the Airway Chip. Exacerbation is then triggered by infecting with human rhinovirus 16. FIG. 9A is a schematic illustration showing IL-13 in the context of an Airway-on-Chip, where IL-13 effects both epithelial cells in the upper channel with an air interface and endothelial cells in the lower channel under flow (left). Another schematic (right) shows additional detail of a mucociliary airway epithelium (ciliated blue cells and pink large goblet cells) in the process of being contacted (infected) with an exemplary respiratory virus at an MOI of 1 (green dots) in the epithelial channel, where a membrane separates the epithelial channel from the endothelial cells in the vascular channel. IL-13 is added to the endothelial channel at an exemplary 100 ng/ml for an exemplary 7 days. FIG. 9B shows effects of IL-13 on epithelial cells: IL-13 induces goblet cells hyperplasia as shown in micrographs of immunostained cells. No treatment, IL-13 treatment, IL-13+Dex (dextran) and IL-13+ Tofacitinib. MUC5AC (Mucin 5AC, Oligomeric Mucus/ Gel-Forming) (green) and cell nuclei are stained with DAPI (4′,6-diamidino-2-phenylindole) as shown in blue.

Additional data shown in FIGS. 10A-B supports the observation that IL-13 treatment does not alter HRV infectivity, FIG. 10A, but impairs epithelial interferon response, FIG. 10B.

FIGS. 10A-B shows examples of charts comparing cytokine expression after HRV-16 infection in a healthy vs. asthmatic background (in this case implementation by comparing Chips under exemplary variables: with and without IL-13 treatment prior to viral exposure: IL-13 treatment does not alter HRV infectivity but impairs epithelial interferon response. FIG. 10A. Shows an exemplary One step growth curves of HRV-16 (MOI=2) in infected Airway chips treated with IL-13 or not. No differences in growth were noted when chips were treated with IL-13. FIG. 10B demonstrates exemplary graphs showing apical interferon response following IL-13 treatment and HRV-16 infection of Airway Chips at 24 h and 48h post infection. Quantification of interferon response shows that IL-13 treatment alter type I and III interferon and interferon stimulated genes CXCL10 and CXCL11 during HRV-16 infection.

FIGS. 11A-B shows exemplary IL-13 stimulation reduces HRV16-induced interferon response thus an antiviral response is altered by IL-13 treatment of chips. Charts show IFN-λ1 (pg/mL) and IP-10/CXCL10 (pg/mL) measured in apical and basal secretions collected at 24, 48 and 72 h post HRV16 infection comparing control, IL-13 alone, HRV-16 alone and combined treatments. Measurements from release in the upper channel are shown in FIG. 11 apical release and in the lower channel FIG. 11B shows corresponding basal secretion.

FIGS. 12A-B shows that exemplary HRV16-induced IL-6 secretion is inhibited by prior stimulation with IL-13. Thus, IL-13 may delay or prevent IL-6-driven resolution of HRV-induced inflammation. Charts (i.e. readouts) show IL-6 (pg/mL) and IL-8 (pg/mL) measured in apical and basal secretions collected at 24, 48 and 72 h post HRV16 infection comparing control, IL-13 alone, HRV-16 alone and combined treatments. Measurements from release in the upper channel are shown in FIG. 12A shows apical release and in the lower channel FIG. 12B shows corresponding basal secretion.

Example 9

Microfluidic Severe Asthma-on-Chip Emulates Acute Asthma Exacerbation and Inflammation Demonstrating the Effect of a CXCR2 Antagonist on Neutrophils This example shows the results of embodiments for a model of Airway-on-Chip for acute asthma exacerbation. In this embodiment, an exemplary respiratory virus, e.g., Rhinovirus, was added to the upper channel of the chip, IL-13 was used to stimulate cells, and neutrophils were added to the lower channel, see, FIG. 14A.

Neutrophils were used as immune cells in part, because neutrophils are the predominant cell type recovered from sputum during acute asthma exacerbations (Fahy, et al., "Prominent neutrophilic inflammation in sputum from subjects with asthma exacerbation." Allergy Clin Immunol. 1995; 95:843-52).

This example also shows the results of exemplary changes in neutrophil adhesion, crawling and extravasation induced by HRV-16 infection, with and without IL-13 stimulation, that is reduced by the use of a C-X-C motif chemokine receptor 2 (CXCR2) inhibitor (in).

HRV-16 infection resulted in an increase in neutrophil attachment in the lower channel, which was increased in cells stimulated with IL-3, see FIG. 14B and FIG. 14C. However, the addition of a CXCR2 inhibitor to cells stimulated with IL-13 alone, actually increased attachment, see, FIG. 14C. In contrast, CXCR2 inhibitor reduced neutrophil attachment for HRV-16 infections, with or without IL-13 stimulation. See, FIG. 14B and FIG. 14C.

In another embodiment, 10 microliters of CXCR2 inhibitor (i.e. a CXCR2 antagonist) added to the lower channel reduced adhesion of neutrophil cells (shown as white dots) on endothelial cell surfaces as shown in FIG. 15B compared to no treatment in FIG. 15A. FIG. 15A shows neutrophils, some exemplary cells identified by pink arrows, in HRV-16 24 hours post infection (hpr) without CXCR2 inhibitor.

Once recruited to the endothelium, neutrophil movement can be recorded and extravasation monitored as N (number) of spots vs. time (e.g. up to 300-600 seconds).

Thus, migratory cell potential, as extravasation, is identified in graphs below each of these micrographs, FIG. 15A and FIG. 15B, showing the number of white spots (N spots) counted over time for each treatment. For HRV-16 infection alone, the number of spots decreases as the cells move into the cell layer, see, FIG. 15C. When treated with a CXCR2 inhibitor, the number of spots remains about the same because the neutrophils that are attached are not moving into the cell layer FIG. 15D. Extravasation in general refers to the movement of white blood cells into the tissues surrounding them (e.g. leukocyte extravasation), also known as diapedesis.

Thus, a CXCR2 antagonist reduces neutrophil mobility and limits trans-migration.

Therefore, this embodiment of an Airway-on-chip enables the study of neutrophil adhesion, crawling and extravasation by demonstrating the capability to monitor neutrophil crawling and trans-migration of cells out of the endothelial channel.

FIGS. 14A-C shows an example of one embodiment of an Airway-on-Chip emulating acute asthma exacerbation by combining Rhinovirus infection with IL-13 stimulation in the presence of an exemplary immuno-modulatory compound: Neutrophil recruitment following exacerbation with HRV can be reduced by an exemplary CXCR2 antagonist MK-7123. FIG. 14A (upper image) shows one embodiment of an Airway-on-Chip that enables testing of immuno-modulatory compounds, e.g. for neutrophil recruitment, in a model of acute asthma exacerbation. HRV-16 is represented as small green dots in the upper channel while neutrophil cells (also described as polymorphonuclear leukocytes (PMN)) are represented as large purple spots in the lower channel. An enlarged schematic is demonstrated schematically in the lower image showing a HRV-infected Airway Chip during perfusion in the vascular channel of freshly isolated human neutrophil. FIG. 14B shows a series of fluorescent micrographs showing comparisons of stained neutrophil cells (red) recruited to the endothelium and attached to non-treated cells. Treatments included HRV-16 alone infected cells, IL-13 alone treated cells, HRV-16 and (+) IL-13 treated cells, HRV-16+CXCR2in (inhibitor) treated cells, and HRV-16+IL-13+CXCR2in. Non-stimulated chips are showing limited neutrophil recruitment while HRV infected and IL-13-treated chips show increased neutrophil recruitment. IL-13+HRV induce an additive increase in neutrophil recruitment, while treatment with a CXCR2 antagonist. MK-7123 (10 microM) significantly reduced neutrophil recruitment under three stimulation conditions. FIG. 14C is a graphical comparison showing PMN (neutrophil) cells counts as % of untreated cells and cells treated with combinations shown for IL-13, HRV, and CXCR2 (in) treatments. Quantification of neutrophil recruitment ( $p<0.01$; ** $p<0.001$).

FIGS. 15A-D shows an example of one embodiment of an Airway-on-Chip demonstrating the effect of a CXCR2 antagonist (inhibitor: in) on neutrophil crawling and trans-migration of cells out of the endothelial channel. FIG. 15A is a micrograph showing effects of HRV-16 infected cells (24 hpi) on cell attachment and FIG. 15B shows effects of HRV-16 infected cells (24 hpi) treated with CXCR2in (10

μM) on cell attachment. FIG. 15C shows a graph of the number of spots (i.e. neutrophil cells: N spots) counted over time (up to 300 seconds) for HRV-16 infected cells (24 hpi). FIG. 15D shows a graph of N spots counted over time (up to 600 seconds) for HRV-16 infected cells (24 hpi) treated with CXCR2in (1004).

Example 10

CF Cell Lines for use in Microfluidic Chips.

This example contemplates creating exemplary CF cell lines for use in microfluidic chips described herein.

Thus, a CF cell line may be generated by collecting cells from a CF patient. For a contemplative example, cystic fibrosis (CF) tracheo-bronchial cells may be transformed with SV40. In a further example, cells from a relative having only one mutated allele may also be transformed with SV40. In some embodiments, an immortal CF cell line may be generated from any one or more patients having a mutated CF gene. Alternatively, a healthy cell may be transformed to induce one or more mutations from the at least 1,000 mutations in the CFTR gene associated with CF, for use in a microfluidic chip as described herein.

A demonstration of such transformed CF cells are shown where a CFBE41o-cell line was generated by transformation of cystic fibrosis (CF) tracheo-bronchial cells, reported to be homozygous for a commonly found ΔF508 mutation, with SV40 large T antigen by using a replication defective pSVori-plasmid. Passages 4-5 of primary bronchial epithelial cells may be used.

An assessment of optimal culture conditions, the expression pattern of drug-transport-related proteins and the stability/presence of the CF transmembrane conductance regulator (CFTR) mutation in the gene and gene product over multiple passages are also described. The CFBE41o-cell line can be also compared with a wild-type airway epithelial cell line, 16HBE14o-, which can serve as model for bronchial epithelial cells in situ. The CFBE41o-cell line retains at least some aspects of human CF bronchial epithelial cells, such as the ability to form electrically tight cell layers with functional cell-cell contacts, when grown under immersed (but not air-interfaced) culture conditions. The cell line is homozygous for ΔF508-CFTR over multiple passages in culture and expresses a number of proteins relevant for pulmonary drug absorption (e.g. P-gp, LRP and caveolin-1). Hence, the CFBE41o-cell line should be useful for studies of CF gene transfer or alternative treatment with small drug molecules and for the gathering of further information about the disease at the cellular level, without the need for primary culture. See, Ehrhardt, et al., "Towards an in vitro model of cystic fibrosis small airway epithelium: characterization of the human bronchial epithelial cell line CFBE41o-". Cell Tissue Res (2006) 323: 405-15.

Thus, in some embodiments, a CFBE410-cell line is contemplated for use in a microfluidic Small Airway on Chip. In some embodiments, a microfluidic CF on a chip is treated to generate an exacerbated CF chip.

Example 11

Microfluidic COPD Chip Emulates Damage Induced by Chronic Exposure to Cigarette Smoke.

This example contemplates inducing COPD on a chip by chronic aerosol exposure to airway epithelium. Thus, in one embodiment, smoke is delivered as an aerosol from one or more sources, such as a specific type of tobacco leaf or combination thereof, a specific name brand of cigarette, a specific name brand of cigar, name brand of pipe tobacco, etc., for inducing COPD on a chip. For example, effects upon neutrophils and goblet cells in particular are evaluated. Specifically, neutrophil migration and function will be evaluated, as described herein for other types of chips. Goblet cell function and secretion will also be evaluated. However it is not meant to limit evaluation of such cells. In fact, changes in ciliary function and mucus will be evaluated. In further, embodiments, carcinogenic potential of such exposure to aerosolized (vaporized) tobacco is evaluated.

In one embodiment, the present invention contemplates infectious agents on a COPD background. For example, a microfluidic airway chip as described herein, is seeded with cells derived from a COPD patient. This chip is then infected with at least one infectious agent, such as a virus, bacteria and fungi, as described herein, associated with inflammatory airway diseases including but not limited to severed asthma, CF, etc. In some embodiments, COPD cells are treated with an inflammatory cytokine, such as IL-13, before infection. In some embodiments, COPD cells are treated with an inflammatory cytokine, such as IL-13, after infection with a microbe. Thus, in some embodiments, a microfluidic COPD on a chip is treated to generate an exacerbated COPD chip. In some embodiments, infection of COPD cells with a microbe is followed by a cytokine/chemokine analysis to determine contributing factors. In some embodiments, neutrophils and added to COPD cells. Neutrophils may be added to COPD chips with and without infection and with or without an added cytokine/chemokine. In some embodiments, other immune cells such as described herein are added to a COPD chip. In some embodiments, COPD chips are used for testing potential therapeutics.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

Example 12

Adhesion Assay and Bacterial Counting Protocol (Method).

Exemplary on-chip infection and analysis of surface-adherent bateria. Bacteria from log phase cultures were collected and washed with PBS. Three $(3) \times 10^6$ CFU/chip per strain were added to airway chips at an MOI of approximately 10. Where the multiplicity of infection or MOI refers to the ratio of microbial agents (e.g. virus, bacteria) to infection targets, in this case chips containing airway cells. Infect for 1 hour (1 hpi), wash 3× in PBS to remove nonadherent bacteria. Cells were trypsinized gently so as to avoid lysing them, therefore intracellular bacteria do not contribute to the CFU counts. Cell samples were collected, e.g. washed, from chips then vortexed to disassociate cell clumps. Samples were serially diluted for CFU quantification. At least N=3 per treatment.

In order to quantify both extracellular and intracellular bacteria concurrently from a single chip, after infection unattached cells in the inoculum were removed, wash 3× with PBS and lyse cells (but not bacteria) with 1% triton. This allows counting surface-associated and intracellular bacteria cell numbers.

In order to quantify mainly intracellular bacteria, cells were treated with antibiotics to kill extracellular bacteria, antibiotics were removed, cells were washed and lysed with 1% triton. The CFU counts obtained in this assay represent intracellular bacteria counts as extracellular bacteria are killed.

Example 13

Exemplary on-Chip Infection Protocol.

Bacteria from log phase cultures were collected and washed with PBS.

Three $(3) \times 10^6$ CFU/chip per strain were infected at an MOI of approximately 10. Infect for 2 h, wash 3× PBS to remove nonadherent bacteria.

Mature small airway chips at air-liquid interface (ALI) were gently washed with PBS to remove excess mucus. Cells were inoculated with $2\text{-}3 \times 10^6$ colony forming units (CFUs) in Hank's balanced salt solution (HBSS) for 2 hours. At the end of the incubation, the inoculum was removed and the cells were washed 3× with phosphate buffer saline (PBS) to remove any nonadherent bacteria. PBS was removed and cells were incubated at ALI up to 24 hours (h) under flow in the bottom channel but not in the top channel.

Example 14

Microfluidic Chip Emulates Damage Induced by Infectious Microbes: i.e. Changes in Mucociliary Activity.

FIGS. 20A-B shows exemplary real time imaging after infection of one embodiment of an Airway Chip with bacteria *P. aeruginosa* infection on chip. Both pseudomonas strains, wild-type (WT) and mutant, form micro-colonies/aggregates on airway chip. Bacterial inoculum was plated and CFU were counted to ensure target MOI. Images were acquired 24 hpi. FIG. 20A PA 5919-WT. FIG. 20B PA 5890-Mutant. Left: Alexa fluor 488-anti-*P. aeruginosa* (Pa) antibody. Central: Bright-field. Right: Alexa fluor 488-anti-*P. aeruginosa* (Pa) antibody-Bright-field.

FIGS. 21A-C shows exemplary immunofluorescence, with Z-stacks or a side view, after infection of one embodiment of an Airway Chip with bacteria *P. aeruginosa* infection on chip. Pseudomonas establishes an intracellular niche as well as forming extracellular micro-colonies on the epithelial cell surface. Z-stacks are shown as a bar across the top (to the right of the 24 h label, and the down the right side of the micrographs. The upper (or right side on the side bar) part of the Z-stacks represent apical regions then down through the cells to the basil regions at the bottom of bar (or left side of the side bar). These Z-stacks indicate that bacterium are intracellularly located. FIG. 21A PA 5919-WT. Actin (red); Pa (green); DAPI (blue). FIG. 21B PA 5890-Mutant. Actin (pink); Pa (green); DAPI (blue). Images were acquired 24 hpi. FIG. 21C shows a confocal immunofluorescent micrograph side view of a. cell layer infected with *P. aeruginosa* in a microfluidic airway chip, 24 hours post infection. Actin (pink); Pa (green); DAPI (blue). Bacterial aggregates on apical surface as well as intracellular bacteria are observed.

Observing Changes in Mucociliary Activity, i.e. Readouts.

FIGS. 22A-C shows exemplary mucociliary activity photographed in bright field on one embodiment of a *Pseudomonas* infection on chip. Micrographs represent one image from a video of cilia beating on-chip. FIG. 22A shows non-infected control microfluidic chip image representing beating cilia. FIG. 22B PA 5890 shows Mutant infected microfluidic chip image representing loss of beating cilia. FIG. 22C PA 5919 shows WT microfluidic chip image also representing a loss of beating cilia.

FIG. 23 shows an exemplary comparison of cilia beating frequency (CBF) between *Pseudomonas* strains in one embodiment of a *Pseudomonas* infection on chip. Images from a video of epidermal cells' cilia beating on-chip were quantitatively evaluated showing that both wild type and mutant strains has altered cilia beating frequency compared to controls without added bacteria.

FIG. 24 an exemplary comparison of cellular cilia coverage after infection with *Pseudomonas* strains in one embodiment of a *Pseudomonas* infection on chip. Mutant (increases) and WT (decreases) show significant differences in density compared to controls.

FIG. 25 shows an exemplary Bacterial adherence on chip in one embodiment of a microfluidic airway epithelia. *P. aeruginosa* WT (MB5980) and mutant (MB5919) strains adhere to airway epithelium at similar rates. Unpaired t-tests $p=0.0641$. N=3.

Example 15

Treatment of Microfluidic Chip with an Anti-Microbial Compound.

After an exemplary on-chip infection protocol, including removing nonadherent bacteria, a test compound was immediately added to the top (apical) and bottom (basal) channels then cells are cultured under flow using media containing the anti-microbial compound, for 24 hours. Exemplary test compound amounts are at least 0.1 µg/ml, up to 50 µg/ml, up to 100 µg/ml, up to 500 µg/ml. In one embodiment, an exemplary test compound is a drug Imipenem.

More specifically, in one embodiment of an Airway on-chip, duplicate chips were infected with PA 5919 WT or PA 5890 Mutant as described herein. Then, Imipenem was added to apical and basolateral fluids (cell media) for treatment with Imipenem at 50, 100 and 500 µg/ml for 24 hours with at least one chip without Imipenem. At 24 h post treatment, wash cells 3× to remove the test drug, i.e. antibiotic Imipenem. Cells lysed with 1% Triton for 10 minutes on chip, then the lysate was collected from the chip's channels. Lysates were serially diluted for CFU quantification. N=2.

Assay readouts: Viability of extracellular bacteria (apical sampling). Viability of intracellular bacteria (cell lysis and sampling). Two-way ANOVA with Dunnett's post-test <0.05, <0.001 (compared to untreated).

Imipenem treatment has significant bactericidal effect on MB5890 (mutant) strain and MB5919 (WT) growth. Imipenem kills most of the extracellular bacteria (this was determined by plating out apical supernatants), however does not rule out that there are still surface-associated extracellular bacteria on the epithelium. There is reduction in total bacterial counts (intra- and/or extracellular bacteria) but at this stage we cannot determine if bacteria remaining post imipenem treatment are both intra and extracellular. However, the results clearly show *P. aeruginosa* killing post antibiotic treatment as indicated in CFU counts and that the bacteria can persist in small airway cells over time.

Airway cells are impermeable to imipenem at lower concentrations. *P. aeruginosa* can persist in small airway cells over time when treated with 50 ug/ml imipenem.

FIGS. 26A-B shows an exemplary Imipenem (Merck compound) effects on *P. aeruginosa* infection compared between Transwell cultures and on-chips. FIG. 26A shows exemplary Imipenem (Merck compound) effects on *P.*

*aeruginosa* infection in a Transwell culture. FIG. 26B Imipenem treatment reduces total bacterial counts via bacterial killing in one embodiment of a *P. aeruginosa* infection on chip. Two-way ANOVA with Dunnett's post-test <0.05, <0.001 (compared to untreated).

FIGS. 27A-C shows exemplary Imipenem (Merck compound) effects on *P. aeruginosa* infection, WT vs. mutant, on airway cells in Transwells. FIG. 27A shows exemplary Imipenem treatment. FIG. 27B shows exemplary Carbenicillin treatment. FIG. 27C shows exemplary Tetracycline treatment. Two-way ANOVA with Dunnett's post-test <0.05, <0.001, ***<0.0001 (compared to untreated).

FIGS. 28A-C shows exemplary real time imaging of Imipenem effects on *P. aeruginosa* infection on one embodiment of a PA 5919 WT *Pseudomonas* infection on chip. *P. aeruginosa* infection shown on chip with WT strain (green). FIG. 28A show an untreated, infected control. FIG. 28B shows infection on-chip treated with 50 µg/ml Imipenem. FIG. 28C shows infection on-chip treated with 500 µg/ml Imipenem for 24 h. There is an obvious reduction in bacterial load indicated by the reduction in fluorescent bacteria as shown by live imaging. Imipenem effect is demonstrated by bacterial killing and control of infection. PA 5919 WT 24 hpi. Left: Alexa fluor 488-anti-*P. aeruginosa* (Pa) antibody. Central: Bright-field. Right: Alexa fluor 488-anti-*P. aeruginosa* (Pa) antibody-Bright-field.

FIGS. 29A-C shows exemplary Real time imaging of Imipenem effects on *P. aeruginosa* infection on one embodiment of a PA 5890 Mutant 24 hpi *Pseudomonas* infection on chip. FIG. 28A untreated (noninfected) control. FIG. 28B infection treated with 50 ug/ml imipenem. FIG. 28C infection treated with 500 ug/ml imipenem for 24 h. PA 5890 Mutant 24 hpi. Left: Alexa fluor 488-anti-*P. aeruginosa* (Pa) antibody. Central: Bright-field. Right: Alexa fluor 488-anti-*P. aeruginosa* (Pa) antibody-Bright-field.

Example 16

*S. pneumoniae* spp. Infection on-Chip

An exemplary airway on-chip was infected with *S. pneumoniae* serotype 1 at multiplicity of infection of 1 and 10, respectively for 24 h. The infection protocol follows 1) inoculation with $10^6$ or $10^7$ CFU/ml for 1 hour; 2) 3× PBS wash to remove nonadhered bacteria; 3) removing all media to return lung-chip at air-liquid interface; and 4) incubation up to 24 h of infection. Bacteria labelled in green are found intracellularly (arrows) as shown by the orthogonal z-stack section imaging by confocal microscopy. These chip experiments show that *S. pneumoniae* infection on chip closely mimics in vivo infection such as pneumonia where intracellular bacteria are reported to present in human lung and infiltrate into the tissue.

FIGS. 30A-B shows an exemplary embodiment of an airway-chip infected with *S. pneumoniae* serotype 1. Bacteria labeled in green are found intracellularly (arrows) as shown by the orthogonal z-stack section imaging by confocal microscopy. FIG. 30A shows an exemplary infection of Sp at MOI 1. F-actin immunostain shown in red; B-tubulin immunostain shown in purple; Bacteria immunostain shown in green. Cell nuclei DAPI stained and shown in blue. FIG. 30B shows an exemplary infection of Sp at MOI 10. F-actin immunostain shown in red; MUC5AC immunostain shown in yellow; Bacteria immunostain shown in green. Cell nuclei DAPI stained and shown in blue.

Example 17

Measuring Human β-Defensin 2 Secretion Post-Infection.

Prolonged *P. aeruginosa* infection results in enhancement of HBD-2 protein secretion. Human β-Defensin 2 is detected in apical secretions in *P. aeruginosa* infected airway-chip 24 hpi, see, FIG. 31. Human β-Defensin 2 was measured in epithelial apical secretions using ELISA. Significance is **<0.05 according to an unpaired t-test.

FIG. 31 shows an exemplary secretion of Human β-Defensin 2 post *P. aeruginosa* infection on one embodiment of a microfluidic Airway Chip. For comparison, HBD-2 protein (pg/ml) was measured in control chips; after WT *P. aeruginosa*; and a mutant strain of *P. aeruginosa* were tested for Human β-Defensin 2 secretion in apical wash, 24 hpi. Unpaired t-test, **<0.05. N=2.

Example 18

Induction of Apoptosis in Host Cells Post *P. aeruginosa* Infection.

One embodiment of an Airway On-Chip was infected as described above for 2 hours and then treated 50 µg/ml tetracycline for 24 h (top and bottom channels under flow) for 24 h in order to limit bacterial replication (to avoid over-replication and cell lifting). Using this methodology, we performed longer infections on an airway chip and avoided cell death at 24 h. At 24 h, chips were fixed with 4% paraformaldehyde for 15 minutes and subsequently permeabilized with 0.25% triton in PBS. Apoptosis staining was performed following the Click-iT™ Plus TUNEL Assay for In Situ Apoptosis Detection, Alexa Fluor 647 assay: Click-iT™ Plus TUNEL Assay, Thermo Fisher Scientific Inc., 6 Nov. 2017.

The TUNEL assay is based on the incorporation of modified dUTPs by the enzyme terminal deoxynucleotidyl transferase (TdT) at the 3'-OH ends of fragmented DNA, a hallmark as well as the ultimate determinate of apoptosis. ClickiT™ Plus TUNEL assay with the Alexa Fluor™ 647 dye was utilized to detect the fragment DNA (purple), nuclei were labelled with DAPI. Uninfected cells show very limited apoptosis, whereas *P. aeruginosa* infected chips exhibited a significant increase in the number of apoptotic cells.

Staurosporin, a prototypical ATP-competitive kinase inhibitor, was used as a positive control in this assay. Chips incubated with 3 µM staurosporin for 3 h at 37° C. had increased apoptotic cell numbers. As an additional positive control, chips were treated with 1 unit of DNAse I for 30 minutes at room temperature to induce TUNEL positive DNA strand breaks. As shown in the figure, almost all DNAse I treated cells underwent apoptosis post treatment.

FIGS. 32A-D shows exemplary apoptosis via TUNEL staining at 24 h post infection. Apoptotic, TUNEL+, (pink); nuclei, DAPI+, (blue). FIG. 32A uninfected; FIG. 32B Pa infected; FIG. 32C staurosporin treatment. Staurosporin refers to an ATP-competitive kinase inhibitor. FIG. 32D DNAse I treatment. DNAse I refers to an endonuclease that nonspecifically cleaves DNA to release di-, tri- and oligo-nucleotide products with 5'-phosphorylated and 3'-hydroxy-lated ends. DNase I acts on single- and double-stranded DNA, chromatin and RNA:DNA hybrids.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, molecular biology, cell biology, genetics, statistics microfluidics or related fields are intended to be within the scope of the following claims.

What is claimed is:

1. A method of culturing, comprising:
   a) providing i) a microfluidic device comprising first and second channels, said first channel comprising lung cells at an air-liquid interface, and ii) a solution of bacteria;
   b) introducing said solution of bacteria into said first channel such that said bacteria contact and adhere to said lung epithelial cells to produce adhered bacteria; and
   c) removing said solution of bacteria; and
   d) culturing said lung epithelial cells and said adhered bacteria at an air-liquid interface in the absence of fluid flow in said first channel to produce viable cultured epithelial cells.

2. The method of claim 1, wherein said lung epithelial cells are small airway cells.

3. The method of claim 1, further comprising, prior to step b) removing mucus from said first channel.

4. The method of claim 1, wherein said solution of bacteria comprises $2-3\times10^6$ colony forming units (CFUs) in Hank's balanced salt solution (HBSS).

5. The method of claim 1, wherein said solution of bacteria is in said first channel for 2 hours.

6. The method of claim 1, further comprising, prior to step d), removing any nonadherent bacteria.

7. The method of claim 1, further comprising flowing culture media in said second channel, and not in said first channel.

8. The method of claim 1, wherein said lung epithelial cells are fully differentiated mucociliary bronchiolar airway cells.

9. The method of claim 1, wherein said bacteria are *S. pneumoniae*.

* * * * *